US00RE38490E

(19) United States
(12) Reissued Patent
Thompson

(10) Patent Number: US RE38,490 E
(45) Date of Reissued Patent: Apr. 6, 2004

(54) METHOD FOR IDENTIFYING METASTATIC SEQUENCES

(75) Inventor: Timothy C. Thompson, Houston, TX (US)

(73) Assignee: Baylor College of Medicine, Houston, TX (US)

(21) Appl. No.: 09/977,371

(22) Filed: Oct. 16, 2001

Related U.S. Patent Documents

Reissue of:
(64) Patent No.: 5,783,182
Issued: Jul. 21, 1998
Appl. No.: 08/594,031
Filed: Jan. 30, 1996

(63) Continuation of application No. 09/469,316, filed on Dec. 22, 1999, now abandoned.
(60) Provisional application No. 60/006,838, filed on Nov. 16, 1995.

(51) Int. Cl.[7] ..... A61K 48/00
(52) U.S. Cl. ..... 424/93.21; 435/375; 435/6; 435/455; 435/467; 435/69.1; 800/18
(58) Field of Search ..... 424/93.21; 435/375, 435/6, 69.1, 467, 455; 800/18

(56) References Cited

U.S. PATENT DOCUMENTS

| | | | |
|---|---|---|---|
| 4,317,818 | A | 3/1982 | Benson et al. |
| 4,925,835 | A | 5/1990 | Heston |
| 5,116,615 | A | 5/1992 | Gokcen et al. |
| 5,260,224 | A | 11/1993 | Stossel et al. |
| 5,633,161 | A | 5/1997 | Shyjan |
| 5,783,182 | A | 7/1998 | Thompson |
| 5,834,234 | A | 11/1998 | Gallo |

FOREIGN PATENT DOCUMENTS

| | | |
|---|---|---|
| WO | WO 86/03226 | 6/1986 |
| WO | WO 94/04196 | 3/1994 |
| WO | WO 94/16737 | 8/1994 |
| WO | WO 94/28129 | 12/1994 |
| WO | WO 95/19369 | 7/1995 |
| WO | WO 96/30389 | 10/1996 |
| WO | WO 97/09055 | 3/1997 |
| WO | WO 97/18454 | 5/1997 |
| WO | WO 99/22773 | 5/1999 |

OTHER PUBLICATIONS

Welch, Danny R., et al. "Transforming growth factor β stimulates mammary adenocarcinoma cell invasion and metastatic potential", *Proc. Natl. Acad. Sci. USA*, vol. 87, pp. 7678–7682. Oct. 1990.

Thompson, Timothy C., et al. "Multistage Carcinogenesis Induced by ras and myc Oncogenes in a Reconstituted Organ", *Cell*, vol. 56, pp. 917–930. Mar. 24, 1989.

Fingert et al., "In vivo model for differentiation therapy of leukemia and solid tumors." *National Institutes of Health Publication*, 84–2635, Serno Symposia Publications from Rven. Press, pp. 277–286 (1984).

Taber's Cyclopedic Medical Dictionary, F.A. David Company, Philadelphia, PA, edited by Vardara et al. (1993).

Liang, Peng, et al., "Differential Display and Cloning of Messenger RNAs from Human Breast Cancer versus Mammary Epithelial Cells", *Cancer Research*, 52, pp. 6966–6968. Dec. 15, 1992.

Merz, et al. "Elevated Transforming Growth Factor–β1 and β3 MRNA Levels are Associated with ras + myc–Induced Carcinomas in Reconstituted Mouse Prostate: Evidenced for a Paracrine Role during Progression". *Molecular Endocrinology*, vol. 5, No. 4, (1991) pp. 503–513.

Poster Session Abstracts: First SPORE Investigators' Meeting, "The Role of Retinoids in Prostate Cancer Chemoprevention" Jul. 18–20, 1993, p. 30.

Slawin, et al. "Dietary Fenretinide, a Synthetic Retinoid, Decreases the Tumor Incidence and the Tumor Mass of ras + myc–induced Carcinomas in the Mouse Prostate Reconstitution Model System", *Cancer Research*, vol. 53, pp. 4461–4465, Oct. 1, 1993.

Thompson, et al. "Transgenic Models for the Study of Prostate Cancer", (Supplement) *Cancer*, vol. 71, No. 3, Feb. 1, 1993, pp. 1165–1171.

Donehower, et al. "Mice deficient for p53 are developmentally normal but susceptible to spontaneous tumours", *Articles, Nature*, vol. 356, Mar. 19, 1992, pp. 215–221.

Thompson, et al., "Loss of p53 function leads to metastasis in ras + myc–initiated mouse prostate cancer", *Oncogene* (1995) vol. 10, pp. 869–879.

Macoska, et al. "Loss of the 17p Chromosomal Region in a Metastatic Carcinoma of the Prostate", *The Journal of Urology*, vol. 147, Apr. 1992, pp. 1142–1146.

Taylor, et al. "Evidence for synergistic interactions between ras, myc and a mutant form of p53 in cellular transformation and tumor dissemination", *Oncogene*, Feb. 10, 1992, pp. 1383–1390.

Hall, et al. "Adenylate Kinase: An Oncodevelopmental Marker in an Animal Model for Human Prostatic Cancer", *Clinical Chemistry*, vol. 31, No. 10, (1985), pp. 1689–1691.

Thompson et al., Multistage Carcinogenesis Induced by ras and myc Oncogenes in a Reconstituted Organ, *Cell*, vol. 56, pp. 917–930, Mar. 24, 1989.

(List continued on next page.)

*Primary Examiner*—Deborah Crouch
(74) *Attorney, Agent, or Firm*—Vinson & Elkins L.L.P.

(57) ABSTRACT

The invention relates to methods for the identification of metastatic sequences. Cells from a cell line or an animal tissue are treated to form a cell line predisposed to metastasis. Treated cells are implanted in an animal [of] *at* a primary site and incubated for a period of time sufficient for the cells to proliferate and develop metastases at secondary sites. Expressed sequences from cells at the primary and secondary sites are amplified by differential display polymerase chain reaction and compared. Differentially expressed sequences are [identical] *identified* and can be cloned and sequenced. These sequences can be used as probes in the diagnosis of metastatic disorders, as probes to isolate metastatic sequences and as a therapeutic agent.

8 Claims, 63 Drawing Sheets

OTHER PUBLICATIONS

Slawin, et al., American Urological Association, Inc., Annual Meeting—San Antonio, Oct. 1, 1992, Dietary Retinoids Decrease the Incidence and Increase Lymphocytic Infiltration of ras + myc Induced Carcinomas in the Mouse Prostate Reconstitution Model System.

Thompson, et al., "Transforming Growth Factor β1 as a Biomarker for Prostate Cancer", *Journal of Cellular Biochemistry*, Supplement 16H: pp. 54–61 (1992).

Thompson et al. "Genetic Predisposition and Mesenchymal–Epithelial Interactions in ras + myc–Induced Carcinogenesis in Reconstituted Mouse Prostate" *Molecular Carcinogenesis*, vol. 7, pp. 165–179 (1993).

Bookstein et al. "p53 Is Mutated in a Subset of Advanced–Stage Prostate Cancer[1]", *Cancer*, vol. 53, pp. 3369–3373, Jul. 19, 1993.

Carter, et al. "Prediction of Metastatic Potential in an Animal Model of Prostate Cancer: Flow Cytometric Quantification of Cell Surface Charge", *The Journal of Urology*, vol. 142, pp. 1338–1341, Nov. 1989.

Fox, et al. "p53 And c–myc Expression in Stage A1 Prostatic Adenocarcinoma: Useful Prognostic Determinants?" *The Journal of Urology*, vol. 150, pp. 490–494, Aug. 1993.

Einstein, "Hormonal Therapy for Prostate Cancer—When to Use it", *Cancer Control*, Jan./Feb. 1995, pp. 32–36.

Thompson, et al., "Loss of p53 Function Leads to Metastasis in ras + myc– Initiated Mouse Prostate Cancer", Abstract for Fogarty International Meeting, Jun. 26–28, 1995.

Xiong, et al. "Human D–Type Cyclin," *Cell*, vol. 65: pp. 691–699 (May 17, 1991).

Manam, et al., "Dose related changes in the profile of ras mutations in chemically induced CD–1 mouse liver tumors," *Carcinogenesis*, vol. 16(5) pp. 1113–1119 (May 1995).

Blok, et al., "Isolation of cDNA's that are differentially expressed between antrogen–dependent and androgen independent prostate carcinoma cells using differential display PCR." *Prostate*, vol. 26(4), pp. 213–224 (Apr. 1995).

Wu, et al. "Identification of a human hepatocellular carcinoma–associated tumor suppressor gene by differential display polymerase chain reaction," *Life Sciences*, vol. 57(11), pp. 1077–1085 (Nov. 1995).

Schneider, et al. "7,12–Dimethylben[a] anthracene–Induced Mouse Keratinocyte Malignant Transformation Independent of Harvey ras Activation," *J. of Investigative Dermatology*, vol. 101(4), pp. 595–599 (Oct. 1993).

Neumann, H.G., "entstehung und Behandlung von Turoren, Immunosupressive", *Allgemeine und Specielle Pharmakologie and Toxikologie*, Edition 5. 1987.

Schlag P.M., "Fruherkennung von Krebs mit Hilfe von molekulariologischen Markern", *Onkologie*, 18, pp. 207, 1995.

Truong, et al. "Association of Transforming Growth Factor–$\beta_1$ with Prostate Cancer: An Immunohistochemical Study," *Human Pathology*, vol. 24, No. 1, pp. 4–9 (Jan. 1993).

Aihara, et al., "Frequency of Apoptotic Bodies Positively Correlates with Gleanson Grade in Prostate Cancer," *Human Pathology*, vol. 25, No. 8, pp. 797–801 (Aug. 1994).

Egawa, et al., "Alterations in mRNA levels for Growth–Related Genes after Transplantation into Castrated Hosts in Oncogene–Induced Clonal Mouse Prostate Carcinoma," *Molecular Carcinogenesis*, vol. 5, pp. 52–61 (1992).

Glenney, "Tyrosine Phosphorylation of a 22–kDa Protein is Correlated with Transformation by Rous Sarcoma Virus," *The Journal of Biological Chemistry*, vol. 264, No. 34, pp. 20163–20166 (1989).

Chen, et al., "Isolation and Characterization of the Promoter Region of Human nm23–H1, a Metastasis Suppressor Gene," Abstract 122:2406 (1994).

Sargiacomo, et al., "Oligomeric Structure of Caveolin: Implications for Caveoale Membrance Organization," *Proc. Natl. Acad. Sci. USA*, vol. 92, pp. 9407–9411 (Sep. 1995).

Tulchinsky, et al., "Transcriptional analysis of the mts1 gene with specific reference to 5' flanking sequences," *Proc. Natl. Acad. Sci. USA*, vol. 89, pp. 9146–9150 (Oct. 1992).

Yang, et al. "Association of Caveolin Protein with Prostate Cancer Progression", *Journal of Urology*, vol. 157, No. 4, p. 446, Abstract #1742 (Apr. 1997).

Eastham, et al. "Prostate Cancer Gene Therapy: Herpes Simplex Virus Thymidine Kinase Gene Transduction Followed By Ganciclovir in Mouse and Human Prostate Cancer Models", *Human Gene Therapy*, vol. 7, pp. 515–523. Mar. 1, 1996.

Ren, et al. "Identification and characterization of p53 regulated genes in a mouse prostate cancer cell line". AACR Annual Meeting, Mar. 28–Apr. 1, 1998, New Orleans, LA.

Goltsov, et al. "A novel p53–regulated gene encoding a four transmembrane domain protein in mouse prostate cancer cells", AACR Annual Meeting, Apr. 10–14, 1999, Philadelphia, PA.

Ren, et al. "Reduced Lysyl Oxidase in RNA Levels in Experimental and Human Prostate Cancer", *Cancer Research*, vol. 58, pp. 1–6, Mar. 15, 1998.

Nelson, Joel B. "Alternatives to death: Understanding androgen–independent prostate cancer", *Nature Medicine*, vol. 4, No. 9, pp. 1011–1012, Sep. 1998.

Yang et al. "Elevated Expression of Caveolin Is Associated With Prostate and Breast Cancer", *Clinical Cancer Research*, vol. 4, pp. 1873–1880, Aug. 1998.

Fielding, et al. "Caveolin mRNA levels are up–regulated by free cholesterol and down–regulated by oxysterols in fibroblast monolayers", *Proc. Natl. Acad. Sci. USA*, vol. 94, pp. 3753–3758, Apr. 1997.

Nasu, et al. "Suppression of caveloine expression induces androgen sensitivity in metastatic androgen–insensitive mouse prostate cancer cells", *Nature Medicine*, vol. 4, No. 9, pp. 1062–1064, Sep. 1998.

Bist, et al. "Two sterol regulatory element–like sequences mediate up–regulation of caveolin gene transcription in response to low density lipoprotein free cholesterol", *Proc. Natl. Acad. Sci. USA*, vol. 94, pp. 10693–10698, Sep. 1997.

Li, et al. "Src Tyrosine Kinases, $G_\alpha$ Subunits, and H–Ras Share a Common Membrane–anchored Scaffolding Protein, Caveolin", *The Journal of Biological Chemistry*, vol. 271, No. 46, pp. 29182–29190, 1996.

Eastham, et al. "In Vivo Gene Therapy with p53 or p12 Adenovirus for Prostate Cancer", *Cancer Research*, vol. 55, p. 5151–5155, Nov. 15, 1995.

Eastham, et al. "Transforming Growth Factor–$\beta_1$: Comparative Immunohistochemical Localization in Human Primary and Metastatic Prostate Cancer", *Laboratory Investigation*, vol. 73, No. 5, pp. 628–635 (1995).

Aihara, et al. "The Frequency of Apoptosis Correlates with the Prognosis of Gleason Grade 3 Adenocarcinoma of the Prostate". *Cancer*, vol. 75, No. 2, pp. 522–529 (Jan. 15, 1995).

Yang, et al., "Perineural Invasion of Prostate Carcinoma Cells is Associated with Reduced Apoptotic Index", *Cancer*, vol. 78, No. 6, pp. 1267–1271 (Sep. 15, 1996).

Chamness, et al., "The effect of androgen on nitric oxide synthase in the male reproductive tract of the rat", *Fertility and Sterility*, vol. 63, No. 5, pp. 1101–1107 (May 1995).

Stapleton, et al., "Primary Human Prostate Cancer Cells Harboring p53 Mutation are Clonally Expanded in Metastates", *Clinical Cancer Research*, vol. 3, pp. 1389–1397 (Aug. 1997).

Koleske, et al., "Reduction of caveolin and caveolae in oncogenically transformed cells", *Proc. Natl. Acad. Sci. USA*, vol. 92, pp. 1381–1385 (Feb. 1995).

Kagan, Herbert M., "Regulation of Matrix Accumulation", Academic Press, Inc., pp. 321–398 (1986).

Kagan, et al., "Properties and Function of Lysyl Oxidase", *AM. J. Respir. Cell Mol. Biol.*, vol. 5, pp. 206–210 (1991).

Feres–Filho, et al., "Pre– and Post–translational Regulation of Lysyl Oxidase by Transforming Growth Factor–β1 in Osteoblastic MC3T3–E1 Cells", *The Journal of Biological Chemistry*, vol. 270, No. 51, pp. 30797–30803 (Dec. 22, 1995).

Shanley, et al., "Transforming growth factor–$\beta_1$ increases lysyl oxidase enzyme activity and mRNA in rat aortic smooth muscle cells", *Journal of Vascular Surgery*, vol. 25, No. 3, pp. 446–452 (Mar. 1997).

Boak, et al., "Regulation of Lysyl Oxidase Expression in Lung Fibroblasts by Transforming Growth Factor–$\beta_1$ and Prostaglandin $E_2$", *American Journal of Respiratory Cell and Molecular Biology*, vol. 11, pp. 751–755 (1994).

Kavirikko, et al., "Posttranslational Modifications of Collagen and Their Alterations in Heritable Diseases", pp. 263–292.

Danks, David M., "Disorders of Copper Transport: Menkes Disease and the Occipital Horn Syndrome", *Connective Tissue and Its Heritable Disorders*, pp. 487–505 (1993).

Kivrikko, Kari L., "Collagens and their Abnormalities in a Wide Spectrum of Diseases", *Annals of Medicine* 25: pp. 113–126 (1993).

Contente, et al., "Expression of Gene rrg Is Associated with Reversion of NIH 3T3 Transformed by LTR–c–H–ras", *Science*, vol. 249, pp. 769–798.

Hajnal, et al., "Up–Regulation of Lysyl Oxidase in Spontaneous Revertants of H–ras–transformed Rat Fibroblasts", pp. 4670–4675.

Thompson, et al., "Caveolin–1, a metastasis–related gene that promotes cell survival in prostate cancer", Apoptosis, vol. 4, No. 4, pp. 233–237 (1999).

Thompson, et al., "Caveolin–1: a complex and provocative therapeutic target in prostate cancer and potentially other malignancies", Emerging Therapeutic Targets 3(2) pp. 337–346 (1999).

Tan, et al., "Identification of the Lysyl Oxidase Gene as a Target of the Antioncogenic Transcription Factor, IRF–1, and Its Possible Role in Tumor Suppression", pp. 2417–2421.

Kuivaniemi, et al., "Deficient production of olysyl oxidase in cultures of malignantly transformed human cells", *FEBS Letters*, vol. 195, No. 1, 2, pp. 261–264 (Jan. 1986).

Vater, et al., "Native Cross–Links in Collagen Fibrils Induce Resistance to Human Synovial Collagenase", *Biochem J.*, vol. 181, pp. 639–645 (1979).

Hämäläinen, et al., "Quantitative Polymerase Chain Reaction of Lysyl Oxidase mRNA in Malignantly Transformed Human Cell Lines Demonstrates That Their Low Lysyl Oxidase Activity Is Due to Low Quantities of Its mRNA and Low Levels of Transcription of the Respective Gene", *The Journal of Biological Chemistry*, vol. 270, No. 37, pp. 21590–21593 (Sep. 15, 1995).

Peyrol, et al., "Lysyl Oxidase Gene Expression in the Stromal Reaction to in Situ and Invasive Ductal Breast Carcinoma", *American Journal of Pathology*, vol. 150, No. 2, pp. 497–507 (Feb. 1997).

Thompson, et al., "Exogenous Leukocyte and Endogenous Elastases Can Mediate Mitogenic Activity in Pulmonary Artery Smooth Muscle Cells by Release of Extracellular Matrix–Bound Basic Fibroblast Growth Factor", *Journal of Cellular Physiology*, vol. 166, pp. 495–505 (1996).

Sehgal, et al., "Transforming Growth Factor β1 Stimulates Contrasting Responses in Metastatic versus Primary Mouse Prostate Cancer–derived Cell Lines in Vito", *Cancer Research*, vol. 56, pp. 3359–3365 (Jul. 15, 1996).

Shimura, et al. Abstract; American Urological Association 94th Annual Meeting, Dallas, TX, "Reduction in Lysyl Oxidase Expression is an Preditor of Recurrence Following Radical Prostatectomy", May 1–6, 1999.

Thompson, "Metastasis–related Genes in Prostate Cancer: The Role of Caveolin–1", *Cancer and Metastasis Reviews*, vol. 17, pp. 439–442, 1999.

Guarini, et al., "Transfer of the Interleukin–2 Gene into Human Cancer Cells Induces Specific Antitumor Recognition and Restores the Expression of CD3/T–Cell Receptor Associated Signal Transduction Molecules", *Blood*, vol. 89, No. 1, pp. 212–218 (Jan. 1, 1997).

Jourdan–Le Saux, et al., "Functional Analysis of the Lysyl Oxidase Promoter in Myofibroblast–Like Clones of 3T6 Fibroblast", Journal of Cellular Biochemistry 64: 328–341, Feb. 1997.

*Proceedings of the American Association for Cancer Research*, vol. 36, p. 266 #1589 Mar. 1995.

Liang, Peng, et al., "Differential Display of Eukaryotic Messenger RNA by Means of the Polymerase Chain Reaction", *Science*, vol. 257, pp. 967–971. Aug. 14, 1992.

Wood, David P., Jr., et al., "Sensitivity of Immunohistochemistry and Polymerase Chain Reaction in Detecting Prostate Cancer Cells in Bone Marrow", *The Journal of Histochemistry and Cytochemistry*, vol. 42, No. 4, pp. 505–511. 1994.

Gudas, "Retinoids, Retinoid–responsive Genes, Cell Differentiation, and Cancer", *Cell Growth & Differentiation*, vol. 3, pp. 655–662, Sep. 1992.

Mokulis, et al., "Screening for Prostate Cancer: Pros, Cons, and Reality", *Cancer Control*, pp. 15–21, Jan./Feb. 1995.

International Search Report, completed May 30, 1997.

CL-1#2

AATTTTTTTTTTCGACGGCCCAACGGAATTTTTTTTTTCGACGGCCCAACGGAATTTTT
TTTTTCGACGGCCCAACGGGAATTCGGCTTAGCTAAGGTCACCCAGACTTCATGGACT
TGTCTATTTTCTTGCCCAAAGGGATAGTTCCTCAGGTATTTGGGGACAGCATTCACCTC
TTGCAGGAGCTATGCCTGTGTGTTTGTGCTAAGTTGATACTTTCTGCGATGATCTCAC
(SEQ ID NO. 31)

CL-10#3

TACCATCGGAGAAAGAAGACCAAGCAAGGCTCAGGCAGCCACCGCCTGCTTCGCACT
GAGCCTCCTGACTCAGACTCAGAGTCCAGCACAGACGAAGAGGAATTTGGAGAATTG
GAAATCGCTCTCGTTTTGTCAAGGGAGACTATCCCGATGCTGCAAGATCTGCTGTCCCT
CTGGCCTTTGTCATCCTCGCGCCTGCGTTGTGGCCTCTGTGGGCTTGGTGTGGAGCAAA
TGGCTCTCAAGGAGGACTGAGTCTCAAGGAAATT (SEQ ID NO. 32)

CL-11A#5

AGCTAAGGTCAGGAGGTGTCTGAAGAATTGGCTGATGCATGGCAGGGATGTTGTTGAC
CTGCTTTTAGAACAATACTTCCATTTAATTATAGCATATCTTATGTGTGTATTAAAGCA
GAGCCGATCTGGTGGGGCTCATTAAGTAAATGTACTTACTGCAAAAGGTTCAACTGGT
GACCCCAGTTTTCCCCAGAAGCAATATGATAGGACAGAGGCGACTCCTGCAAGTTGTC
TCAGACTTCACACATACATTGTGACATTCTCTGAGCATGTGCACTGTACATGATATGAC
ACTATCAA (SEQ ID NO. 33)

CL-11C#2

AGCTAAGGTCCACTACCTTGTGAAGATGTATAAACACCTGAAATGTAGAAGCGATCCG
TATGTCAAGATCGAGGGGAAGGACGCTGACGACTGGCTGTGTGTGGACTTTGGGAGTA
TGGTGATCCATTTGATGCTTCCAGAAACCAGAGAAACCTATGAATTAGAGAAACTATG
GACTCTACGTTCTTTTGATGACCTTAGCTAAGCCGAATCAGCACACTGGCGGCGTTACT
AGTGGATCGAGCTCGTACAGCTGATGCATAGCTTGAGTATCTATAGGTTACTAATAGC
TGGCTATCATGTCAAGCGTTC (SEQ ID NO. 34)

FIG. 12A

CL-12#1

AGCTAAGGTCAAAATAAAAGCTCAAGATGACATCAGTCCCATTTGTCCTAAGTCCTGG
TGTTGTATGGATGGTAAGCAGCAGCCAATTATGGTGACAGGTGATAGATCCAATTTGT
TAACATTTCTCCATCTCTAAGCCATCCTTAAAGAAAATCATGAATGGAGTCACACCAT
CTTCACGGTAGTCCAGGAGAGCAACCATACCATCTGGATTCATGTTTCACCAATAAAA
ACTGGTAGTTATTGAATTAGCAAGGATGTGCTACTCTCTGCAGCTCAGC (SEQ ID NO. 35)

CL-13#1

AGCTAAGGTCTCATGCAATGGAACTTAATTCTTAGAACTGTAAGAATTACATCAAACA
TAAAAGCCTCCCTATTAATGTAGTCCACAAAACTGGCAGGTATATATGCCTTCTGAAT
TTGTCTCCAGTGACTTTGGTAAATCTAACTAAATTTTTAAAAATTCTTAATGAATTTAT
CGTCAACAACAACCACCTCTTGGAAAATTAACCCTTGCAGTGTCTGTGTTAGACTCAG
AAGTCAA (SEQ ID NO. 36)

CL-14#4

GAATTCGGCTTAGCTAAGGTCAGCGTGAAGTTTAAGCAGACATGAGTCTGAAACAGTC
TCATGACACATCTGATAGGATTTTTTAAGACTGCCTGGCTTAGTCTTACTGCTGTTAGT
GTATATTAGGTGTTGTACACATTATAAAGAAAATTATGTCTCATTATCTTGTTTAAGTC
AAGGAAAATAGAGAACTTTGGTCAAAT (SEQ ID NO. 37)

CL-2#2

GAATTCGGCTTAGCTAAGGTCAGCGTGAAGTTTAAGCAGACATGAGTCTGAAACAGTC
TCATGACACATCTGATAGGATTTTTTAAGACTGCCTGGCTTAGTCTTACTGCTGTTAGT
GTATATTAGGTGTTGTACACATTATAAAGAAAATTATGTCTCATTATCTTGTTTAAGTC
AAGGAAAATAGAGAACTT (SEQ ID NO. 38)

CL-2#3

GAATTCGGCTTAGCTAAGGTCAAAATACACGGATTGCAATCACTTTTCTAAACAAAAG
AAACAAAGTAACTGCTGAGGTTAGCAAAGATGAGTTCTCGTCATACTGCCTTGTACTG

FIG. 12B

TTTTGTGAACTGTGTTATTAAAAATCTGAGCTTAACAAAATCTTTACAAGTCACCTCAT
GAAAACAGCATTTGGCCAATAAGAGTTTAATTCCACACCAGTGAGACCTTAGCCT
(SEQ ID NO. 39)

CL-2#4

GAATTCGGCTTTCTGCGATCCACTCTTTGAAGCTATTGGCAAGATATTCAGCAACATCC
GCATCAGCACGCAGAAAGAGATATGAGGGACATTTCAAGGATGAAAGGTTTTTTTCCC
CCCTTACTATTTCCTTGGTGCCAATTCCAAGTTGCTCTCGCAGCAGCAAATTTATGAAT
GGTTTGTCTTGATCAAGAACAAAGAATTCATTCCCACCATTCTCATATATACTACTTTC
TCTTCTT (SEQ ID NO. 40)

CL-3#1

GAATTCGGCTTTCTGCGATCCACTCTTTGAAGCTATTGGCAAGATATTCAGCAACATCC
GCATCAGCACGCAGAAAGAGATATGAGGGACATTTCAAGGATGAAAGGTTTTTTTCCC
CCCTTACTATTTCCTTGGTGCCAATTCCAAGTTGCTCTCGCAGCAGCAAATTTATGAAT
GGTTTGTCTTGATCAAGAACAAAGAATTCATTCCACCATTCTCATATATCTACGTCTCT
TCTAG (SEQ ID NO. 41)

CL-4#1

GAATTCGGCTTTCTGCGATCCTAGAGCAGGTAAGTGAAGAAGGCCAGTAAGTTTTAAG
GATGGCCTTGTTGCCTTCTATCAAGTTCTCTGGGACTTTGTAATTTTGATTACTACTATT
GATACATGGTTATGGTCAGAAGGCCTCTTCTCCCTT (SEQ ID NO. 42)

CL-4#2

AGCTAAGGTCCGGACTCTATGGCATGACCCCAAAAACATTGGCTGGAAAGATTACACT
GCCTACAGGTGGCACCTGATTCACAGGCCTAAGACAGGCTACATGAGAGTCTTAGTGC
ATGAAGGAAAGCAAGTCATGGCTGACTCAGGACCAATTTATGACCAAACCTACGCTG
GTGGACGGCTGGGCTGTTTGTCTTCTCCAAGAGATGGTCTATTCTCGGACCTCAAGTAT
GAGTGCAGAGATGCTAGAGAGCAGGCTCAGTCTCAGCA
(SEQ ID NO. 43)

FIG. 12C

CL-5A#4

TGACCATCGAGTGCATCAGCCTCATCGGGCTGGCCGTCGGGAAGGAGAAATTCATGCA
GGATGCTTCAGATGTGATGCAGCTATTGTTGAAGACACAGACAGACTTCAATGATATG
GAAGATGACGACCCCCAGATTTCTTACATGATCTCAGCATGGGCCAGGATGTGCAAAA
TCTTGGGAAAGAATTCCAGCAGTACCTTCCCGTGGTTATGGGGCCGCTGATGAAGACT
GCTTCAATTAAGTCCTGAGTGCCTCTAGACACCAGGACATGAGATATGAGGTA (SEQ ID NO. 44)

CL-6#2

TGACCATCGTGTAGTTGGTGTGCTTGTTGTCGAAGATGAGGGCCTCCTGGATGAGCTG
GTGCTGCTGCTCCAGCAGGTCCAGGCTGGGCTTGTAGTCCACGATGCTGCGCTCGTAC
TGCTTCAGGTGGCTCAGCTGGTCTTCCAGAGTCCCGTTCATCTCAATGGAGATGCGCCC
GATCTCCTCCATCTTAGTCTGGATCCACGGCCCCACCATATTGGCTTGGCTGGCGAACT
GTCGGCGAAGGCTGCATTGGATTGCT (SEQ ID NO. 45)

CL-7#4

TGACCATCGAACACCCCAACACTCTCCACTACCTGCCATTTCTTCCAGCCTTATCCACA
CCACCCCGTTTCTCCTGAAGACTGATTTGCTTAGCAACTGCACTGAGCCAACCCTGAA
GACACATGATTATTGGTTGGGCTCCATTAAACAACAAGCCTAGTGCTTGGGAAGGGGG
GTGGGGAGGGGAAGAGACGTGAGAAGCATGTTGGCGTAGACCTTGAGGCATGGATGA
AGCATCTGCCGGCCTGACCTGGTACAGGTGGCATCTGCACTGCAGCAAGGC (SEQ ID NO. 46)

FIG. 12D

CL-8#2

TGACCATCGAAGTGCAAAGGAAATGACTTGATTTCATGAAGTATCTCCAGAAGTAACG
CTTTGTTTTCTGCATCCTGAACTTTATTCCCAGTGAAGAGCTGAAAATCTGGACGCTCA
AAAAATGGAAGCACTTTGGAGAGAGCCCTTAACTCTATCAGGTACAGGAAGTACAAG
TTCCTCAGCCTTCGTGGGCCTTCTCCTTCAGTCAGAATCCATCAAAGGTGCTGGAACTC
TGTGACATTGTGACCCATTCTTTCAGCCAGTATCTGTAAGATAC (SEQ ID NO. 47)

CL-9#1

GGGAACGAATGATCTGGAACTGTGGCTTGTAGACAACCCAAATATCTTAGGTAGGTAA
GAAATTCCAGCATCACACTATATAGGAAATACTGTGCGAAACTGACAGTTAACTGTGC
ACAAAGTTCAATGGCTTCAAAATAATGTATAAAGGATAAGAAGAAACCAGTTTACCAT
TTTGGT ATTATTTTGGTTGCTTTGTATAACTTCAATAATTT (SEQ ID NO. 48)

CL-54A#2.-SP

GGGAACGAATGATCTGGAACTGTGGCTTGTAGACAACCCAAATATCTTAGGTAGGTAA
GAAATTCCAGCATCACACTATATAGGAAATACTGTGCGAAACTGACAGTTAACTGTGC
ACAAAGTTCAATGGCTTCAAAATAATGTATAAAGGATAAGAAGAAACCAGTTTACCAT
TTTGGTATTATTTTGGTTGCTTTGTATAACTTCAATAATTT (SEQ ID NO. 49)

CL-54A#2.-S0

GACGTAAGCC (SEQ ID NO. 50)

CCACAAAGCAAGCTTCTGTCTGGAGTACAGCTCCTGTGACTATGGGTACCACAGGGCC
TTTGCGTGCACTGCACACACACAGGGATTGAGTCCTGGATGTTATGACACCTATGCGG
CAGACATAGACTGCCAGTGGATTGATATTACAGATGTACAACCTGGAAACTACATTCT
AAAGGTCAGTGTAAA (SEQ ID NO. 51)

FIG. 12E

CTATCAATGAAGGGGGAGATCACTGGGTAAGTTCGAATGCCCTCAGGCAAGGTGGCC
CAGCCTTCCATTACTGAATTCAAAGATGGCACTGTTACTGTACGTTACTCACCCAGTGA
AGCTGGCCTGCATGAAATGGACATTCGCTATGACAATATGCATATCCCAGGAAGCCCT
CTGCAGTTCTATGTTGATTATGTCAACTGTGGCCACATCACTGCTTATGGTCC (SEQ ID NO. 52)

TTAGCACCTCGACCACGAAATGAGGAAGATGCAACAGACGTGGTGGGCCTGGCTCAG
GCTGTAAACGCTCGGTCCCCACCTTCAGTAAAACAGAACAGCTTGGATGAAGACCTTA
TTCGGAAGCTAGCTTATGTTGCTGCTGGGGACCTGGCACCCATAAATGCTTTCATTGG
GGGCCTTGCTGCCCAGGAAGTCATGAAGGCCTGCTCTGGAAAGTTTATGCCCATCATG
CAGTGGTTGTACTTTGATGCTCTTGAATGTCTCCCAGAACGGACAAAGAGGCTCTGAC
AGAGGAGAGTGCCTCCCACGTCAGAACCGTTACGATGGGCAGGTAGCTGTATTGGTCA
GACTTCAGGAGAAGCTGAGAAGCAAA (SEQ ID NO. 53)

TTAGCACCTCCAATGGCTGGGTACCAGCCAGCCGCAATGTCCGCTCCACAAATTTGGA
GTCTGTGAGGTACTGATTAACATTTTCTGCTGGCTGCTTGAAAAGGCCTTCAAATTCAT
CCCGGGCCCACTGAAGAGTGTGTTCGATGGCATTGGGAAAGTTTTTCAGGGTACAAAT
GGGGATGGATTTCTCTGGTGGATCCTGGCTAGACGTGATGGATTCTGTCAGGAAGGGG
ATTACCACCTGCACGTTGCCCTTT (SEQ ID NO. 54)

TTAGCACCTCACACTCACATGCCCTTCTACATAGAGACTGGTTAAACAGCCCTCCCTCC
CTTGTCCCGACTTGACTTCCAGGCCCCTCTGCTTTCCTCTCACAACCACACCAGGTCTG
ATGGAGTCCAGTGCCTGCAGTGACCCAACATAGACTGCACTTTCACCTACCTACTGGA
TGGTCCTGCAGCCCAGACGGCTGCTCTTCTTTCTCATGGAGTTTCTCTCCTGCCTGAGA
TATGCTATCTGGTCTGCCCCTGTGTAGCTCCCATGGGATCCCTTAAAATCGATCCTTTT
TTAA (SEQ ID NO. 55)

FIG. 12F

TTAGCACCTCGTGAGGAGACTGTTGTCCACAGGCCAGCTAGTGGTACCCTACTGAGAA
GTTGGGTTTTGGTTTTGTTTCCCTTGAAGGGTCGCTGTTAGAGGATGGAAGTAACTTCT
AATTCTTGATCTGTTTGTTGGTCTTGTTTTCAGTACTTTTTGCCAGTTGTATACACTTGG
AGAGGGAATTTGTATGCCTGTAATCTTGTTCTTGAGGTCAGAAATTCAAAACATTGGG
AGCTTTTGTTGTAAAGGTTAAACTGTGAATCCATATAGCAAATGCAGATCCTTTTACA
GTGTAAACCACATTTCCTGCCTCAGCCTAAAGCACTGGTCATTT (SEQ ID NO. 56)

ACCTGCATGCCTAAAGGAGTAGGCTTAGGGGTGGGGAGAGAGAAGGCATAGGCTTTT
CTAGTTATACAAAGCTGTGTAAGGCAAGGTTCCTTTCTACTAAATGGTCAGCTGTCACT
ACATTTATACTTTTGTATGTCATAAACCCTTTCTTTCATTCCTCCCTGGGTAACCAGGA
CAATCGGAGGGCAGTGTGTTACTGGGATTAGAGGACTAGCAATACTGGGTAACCCGCC
TAAGCTGGAAGGTGACGTAATACGTTTCTTTAAAGATTCAGTCAGTCAAGCAGTTTAG
CAATATCAAAATGTCTGGCTGTTTGGTCCAGTGTACACTGTT (SEQ ID NO. 57)

GCTATCTGCGAAACTACAGAAAGGAAGACAGCTTGGCCCAGCGCGGTGAAGTTCAGA
ATTCACTAGGTAGTTGTTGTTGGTTGACTTGGAGGTAGCTGGGTAATCAACAGCTTTCA
CTTTAGATTCAATGTGAACCGCAGAGTTACTCATGACCAAGAGTCTGGCAAACTCATT
AATGCTGTTTAATACTTGTTTGATATTTTTTCACCTTTTGAGCCCTTTTCCCAAAGAATT
CAATATCAGTTTAGTAGCAACAGTACAGTTGCCATTTAAATTGGTTTAGTTGCAGTATA
GCA (SEQ ID NO. 58)

GCTATCTGCGAAACTACAGAAAGGAAGACAGCTTGGCCCAGCGCGGTGAAGTTCAGA
ATTCACTAGGTAGTTGTTGTTGGTTGACTTGGAGGTAGCTGGGTAATCAACAGCTTTCA
CTTTAGATTCAATGTGAACCGCAGAGTTACTCATGACCAAGAGTCTGGCAAACTCATT
AATGCTGTTTAATACTTGTTTGATATTTTTTCACCTTTTGAGCCCTTTTCCCAAAGAATT

FIG. 12G

CAATATCAGTTTAGTAGCAACAGTACAGTTGCCATTTAAATTGGTTTAGTTGCAGTATA
GCA (SEQ ID NO. 59)

GCTATACTGCAACTAAACCAATTTAAATGGCAACTGTACTGTTGCTACTAAACTGATA
TTGAATTCTTTGGGAAAAGGGCTCAAAAGGTGAAAAAATATCAAACAAGTATTAAAC
AGCATTAATGAGTTTGCCAGACTCTTGGTCATGAGTAACTCTGCGGTTCACATTGAATC
TAAAGTGAAAGCTGTTGATTACCCAGCTACCTCCAAGTCAACCAACAACAACTACCTA
GTGAATTCTGAACTTCACCGCGCTGGGCCAAGCTGTCTTCC
(SEQ ID NO. 60)

GCTATACTGCCCACCACATTGCCACACTCGGAATGACATTTCTATATTTTCACCTCCCC
AGATTTCCATTTCTTCATCGTAACTTCCAATGTGCTCAAAATATTTTTTAGATATAGAA
AAAAGGCCTCCTGCAAAGGTGGGGGTCTTAATTGGGTAGGTTTCATCTTTCCTTCTTTG
CTTCTCATGATCAGGAAGTGACTCCCAGCCAAAGGAAAGGCTCCAGTCAAAATTTCCA
CGGTTATGGTTGCTTCCGTACGGAGAAGGCTTGTTGAATTCAAATGTGTTTAGATCTAT
GGATGCGATGTCTGGACTCACCACGGCA
(SEQ ID NO. 61)

GCTATACTGCTGAAGGAGATCATTTTGGTGGATGATGCTAGTGTAGACGACTACCTGC
ATGAAAAGCTGGAGGAATACATAAAACAGTTTTCTATTGTGAAAATAGTCAGGCAGC
AAGAAAGGAAAGGCCTGATCACCGCGCGGTTGCTAGGGGCAGCTGTAGCAACTGCCG
AGACGCTCACGTTCTTAGATGCTCACTGTGAGTGCTTCTATGGCTGGCTGGAACCTCTG
CTGGCCAGGATAGCTGAGAACTACACTGCCG (SEQ ID NO. 62)

AGTTGCCAGGGGGCAGCTCACGGCGCAGCTCATCCTCTGTGATGTAATTCTTATCTCC
AGCCAGGATCTTGAAGGAAGCCATGACCTGATCTGCAGTATCAGTATCTGCCGTCTCT

FIG. 12H

CGGGACATAAAGTCGATGAAGGCCTGGAACGTCACTACCCCCAAGCGGTTGGGGTCT
ACAATGCTCATGATTCGGGCAAACTCTGCCTCTCCCATGTTGTAACCCATGGAGATAA
GGCAGGCGCGGAAATCGTCTGTGTCCATCATGCCCGTCTTCTTCCGGTCAAAGTGGTT
GAAAGA (SEQ ID NO. 63)

AAGCCGTGTCGCTGAACTGGGAGGACACACTGCTCACCCTAGAAGGCTCTGGCTGACC
CTCCGCCCGGTTAAACAGGGACTTTGTGGCCATGTGCTGGCGACACAGGTCCTGGTAC
TCAAAAGTAGTGTCACCATGGGCCCCCTCCGGCCCCAGCGCTGCCAGGCGTCCTTATC
CCGCTGTCTCGAATGATGGCGCATACCAAGGCCACTGAAAGCCACTAGCAGCCCAGCG
ACGCCTGCCAGGGCCACTAGAGTAAGCAGCACTGAGCGCATGGGAGATATGCCAT
(SEQ ID NO. 64)

AAGCCGTGTCTGGACGTCCGTGTGTCCGGCTCTTGCTCACGCAGTCATGGCCTCCGGA
ACGCGCAAATCGGAAAGTCGGCTCCTGACTTCACGGCCACAGCGGTGGTGGATGGTGC
CTTCAAGGAAATCAAGCTTTCGGACTACAGAGGGAAGTACGTTGTCCTCTTTTTCTACC
CACTGGACTTCACTTTTGTTTGCCCCACGGAGATCATCGCTTTTAGCGACCATGCTGAG
GACTTCCGAAAGCTAGGCTGCGAGGTGCTGGGAGTGTCTGTGGACTCTCAGTTCACCC
ACCTGGCGTGGATCAATACCCCACGGAAAGAGGGAGGCTT (SEQ ID NO. 65)

AAGCCGTGTCGGAGGGCACCAAGGCTGTCACCAAGTACACCAGCTCCAAGTGAGTGC
TCAAGACTCAGCTCTTAACCCAAAGGCTCTTTTCAGAGCCACTCAAGACTTCAAAATT
GGAGCTTTAATGCTGACTTAGTGACTACCGGGAAAATAACTGACTTCATCTGCAGGAT
TGTGTACAAACACTTATGGTTTAGTAAATCGAAAAGATAGACATTGCCCATCAGTTCT
GTCTGGTCCACTTAAATATGCTTTTTTCTTAGAAGTTCTAAGAACCCTGTCAATAACCT
ATCTAGGTCCAGTCCTTGAGTTCAAAGGCCAAATACCAATG (SEQ ID NO. 66)

FIG. 12I

CAACGCTCAGGATGTAAGCTGTTTCCAGCACCTGGTTCAAGCGAATGTAAGAAATAAG
AAGGTGTTGAAAGATGCCGTGAATAACATTACAGCAAAGGGGATCACAGATTACAAG
AAAGGCTTTAGCTTTGCCTTCGAACAGCTACTTAATTATAATGTTTCCAGAGCTAATTG
CAATAAGATTATCATGTTATTCACGGATGGAGGAGAAGAGAGAGCCCAGGAGATATT
TGCCAAATACAATAAAGACAAAAAAGTCCGTGTGTTTACATTTTCCGTCGGTCAACAT
AATTATGACAGAGGACCTATTCAGTGGATGGCTTGTGAAATAAAGGTTACTATTATGA
GATTCCTCCATT (SEQ ID NO. 67)

TCAACGCTCATCACACCAAGAATCAACTGGTTCTTCAAGTTTGTCTTATTTTCAGATTG
GCCAGTGACGTTGAAGACTGGTAGAGTTCCAGTAATGACAAGTCCCAGTTCCAGGGCA
TCCAAATACACATTTGTCCATTGAACTTGCTTCGCTTTGTCACCAGCTAAAACCATTGG
TCTTCCCAGAACATCTAGATATTCCTGAGTATTGATTCTTATTGCACCAATGGAGGGAA
TCTCATAATAGTAACCTTTATTTTCACAAGCCATCCACTGAATAGGTCTCTGTCATAAT
TATGTTGACCGACGGAAATGTAA (SEQ ID NO. 68)

TAACGCTCAGGAGAAGAATAGGAATGCAGAGAACTCTGCCACAGCCCCCACGCTCCC
GGGCAGCACCTCAGCCACCACCGCAACCACCACCCCTGCTGTAGATGAAAGCAAGCCT
TGGAACCAGTATCGCTTGCCTAAGACTCTTATACCTGACTCCTACCGGGTGATCTTGAG
ACCCTACCTCACCCCCAACAATCAGGGCCTGTACATCTTCCAAGGCAACAGTACTGTT
CGCTTTACCTGCAACCAGACCACGGATGTCATTATCATCCACAGCAAAAAGCTCAACT
ACACCCTCAAAGGAAACCACAGGGTGG (SEQ ID NO. 69)

CGAGTCAGACGGCTTCAGCATCGAGACCTGTAAGATCATGGTGGACATGCTGGATGAA
GATGGGAGTGGCAAGCTTGGCCTGAAGGAGTTCTACATCCTCTGGACGAAGATTCAGA
AATACCAAAAAATCTACCGGGAAATCGATGTGGACAGGTCTGGAACTATGAATTCCTA

FIG. 12J

CGAGATGCGGAAAGCACTGGAAGAAGCAGGTTTCAAGCTGCCCTGTCAACTCCATCA
AGTCATCGTTGCCCGGTTTGCAGACGACGAGCTAATCATCGACTTTGACAATTTTG
(SEQ ID NO. 70)

CGAGTCAGACAACCTGTTCAAGTGGGGTGGGGACCATCCACGGAGCAGCCGGCACCG
TATATGAAGACCTGAGGTACAAACTCTCCCTAGAGTTCCCCAGCGGCTACCCTTACAA
CGCACCCACAGTGAAGTTCCTCACACCCTGCTACCACCCCAACGTGGACACCCAGGGC
AACATCTGCCTGGACATCCTCAAGGATAAGTGGTCTGCACTATATGATGTCAGGACTA
TCTTGCTCTCTATCCAGAGCCTGCTAGGAGAACCCAACATCGATAGCCTTTGAACACA
CACGCTGCGGAACTCTGGAAAA (SEQ ID NO. 71)

TATGAGTCCGGAGCGACGGCTACGAGTGTGAACTGTTCCAGCCCCGAGCGACACACCA
GAAGTTATGACTACATGGAAGGAGGGGATATAAGGGTGAGAAGACTGTTCTGTCGCA
CCCAGTGGTACCTGAGGATTGACAAACGAGGCAAAGTGAAAGGGACCCAGGAGATGA
AGAACAGCTACAACATCATGGAAATCAGGACCGTGGCAGTTGGAATTGTGGCAATCA
AAGGGGTGGAAAGTGAATACTATCTTGCCATGAACAAGGAAGGGAAACTCTATGCAA
AGAAAGAATGCAATGAGGATTGCAACTTCAAAGAACTGATTCTGGAAAACCATTATA
ACACCTATG (SEQ ID NO. 72)

TATGAGTCCGAGGAGGAGCACAATGCTGGGAGTGTGGAAAGCCAGGTTGTCCCCAGC
ACACACCGAGTGACCGATTCCAAGTTCCATCCACTCCATGCCAAGATGGATGTCATCA
AAAAAGGCCACGCCAGGGACAGCCAGCGCTACAAAGTTGACTATGAGTCTCAAAGCA
CAGACACCCAGAACTTCTCCTCCGAGTCTAAGCGGGAGACAGAATACGGTCCCTGCCG
CAGAGAAATGGAGGACACACTGAATCATCTGAAGTTCCTCAATGTGCTGAGTCCAGAG
TCTCACATCCAAACTGTGACAAGAAGGGG
(SEQ ID NO. 73)

FIG. 12K

TCGCCCGGGACTTCATGCGATTGAGAAGATTGTCTACCAAATATAGAACAGAAAAGAT
TTATCCCACAGCCACTGGAGAAAAAGAAGAAAATGTTAAAAAGAACAGATATAAGGA
CATACTGCCATTTGATCACAGCCGAGTTAAGTTGACTTTGAAGACTCCATCCCAAGAT
TCAGATTATATCAATGCAAATTTTATTAAGGGTGTGTATGGGCCAAAAGCATATGTGG
CAACCCAAGGGCCTTT (SEQ ID NO. 74)

TGTGGAAAGCCAGGTTGTCCCCAGCACACACCGAGTGACCGATTCCAAGTTCCATCCA
CTCCATGCCAAGATGGATGTCATCAAAAAAGGCCACGCCAGGGACAGCCAGCGCTAC
AAAGTTGACTATGAGTCTCAAAGCACAGACACCCAGAACTTCTCCTCCGAGTCTAAGC
GGGAGACAGAATACGGTCCCTGCCGCAGAGAAATGGAGGACACACTGAATCATCTGA
AGTTCCTCAATGTGCTGAGTCCAGAG (SEQ ID NO. 75)

TGACCATCGAAGTGCAAAGGAAATGACTTGATTTCATGAAGTATCTCCAGAAGTAACG
CTTTGTTTTCTGCATCCTGAACTTTATTCCCAGTGAAGAGCTGAAAATCTGGACGCTCA
AAAAATGGAAGCACTTTGGAGAGAGCCCTTAACTCTATCAGGTACAGGAAGTACAAG
TTCCTCAGCCTTCGTGGGCCTTCTCCTTCAGTCAGAATCCCATCAAAGCGCTGCTGGAA
CTCTGTGACATTGTGACCCCATTTCTTTTCCAGCCAAGTATCTTGTAAAAGATACCTTG
CACTCAAATGCACATTAATGCTTGCGTGCAGGCCAGATATAAGTCTGTAGAATCGCTC
TTTCTACACAGAGGCCTTCTAGCCAGTTGTAAA (SEQ ID NO. 76)

CTGCTTGATGCTAAGCCCGGCAGCCTGTGTTTCATCTACAGGATGCACAACATAAAAG
AAAAGATCTGATTCCCGCAGGTTCTCTTCTGACCTACACACACACACACTAAAATAAC
ATTTAAAAATATGTGCCAAATTATATTTGTTCGGGTGCCACCTTCCACCAGCTTACCAC
TACGGTAGAACTGTCAAATTCATCTCCCTGAATTTGTCTTAAAGGGGTGTCCATGCAC
AGGCCCAAGAGTCACCTCCAATGAAATAAATGTAATACTGAAGTATGCCATGATGTTT

FIG. 12L

GTTGTTTTCTTTCATCGTAAGCCTGTAAGCAGGAAAAATAGTAATAGATAGAATAGAG
ACTTACCAGTGGTCGATGGCCTGGTCAGTCTGTGCGGTGACTAGGACCAGG (SEQ ID NO. 77)

ACCTGCATGCCGAGTGTGACGCCTTTGAGGAGAAGATCCAGGCTGCCGGAGGGATCG
AACTCTTTGTCGGAGGCATTGGCCCCGATGGACACATTGCCTTCAATGAGCCAGGCTC
CAGCCTGGTGTCCAGGACCCGTGTGAAGACTCTGGTTATGGACACCATCCTGGCCAAC
GCTAGGTTCTTTGATGGTGATCTTGCCAAGGTGCCCACCATGGCCCTGACAGTGGGTG
TCGGCACTGTCATGGATGCTAAAGAGGTGATGATCCTCATCACAGGCGCTCACAAGGC
CTTTGCTCTGTACAAAGCCATCGATGGAGGCGTGAACCACATGTGGACGGTGTG (SEQ ID NO. 78)

GCTATACTGCAATGTTAGGGGAATGAACGCGTTTTCCTACTGCACTGGGGACTTTTAG
ATAGGTTAATGAAAGGCCTTTTATTCTGTTACTGGACACGAAAACTTTGTCTAATTTCT
TATACTCTATTGTACGTTTACAGTCGCAGCACTAAAATGGAAGACATCAAACATTTTT
AACAGAAAAAAAAAAAAGATGTAAAAACTAACTAAGGACTATTTATTGATAATGTTTTG
CTACTCCTGTCAGACAATGGCTATAAACTGAATTAGGCAGTCTTAAAAAAAAAAAAAG
AAAAAAAAGAAAAAAGAAAAAAAGAAAAGAAAAGAAAAAAAACTGG (SEQ ID NO. 79)

AGCTAAGGTCGGGTACTCTGATACTTCAGAGTTTAAAATCATCAGCCCTTGTAGATCT
ATTCCTAAATCTTATGAAAATGCTCAGATGTTTACACAGCTGTGAAACAGGGTCAGTT
CAGATCGCTGATGGCTTGAGAATGTGTTTCTTGTTGACATCAGGAACTGGAAATGTTT
ACTTCCCGTCATTTATGAGTCATCAAGTATCTCGGCTCTTTTAAGAGCGCAAGATAAA
ACAAGCTTAAACCAGGTGATAAGAGCAGAGTCCACTTGAGTCTGAGCTCACCCGAGA
ACTTGCTATCGAGGACATTTGGAATGGGAGTGTGCAGGCTTCCTTCAGTTACTGAATG
AGTCCATCTGCTAGTCACCTTGAC (SEQ ID NO. 80)

FIG. 12M

AGCTAAGGTCCAGGGGGCAAAGCGGTGACGTGTGCACATCGATATGAGAAACGGCAG
CACGTCAACACGAAGCAGGAGTCGCGGGATATCTTTGGAAGATGTTATGTCCTAAGTC
AGAATCTCAGAATTGAAGATGATATGGACGGAGGAGACTGGAGTTTCTGCGATGGCC
GGTTGAGAGGCCATGAAAAGTTTGGCTCCTGTCAGCAAGGAGTAGCGGCTACTTTCAC
TAAGGACTTTCATTACATTGTTTTTGGAGCCCCAGGGACTTACAACTGGAAAGGGATC
GTCGTGTAGAACAAAAGAATAACACTTTTTT (SEQ ID NO. 81)

AAGCCGTGTCTGTGCTCAAGGAAGAAACCCACTGGACCAACTTCTGTCAGAAAGGAA
AACCTTGTTCAAAGTTTCAGGACCCTGTTCTTTGCTTATTTGCACATGGTCACCTTGGT
CTGAGCTAGCCACCATTGTCACCCACAGCTGCAAAGAAAGCAGACCTTAGGAAACACT
GTCACGGCTGAGTGTGACTGCCTTGTTCATCCCCTGGACTGGTACTGTGTTGCCTGCAG
TACCATTGGGATCCCATAGCAAGAGAGGGAGAGGGAGATGTTAGTTAGCCTTTGCTAC
GAACCAAGCTGTCCCAAGTCTCAACAGCTAAACAGGTATTCATTTACCATGATTCTAT
GGTTAGCTAAGCTCTTGAG (SEQ ID NO. 82)

CTTTCTACCCTGGAGGATGTGCTTGAGGCACACTGCTCCTGTGCTCTCCACTTGAGGCA
TAAGCCCAGTCAGTTGTGCATAGATGATTAACCTCTGACCCCTAAAGATGGTAAGTTG
CTCTGGAGAAAGCATTTTAACAGACAAACCAGGAGGCAAATCCCAACTTAGAGAGAT
GTTATCCACTGCACACTGTAGAGCAAACTTGAGAGACCCAAGAGCCTTGGTCTGCATC
CTGTCCTTGCCTGTGATAAACACTCGAGTACCCCCTGATACCGGGCGATATTTTTGATT
AACTGGTCGAGGCTCCTTGTCCAATTCCAAAAGAGAACATCTGTGTTTC (SEQ ID NO. 83)

FIG. 12N

TGGTAAAGGGCATCTGTAAATACACTCTATGAGGAAATTAAAACTTGAACATGGCAGT
CTGACATTGCAAAACAAAACAAAACAAAACTGACCCTCCAATAGCAGCGAAAACAAC
GTGAAAGATACAAAGCAATGAGAATCTGGTTCTGAACGCCTGGGATCCTGGGAGTCAT
CGGTAGCAGCGCCATGAGAGGAGCCGTGGCCTGTCCCATGTGGTCCCACCTTCACCTC
TTCCCTCACATCCCTCTTAAG (SEQ ID NO. 84)

TGGTAAAGGGGGCAAGGGCAAAGGCACGGGAGACAGAGGCCACTGCATCTGTACCCA
CATCAGACATGTTTGTCCATTTTCTCTCATTTGGCCTTAGACCATTGGCAAGAGTAAAT
GCTCTTAGTCCCGTTATCTAGAAATTTCTTCCTTTGGGGAGAACCACTTATAGACAATA
TCAGCTCTCTACAAATAACACGAAAGGTCGTAACAC
AGCAAGTGACCAGAAAGTGCCCGTCCTTGCGGCTCTGATCCACGTGGCTCTCCGTAGA
CAAATTGTTTTTTCTTGTAGGGATATCTGTTTTGCTTCTGAACTTTCTTACAAGTGTTTG
GGACTCTTCGGGTGGCGTT (SEQ ID NO. 85)

TGGTAAAGGGTCAAGTGTTCGATCAGAGTGGAGCTCCATTACCGAATGTAATCGTGGA
AGTCCAAGACAGAAAGCATATCTGCCCGTTTAGAACCAACAAGCTTGGAGAATACTAT
CTGCTTCTGCTGCCCGGGTCCTACGTGATCAATGTTACAGTCCCTGGACACGACTCCTA
CCTCACGAAGCTTACTATTCCAGGGAAATCCCAGCCCTTCAGTGCTCTTAAAAAGGAT
TTTCACCTCCCGCTGCGATGGCAGCCGGATTCCATCTCCGTATCCAATCCTTCGTGCCG
ATGATTCCGCTGTACAAATTCATGCCAAGCCACTCGGCTGCCACAAAGCCTAGTCTGG
G (SEQ ID NO. 86)

GAATTCGGCTTTCTGCGATCCACTCTTTGAAGCTATTGGCAAGATATTCAGCAACATCC
GCATCAGCACGCAGAAAGAGATATGAGGGACATTTCAAGGATGAAAGGTTTTTTTCCC
CCCTTACTATTTCCTTGGTGCCAATTCCAAGTTGCTCTCGCAGCAGCAAATTTATGAAT

FIG. 12O

GGTTTGTCTTGATCAAGAACAAAGAATTCATTCCCACCATTCTCATATATACTACTTTC
TCTTCTT (SEQ ID NO. 87)

GAATTCGGCTTTCTGCGATCCACTCTTTGAAGCTATTGGCAAGATATTCAGCAACATCC
GCATCAGCACGCAGAAAGAGATATGAGGGACATTTCAAGGATGAAAGGTTTTTTTCCC
CCCTTACTATTTCCTTGGTGCCAATTCCAAGTTGCTCTCGCAGCAGCAAATTTATGAAT
GGTTTGTCTTGATCAAGAACAAAGAATTCATTCCACCATTCTCATATATCTACGTCTCT
TCTAG (SEQ ID NO. 88)

ACGAGGGGAAACCTCCTCAGAGCCTGCAGCCAGCCACGCGCCAGCATGTCTGGGGGC
AAATACGTAGACTCCGAGGGACATCTCTACACTGTTCCCATCCGGGAACAGGGCAACA
TCTACAAGCCCAACAACAAGGCCATGGCAGACGAGGTGACTGAGAAGCAAGTGTATG
ACGCGCACACCAAGGAGATTGACCTGGTCAACCGCGACCCCAAGCATCTCAACGACG
ACGTGGTCAAGATTGACTTTGAAGATGTGATTGCAGAACCAGAAGGGACACACAGTTT
CGACGGCATCTGGAAGGCCAGCTTCACCACCTTCACTGTGACAAAATATTGGTTTTAC
CGCTTGTTGTCTACGATCTTCGGCATCCCAATGGCACTCATCTGGGGCATTTACTTTGC
CATTCTCTCCTTCCTGCACATCTGGGCGGTTGTACCGTGCATCAAGAGCTTCCTGATTG
AGATTCAGTGCATCAGCCGCGTCTACTCCATCTACGTCCATACCTTCTGCGATCCACTC
TTTGAAGCTATTGGCAAGATATTCAGCAACATCCGCATCAGCACGCAGAAAGAGATAT
GAGGGACATTTCAAGGATGAAAGGTTTTTTTCCCCCCTTACTATTTCCTTGGTGCCAAT
TCCAAGTTGCTCTCGCAGCAGCAAATTTATGAATGGTTTGTCTTGATC (SEQ ID NO. 89)

MECLYYFLGFLLLAARLPLDAAKRFHDVLGNERPSAYMREHNQLNGWSSDENDWNEKL
YPVWKRGDMRWKNSWKGGRVQAVLTSDSPALVGSNITFAVNLIF
PRCQKEDANGNIVYEKNCRNEAGLSADPYVYNWTAWSEDSDGENGTGQSHHNVFPDGK

FIG. 12P

PFPHHPGWRRWNFIYVFHTLGQYFQKLGRCSVRVSVNTANVTLGPQLMEVTVYRRHGRA
YVPIAQVKDVYVVTDQIPVFVTMFQKNDRNSSDETFLKDLPIMFDVLIHDPSHFLNYSTIN
YKWSFGDNTGLFVSTNHTVNHTYVLNGTFSLNLTVKAAAPGPCPPPPPPPRPSKPTPSLGP
AGDNPLELSRIPDENCQINRYGHFQATITIVEGILEVNIIQMTDVLMPVPWPESSLIDFVVTC
QGSIPTEVCTIISDPTCEITQNTVCSPVDVDEMCLLTVRRTFNGSGTYCVNLTLGDDTSLAL
TSTLISVPDRDPASPLRMANSALISVGCLAIFVTVISLLVYKKHKEYNPIENSPGNVVRSKGL
SVFLNRAKAVFFPGNQEKDPLLKNQEFKGVS (SEQ ID NO. 90)

1 CAGATGCCAG AAGAACACTG TTGCTCTTGG TGGACGGGCC CAGAGGAATT
CAGAGTTAAA
61 CCTTGAGTGC CTGCGTCCGT GAGAATTCAG CATGGAATGT CTCTACTATT
TCCTGGGATT
121 TCTGCTCCTG GCTGCAAGAT TGCCACTTGA TGCCGCCAAA CGATTTCATG
ATGTGCTGGG
181 CAATGAAAGA CCTTCTGCTT ACATGAGGGA GCACAATCAA TTAAATGGCT
GGTCTTCTGA
241 TGAAAATGAC TGGAATGAAA AACTCTACCC AGTGTGGAAG CGGGGAGACA
TGAGGTGGAA
301 AAACTCCTGG AAGGGAGGCC GTGTGCAGGC GGTCCTGACC AGTGACTCAC
CAGCCCTCGT
361 GGGCTCAAAT ATAACATTTG CGGTGAACCT GATATTCCCT AGATGCCAAA
AGGAAGATGC
421 CAATGGCAAC ATAGTCTATG AGAAGAACTG CAGAAATGAG GCTGGTTTAT
CTGCTGATCC
481 ATATGTTTAC AACTGGACAG CATGGTCAGA GGACAGTGAC GGGGAAAATG
GCACCGGCCA
541 AAGCCATCAT AACGTCTTCC CTGATGGGAA ACCTTTTCCT CACCACCCCG
GATGGAGAAG

FIG. 12Q

601 ATGGAATTTC ATCTACGTCT TCCACACACT TGGTCAGTAT TTCCAGAAAT TGGGACGATG

661 TTCAGTGAGA GTTTCTGTGA ACACAGCCAA TGTGACACTT GGGCCTCAAC TCATGGAAGT

721 GACTGTCTAC AGAAGACATG GACGGGCATA TGTTCCCATC GCACAAGTGA AAGATGTGTA

781 CGTGGTAACA GATCAGATTC CTGTGTTTGT GACTATGTTC CAGAAGAACG ATCGAAATTC

841 ATCCGACGAA ACCTTCCTCA AAGATCTCCC CATTATGTTT GATGTCCTGA TTCATGATCC

901 TAGCCACTTC CTCAATTATT CTACCATTAA CTACAAGTGG AGCTTCGGGG ATAATACTGG

961 CCTGTTTGTT TCCACCAATC ATACTGTGAA TCACACGTAT GTGCTCAATG GAACCTTCAG

1021 CCTTAACCTC ACTGTGAAAG CTGCAGCACC AGGACCTTGT CCGCCACCGC CACCACCACC

1081 CAGACCTTCA AAACCCACCC CTTCTTTAGG ACCTGCTGGT GACAACCCCC TGGAGCTGAG

1141 TAGGATTCCT GATGAAAACT GCCAGATTAA CAGATATGGC CACTTTCAAG CCACCATCAC

1201 AATTGTAGAG GGAATCTTAG AGGTTAACAT CATCCAGATG ACAGACGTCC TGATGCCGGT

1261 GCCATGGCCT GAAAGCTCCC TAATAGACTT TGTCGTGACC TGCCAAGGGA GCATTCCCAC

1321 GGAGGTCTGT ACCATCATTT CTGACCCCAC CTGCGAGATC ACCCAGAACA CAGTCTGCAG

1381 CCCTGTGGAT GTGGATGAGA TGTGTCTGCT GACTGTGAGA CGAACCTTCA ATGGGTCTGG

1441 GACGTACTGT GTGAACCTCA CCCTGGGGGA TGACACAAGC CTGGCTCTCA CGAGCACCCT

FIG. 12R

1501 GATTTCTGTT CCTGACAGAG ACCCAGCCTC GCCTTTAAGG ATGGCAAACA GTGCCCTGAT

1561 CTCCGTTGGC TGCTTGGCCA TATTTGTCAC TGTGATCTCC CTCTTGGTGT ACAAAAAACA

1621 CAAGGAATAC AACCCAATAG AAAATAGTCC TGGGAATGTG GTCAGAAGCA AAGGCCTGAG

1681 TGTCTTTCTC AACCGTGCAA AAGCCGTGTT CTTCCCGGGA AACCAGGAAA AGGATCCGCT

1741 ACTCAAAAAC CAAGAATTTA AAGGAGTTTC TTAAATTTCG ACCTTGTTTC TGAAGCTCAC

1801 TTTTCAGTGC CATTGATGTG AGATGTGCTG GAGTGGCTAT TAACCTTTTT TTCCTAAAGA

1861 TTATTGTTAA ATAGATATTG TGGTTTGGGG AAGTTGAATT TTTTATAGGT TAAATGTCAT

1921 TTTAGAGATG GGGAGAGGGA TTATACTGCA GGCAGCTTCA GCCATGTTGT GAAACTGATA

1981 AAAGCAACTT AGCAAGGCTT CTTTTCATTA TTTTTTATGT TTCACTTATA AAGTCTTAGG

2041 TAACTAGTAG GATAGAAACA CTGTGTCCCG AGAGTAAGGA GAGAAGCTAC TATTGATTAG

2101 AGCCTAACCC AGGTTAACTG CAAGAAGAGG CGGGATACTT TCAGCTTTCC ATGTAACTGT

2161 ATGCATAAAG CCAATGTAGT CCAGTTTCTA AGATCATGTT CCAAGCTAAC TGAATCCCAC

2221 TTCAATACAC ACTCATGAAC TCCTGATGGA ACAATAACAG GCCCAAGCCT GTGGTATGAT

2281 GTGCACACTT GCTAGACTCA GAAAAAATAC TACTCTCATA AATGGGTGGG AGTATTTTGG

2341 TGACAACCTA CTTTGCTTGG CTGAGTGAAG GAATGATATT CATATATTCA TTTATTCCAT

FIG. 12S

2401 GGACATTTAG TTAGTGCTTT TTATATACCA GGCATGATGC TGAGTGACAC
TCTTGTGTAT
2461 ATTTCCAAAT TTTTGTATAG TCGCTGCACA TATTTGAAAT CATATATTAA
GACTTTCCAA
2521 AGATGAGGTC CCTGGTTTTT CATGGCAACT TGATCAGTAA GGATTTCACC
TCTGTTTGTA
2581 ACTAAAACCA TCTACTATAT GTTAGACATG ACATTCTTTT TCTCTCCTTC
CTGAAAAATA
2641 AAGTGTGGGA AGAGACAAAA AAAAAAAAA //

(SEQ ID NO. 91)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 92)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTA (SEQ ID NO. 93)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT

FIG. 12T

CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 94)

TACGAAGGTGGAGGCGGAGTCGAAGGCGAAGGGGGAGGGCATGGCCCGGGCACTGCA
GTTTGCACGGTGAGGTTAAGGTTGAAGGTTCCATTGAGCACATAAGTGTGATTCAAAG
TGTGATTGTTGGAGACAAACAGGCCAGTGTTGTCCCCAAAGTTCCACTTGTAGGAAAT
GGCAGAGTCGTTGAGGA (SEQ ID NO. 95)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 96)

RRWRRSRRRRGRAWPGHCSLHGEVKVEGSIEHISVIQSVIVGDKQASVVPKVPLVGNGRV
VEEVAGIMNEDIEDDGEVSEEDLIRQVPVILLGHGHEYRDLICYHIHIFHL (SEQ ID NO. 97)

KVKDVYVITDQIPVFVTMSQKNDRNLSDEIFLRDLPIVFDVLIHDPSHFLNDSAISYKWNFG
DNTGLFVSNNHTLNHTYVLNGTFNLNLTVQTAVPGPCPPPSPSTPPPPS (SEQ ID NO. 98)

FIG. 12U

YEGGGGVEGEGGGHGPGTAVCTVRLRLKVPLST*V*FKV*LLETNRPVLSPKFHL*EMAES
LRKWLGS*MRTSKTMGRSLRKISSDKFLSFFWDMVTNTGI*SVITYTSFT (SEQ ID NO. 99)

MECLYYFLGFLLLAARLPLDAAKRFHDVLGNERPSAYMREHNQLNGWSSDENDWNEKL
YPVWKRGDMRWKNSWKGGRVQAVLTSDSPALVGSNITFAVNLIFPRCQKEDANGNIVYE
KNCRNEAGLSADPYVYNWTAWSEDSDGENGTGQSHHNVFPDGK
PFPHHPGWRRWNFIYVFHTLGQYFQKLGRCSVRVSVNTANVTLGPQLMEVTVYRRHGRA
YVPIAQVKDVYVVTDQIPVFVTMFQKNDRNSSDETFLKDLPIMFDVLIHDPSHFLNYSTIN
YKWSFGDNTGLFVSTNHTVNHTYVLNGTFSLNLTVKAAAPGPCPPPPPPPRPSKPTPSLGP
AGDNPLELSRIPDENCQINRYGHFQATITIVEGILEVNIIQMTDVLMPVPWPESSLIDFVVTC
QGSIPTEVCTIISDPTCEITQNTVCSPVDVDEMCLLTVRRTFNGSGTYCVNLTLGDDTSLAL
TSTLISVPDRDPASPLRMANSALISVGCLAIFVTVISLLVYKKHKEYNPIENSPGNVVRSKGL
SVFLNRAKAVFFPGNQEKDPLLKNQEFKGVS (SEQ ID NO. 100)

1 CAGATGCCAG AAGAACACTG TTGCTCTTGG TGGACGGGCC CAGAGGAATT
CAGAGTTAAA
61 CCTTGAGTGC CTGCGTCCGT GAGAATTCAG CATGGAATGT CTCTACTATT
TCCTGGGATT
121 TCTGCTCCTG GCTGCAAGAT TGCCACTTGA TGCCGCCAAA CGATTTCATG
ATGTGCTGGG
181 CAATGAAAGA CCTTCTGCTT ACATGAGGGA GCACAATCAA TTAAATGGCT
GGTCTTCTGA
241 TGAAAATGAC TGGAATGAAA AACTCTACCC AGTGTGGAAG CGGGGAGACA
TGAGGTGGAA
301 AAACTCCTGG AAGGGAGGCC GTGTGCAGGC GGTCCTGACC AGTGACTCAC
CAGCCCTCGT
361 GGGCTCAAAT ATAACATTTG CGGTGAACCT GATATTCCCT AGATGCCAAA
AGGAAGATGC

FIG. 12V

421 CAATGGCAAC ATAGTCTATG AGAAGAACTG CAGAAATGAG GCTGGTTTAT CTGCTGATCC

481 ATATGTTTAC AACTGGACAG CATGGTCAGA GGACAGTGAC GGGGAAAATG GCACCGGCCA

541 AAGCCATCAT AACGTCTTCC CTGATGGGAA ACCTTTTCCT CACCACCCCG GATGGAGAAG

601 ATGGAATTTC ATCTACGTCT TCCACACACT TGGTCAGTAT TTCCAGAAAT TGGGACGATG

661 TTCAGTGAGA GTTTCTGTGA ACACAGCCAA TGTGACACTT GGGCCTCAAC TCATGGAAGT

721 GACTGTCTAC AGAAGACATG GACGGGCATA TGTTCCCATC GCACAAGTGA AAGATGTGTA

781 CGTGGTAACA GATCAGATTC CTGTGTTTGT GACTATGTTC CAGAAGAACG ATCGAAATTC

841 ATCCGACGAA ACCTTCCTCA AAGATCTCCC CATTATGTTT GATGTCCTGA TTCATGATCC

901 TAGCCACTTC CTCAATTATT CTACCATTAA CTACAAGTGG AGCTTCGGGG ATAATACTGG

961 CCTGTTTGTT TCCACCAATC ATACTGTGAA TCACACGTAT GTGCTCAATG GAACCTTCAG

1021 CCTTAACCTC ACTGTGAAAG CTGCAGCACC AGGACCTTGT CCGCCACCGC CACCACCACC

1081 CAGACCTTCA AAACCCACCC CTTCTTTAGG ACCTGCTGGT GACAACCCCC TGGAGCTGAG

1141 TAGGATTCCT GATGAAAACT GCCAGATTAA CAGATATGGC CACTTTCAAG CCACCATCAC

1201 AATTGTAGAG GGAATCTTAG AGGTTAACAT CATCCAGATG ACAGACGTCC TGATGCCGGT

1261 GCCATGGCCT GAAAGCTCCC TAATAGACTT TGTCGTGACC TGCCAAGGGA GCATTCCCAC

FIG. 12W

1321 GGAGGTCTGT ACCATCATTT CTGACCCCAC CTGCGAGATC ACCCAGAACA CAGTCTGCAG

1381 CCCTGTGGAT GTGGATGAGA TGTGTCTGCT GACTGTGAGA CGAACCTTCA ATGGGTCTGG

1441 GACGTACTGT GTGAACCTCA CCCTGGGGGA TGACACAAGC CTGGCTCTCA CGAGCACCCT

1501 GATTTCTGTT CCTGACAGAG ACCCAGCCTC GCCTTTAAGG ATGGCAAACA GTGCCCTGAT

1561 CTCCGTTGGC TGCTTGGCCA TATTTGTCAC TGTGATCTCC CTCTTGGTGT ACAAAAAACA

1621 CAAGGAATAC AACCCAATAG AAAATAGTCC TGGGAATGTG GTCAGAAGCA AAGGCCTGAG

1681 TGTCTTTCTC AACCGTGCAA AAGCCGTGTT CTTCCCGGGA AACCAGGAAA AGGATCCGCT

1741 ACTCAAAAAC CAAGAATTTA AAGGAGTTTC TTAAATTTCG ACCTTGTTTC TGAAGCTCAC

1801 TTTTCAGTGC CATTGATGTG AGATGTGCTG GAGTGGCTAT TAACCTTTTT TTCCTAAAGA

1861 TTATTGTTAA ATAGATATTG TGGTTTGGGG AAGTTGAATT TTTTATAGGT TAAATGTCAT

1921 TTTAGAGATG GGGAGAGGGA TTATACTGCA GGCAGCTTCA GCCATGTTGT GAAACTGATA

1981 AAAGCAACTT AGCAAGGCTT CTTTTCATTA TTTTTTATGT TTCACTTATA AAGTCTTAGG

2041 TAACTAGTAG GATAGAAACA CTGTGTCCCG AGAGTAAGGA GAGAAGCTAC TATTGATTAG

2101 AGCCTAACCC AGGTTAACTG CAAGAAGAGG CGGGATACTT TCAGCTTTCC ATGTAACTGT

2161 ATGCATAAAG CCAATGTAGT CCAGTTTCTA AGATCATGTT CCAAGCTAAC TGAATCCCAC

FIG. 12X

2221 TTCAATACAC ACTCATGAAC TCCTGATGGA ACAATAACAG GCCCAAGCCT GTGGTATGAT

2281 GTGCACACTT GCTAGACTCA GAAAAAATAC TACTCTCATA AATGGGTGGG AGTATTTTGG

2341 TGACAACCTA CTTTGCTTGG CTGAGTGAAG GAATGATATT CATATATTCA TTTATTCCAT

2401 GGACATTTAG TTAGTGCTTT TTATATACCA GGCATGATGC TGAGTGACAC TCTTGTGTAT

2461 ATTTCCAAAT TTTTGTATAG TCGCTGCACA TATTTGAAAT CATATATTAA GACTTTCCAA

2521 AGATGAGGTC CCTGGTTTTT CATGGCAACT TGATCAGTAA GGATTTCACC TCTGTTTGTA

2581 ACTAAAACCA TCTACTATAT GTTAGACATG ACATTCTTTT TCTCTCCTTC CTGAAAAATA

2641 AAGTGTGGGA AGAGACAAAA AAAAAAAAA // (SEQ ID NO. 101)

MECLYYFLGFLLLAARLPLDAAKRFHDVLGNERPSAYMREHNQLNGWSSDENDWNEKL
YPVWKRGDMRWKNSWKGGRVQAVLTSDSPALVGSNITFAVNLIFPRCQKEDANGNIVYE
KNCRNEAGLSADPYVYNWTAWSEDSDGENGTGQSHHNVFPDGKPFPHHPGWRRWNFIY
VFHTLGQYFQKLGRCSVRVSVNTANVTLGPQLMEVTVYRRHGRAYVPIAQVKDVYVVT
DQIPVFVTMFQKNDRNSSDETFLKDLPIMFDVLIHDPSHFLNYSTINYKWSFGDNTGLFVS
TNHTVNHTYVLNGTFSLNLTVKAAAPGPCPPPPPPPRPSKPTPSLGPAGDNPLELSRIPDEN
CQINRYGHFQATITIVEGILEVNIIQMTDVLMPVPWPESSLIDFVVTCQGSIPTEVCTIISDPT
CEITQNTVCSPVDVDEMCLLTVRRTFNGSGTYCVNLTLGDDTSLALTSTLISVPDRDPASP
LRMANSALISVGCLAIFVTVISLLVYKKHKEYNPIENSPGNVVRSKGLSVFLNRAKAVFFPG
NQEKDPLLKNQEFKGVS* (SEQ ID NO. 102)

FIG. 12Y

CTGACCAGGAACCCACTCTTCTGTGCATGTATGTGAGCTGTGCAGAAGTATGTGGCTG
GGAACTGTTGTTCTCTAAGGATTATTGTAAAATGTATATCGTGGCTTAGGGAGTGTGG
TTAAATAGCATTTTAGAGAAGAAAAAAAAAAAAAAAAAAACTCGAGAGTACTTCTAG
AGCGGCCGCGGCGCCATCGATTTTCCACCCGGGTGGGGTACCAGGTAAGTGTACCCAA
TTCGCCTATAGTGAGT (SEQ ID NO. 103 )

AGGACAAGCCAAGGACACTCTAAGTCTTTGGCCTTCCCTCTGACCAGGAACCCACTCT
TCTGTGCATGTATGTGAGCTGTGCAGAAGTATGTGGCTGGGAACTGTTGTTCTCTAAG
GATTATTGTAAAATGTATATCGTGGCTTAGGGAGTGTGGTTAAATAGCATTTTAGAGA
AGACATGGGAAGACTTAGTGTTTCTTCCCATCTGTATTGTGGTTTTTACACTGTTCGTG
GGGTGGACACGCTGTGTCTGAAGGGGAGGTGGGGGTCACTGCTACTTAAGGTCCTAGG
TTAACTGGGGGAGATACCACAGATGCTCAGCTTTCCACATAACATGGGCATGAACCAG
CTAATCACACTGAA (SEQ ID NO. 104)

GGATCCTTCTCCTGGTCTCCTCGGAAGAACGGGGCTTTCGCGTGACTGAGGAGAACAC
TCAGGCCCTTGCCCTTGACCGTGTTCCTGGGGCAGTTTCCTATTGGCTTGTACGCCTTG
TGTTTTTTGTACAGCAAGATGGTAACCATGGTGACAAGCACAGCCAGGCAGCCGATGG
AGATCAGGACACCATTCACTGCTCTCAGAGGGAGTCTGGGTCTTTGCCAGGGATAGAG
ATCAGGGTGCTGGTGAGGGCCAGGCTTCGATCATCTCCCAGAGTGAAATTCACACAGT
AGGTGCCAGACCCATTGAAGGCTCTTCTCACAGACAGCAGCACAGCCCATCCACAGCC
ACAGGGCTGCAGACCCGGTTCTGGGCGATCTGGCAGGTGGGGTCGGAGATGATCGTA
CAGGCTTCCATGGGGGTGGCCCCTTTGCAGGTCACAGTGAAGTCCATCAGGGAGTTGG
CAGGCTGCGGTGTGGGCATGGGGACATCTGCTATCTGCATGATGCTGACTTCCAGGATCC
(SEQ ID NO. 105)

TAGCAGATGTCCCCATGCCCACACCGCAGCCTGCCAACTCCCTGATGGACTTCACTGT
GACCTGCAAAGGGGCCACCCCCATGGAAGCCTGTACGATCATCTCCGACCCCACCTGC
CAGATCGCCCAGAACCGGGTCTGCAGCCCTGTGGCTGTGGATGGGCTGTGCTGCTGTC

FIG. 12Z

TGTGAGAAGAGCCTTCAATGGGTCTGGCACCTACTGTGTGAATTTCACTCTGGGAGAT
GATCGAAGCCTGGCCCTCACCAGCACCCTGATCTCTATCCCTGGCAAAGACCCAGACT
CCCTCTGAGAGCAGTGAAT (SEQ ID NO. 106)

GGATCCTTCTCCTGGTCTCCTCGGAAGAACGGGGCTTTCGCGTGACTGAGGAGAACAC
TCAGGCCCTTGCCCTTGACCGTGTTCCTGGGGCAGTTTCCTATTGGCTTGTACGCCTTG
TGTTTTTTGTACAGCAAGATGGTAACCATGGTGACAAGCACAGCCAGGCAGCCGATGG
AGATCAGGACACCATTCACTGCTCTCAGAGGGAGTCTGGGTCTTTGCCAGGGATAGAG
ATCAGGGTGCTGGTGAGGGCCAGGCTTCGATCATCTCCCAGAGTGAAATTCACACAGTA
(SEQ ID NO. 107)

TTTTTTTTTTTTTTTTTTTAGACTGCCTTTTTAATGAGTAGAATATGTACACACACGCACC
ATACACAAAGCCCGGGCCCATTATAATTTTGTCAGGAGCTCAGGCATGCTCAGTGAGT
TGGAAGGCAGATGAAGCATG
CCTTCAGGTGGTGATTAGCTGGGTTCATGCCCATGTTATCGTGGAAAGCTGAGGCATC
TGTGGTATCTCCCCCAGTTAACCTAGGACCTTAAGTAGCAGTGACCCACCTCCCTTCAG
ACACAGCG
(SEQ ID NO. 108)

GGATCCTGGAAGTCAGCATCATGCAGATAGCAGATGTCCCCATGCCCACACCGCAGCC
TGCCAACTCCCTGATGGACTTCACTGTGACCTGCAAAGGGGCCACCCCCATGGAAGCC
TGTACGATCATCTCCGACCCCACCTGCCAGATCGCCCAGAACCGGGTCTGCAGCCCTG
TGGCTGTGGATGGGCTGTGCTGCTGTCTGTGAGAAGAGCCTTCAATGGGTCTGGCACC
TACTGTGTGAATTTCACTCTGGGAGATGATCGAAGCCT
(SEQ ID NO. 109)

FIG. 12AA

TTTTTTTTTTTTTTTTTTTCTTCTCTAAAATGCTATTTAACCACACTCCCTAAGCCACGA
TATACATTTTACAATAATCCTTAGAGAACAACAGTTCCCAGCCACATACTTCTGCACA
GCTCACATACATGCACAGAAGAGTGGGTTCCTGGTCAGAGGGAAGGCCAAAGACTTA
GAGTGTCCTTGGCTTGTCTGGAGCAATGGATCCTTCTCCTGGTCTCCTCGGAAGAACG
GGCTTT (SEQ ID NO. 110)

AAACTGCAGTGCCCGGGCCATGCCCTCCCCCTTCGCCTTCGACTCCGCCTCCACCTTCA
ACTCCGCCCTCACCTCCGCCCTCACCTCTGCCCACATTATCAACACCTAGCCCCTCTTT
AATGCCTACTGGTTACAAATCCATGGAGCTGAGTGACATTTCCAATGAAAACTGCCGA
ATAAACAGATATGGCTACTTCAGAGCCACCATCACAATTGTAGAGGGGATCCTGGACG
CAGCATCATGCAGATAGCAGATGTCCCATGCCCACACCGCAGCCGTCCAACTCCTGAT
GGACTTCACTGTGACCTCAAGGGCACCCATGGAAGCTGTCAGA (SEQ ID NO. 111)

CCTCAACGACTCTGCCATTTCCTACAAGTGGAACTTTGGGGACAACACTGGCCTGTTT
GTCTCCAACAATCACACTTTGAATCACACTTATGTGCTCAATGGAACCTTCAACCTTAA
CCTCACCGTGCAAACTGCAGTGCCCGGGCCATGCCCTCCCCCTTCGCCTTCGACTCCGC
CTCCACCTTCAACTCCGCCCTCACCTCCGCCCTCACCTCTG (SEQ ID NO. 112)

CCTCAACGACTCTGCCATTTCCTACAAGTGGAACTTTGGGGACAACACTGGCCTGTTT
GTCTCCAACAATCACACTTTGAATCACACTTATGTGCTCAATGGAACCTTCAACCTTAA
CCTCACCGTGCAAACTGCAGTGCCCGGGCCATGCCCTCCCCCTTCGCCTTCGACTCCGC
CTCCACCTTCAACTCCGCCCTCACCTCCGCCCTCACCTCTGCCCACATTATCAACACCT
AGCCCCTCTTTAATGCCTACTGGTTACAAATCCATGGAGCTGAGTGACATTTCCAATG
AAAACTGCCGAATAAACAGATATGGCTACTTCAGAGCCACCATCACAATTGTAGAGG
GGATCCTGGAAGTCAGCATCATGCAGATAGCAGATGTCCCCATGCCCACACCGCAGCC
TGCCAACTCCCTGATGGACTTCACTGTGACCTGCAAAGGGGCCACCCCCATGGAAGCC
TGTACGATCATCTCCGACCCCACCTGCCAGATCGCCCAGAACCGGGTCTGCAGCCCTG

FIG. 12BB

TCCTGTGGATCCCTGTCCTCCTGTCTGTGAGAAGACCCTCAATCCGTCTCCCACCTACTGTGTGAATTCACTCTCCGAGATGATCCAACCCT (SEQ ID NO. 113)

GGATCCCCTCTACAATTGTGATGGTGGCTCTGAAGTAGCCATATCTGTTTATTCGGCAG
TTTTCATTGGAAATGTCACTCAGCTCCATGGATTTGTAACCAGTAGGCATTAAAGAGG
GGCTAGGTGTTGATAATGTGGGCAGAGGTGAGGGCGGAGGTGAGGGCGGAGTTGAAG
GTGGAGGCGGAGTCGAAGGCGAAGGGGGAGGGCATGGCCCGGGCACTGCAGTTTGCA
CGGTGAGGTTAAGGTTGAAGGTTCCATTGAGCACATAAGTGTGATTCAAAGTGTGATT
GTTGGAGACAAACAGGCCAGTGTTGTCCCAAAGTTCCACTTGTAGGAATGGCAGAGTC
GTTGAGG (SEQ ID NO. 114)

CCTCAACGACTCTGCCATTTCCTACAAGTGGAACTTTGGGGACAACACTGGCCTGTTT
GTCTCCAACAATCACACTTTGAATCACACTTATGTGCTCAATGGAACCTTCAACCTTAA
CCTCACCGTGCAAACTGCAGTGCCCGGGCCATGCCCTCCCCCTTCGCCTTCGACTCCGC
CTCCACCTTCAACTCCGCCCTCACCTCCGCCCTCACCTCTGCCCACATTATCAACACCT
AGCCCCTCTTTAATGCCTACTGGTTACAAATCCATGGAGCTGAGTGACATTTCCAATG
AAAACTGCCGAATAAACAGATATGGCTACTTCAGAGCCACCATCACAATTGTAGAGG
GGATCCTGGAAGTCAGCATCATGCAGATAGCAGATGTCCCCATGCCCACACCGCAGCC
TGCCAACTCCCTGATGGACTTCACTGTGACCTGCAAAGGGGCCACCCCCATGGAAGCC
TGTACGA (SEQ ID NO. 115)

GAAGGTGGAGGCGGAGTCGAAGGCGAAGGGGGAGGGCATGGCCCGGGCACTGCAGTT
TGCACGGTGAGGTTAAGGTTGAAGGTTCCATTGAGCACATAAGTGTGATTCAAAGTGT
GATTGTTGGAGACAAACAGGCCAGTGTTGTCCCCAAAGTTCCACTTGTAGGAAATGGC
AGAGTCGTTGAGGAAGTGGCTGGGATCATGAATGAGGACATCGAAGACGA (SEQ ID NO. 116)

FIG. 12CC

GAATTCGCACGAGGGGAGTCAGAGTCAAGCCCTGACTGGTTGCAGGCGCTCGGAGTC
AGCATGGAAAGTCTCTGCGGGGTCCTGGGATTTCTGCTGCTGGCTGCAGGACTGCCTC
TCCAGGCTGCCAAGCGATTTCGTGATGTGCTGGGCCATGAACAGTATCCCGATCACAT
GAGAGAGCACAACCAATTACGTGGCTGGTCTTCGGATGAAAATGAATGGGTTCCAATA
TCACTTTTGTGGTGAA (SEQ ID NO. 117)

GAATTCGGCACGAGGAAGGAGGCCGTGTGCAGGCAGTCCTGACCAGTGACTCACCGG
CTCTGGTGGGTTCCAATATCACTTTTGTGGTGAACCTGGTGTTCCCCAGATGCCAGAAG
GAAGATGCTAATGGCAATATCGTCTATGAGAAGAACTGCAGGAATGATTTGGGACTG
ACATCTGACCTGCATGTCTACAACTGGACTGCAGGGGCAGATGATGGTGACTGGGAAG
ATGGCACCT (SEQ ID NO. 118)

GAAGGTGGAGGCGGAGTCGAAGGCGAAGGGGGAGGGCATGGCCCGGGCACTGCAGTT
TGCACGGTGAGGTTAAGGTTGAAGGTTCCATTGAGCACATAAGTGTGATTCAAAGTGT
GATTGTTGGAGACAAACAGGCCAGTGTTGTCCCCAAAGTTCCACTTGTAGGAAATGGC
AGAGTCGTTGAGGAAGTGGCTGGGATCATGAATGAGGACATCGAAGACGATGGGGAG
GTCTCTGAGGAAGATCTCATCAGACAAGTT (SEQ ID NO. 119)

GAATTCGGCACGAGGTCAAGCCCTGACTGGTTGCAGGCGCTCGGAGTCAGCATGGAA
AGTCTCTGCGGGGTCCTGGGATTTCTGCTGCTGGCTGCAGGACTGCCTCTCCAGGCTGC
CAAGCGATTTCGTGATGTGCTGGGCCATGAACAGTATCCCGATCACATGAGAGAGCAC
AACCAATTACGTGGCTGGTCTTCGGATGAAAATGAATGGATGAACACCTTGTATCCA
(SEQ ID NO. 120)

FIG. 12DD

AAGGGGGAGGGCATGGCCCGGGCACTGCAGTTTGCACGGTGAGGTTAAGGTTGAAGG
TTCCATTGAGCACATAAGTGTGATTCAAAGTGTGATTGTTGGAGACAAACAGGCCAGT
GTTGTCCCCAAAGTTCCACTTGTAGGAAATGGCAGAGTCGTTGAGGAAGTGGCTGGGA
TCATGAATGAGGACATCGAAGACGATGGGGAGGTCTCTGAGGAAGATCTCATCAGAC
AAGTTCCTGTCATTCTTCTGGGACATGGTCACGAATACAGGGATCTGATCTGTTAT
(SEQ ID NO. 121)

GAATTCGGCACGAGCCGACACTGTGACTCCTGGTGGATGGGACTGGGGAGTCAGAGT
CAAGCCCTGACTGGTTGCAGGCGCTCGGAGTCAGCATGGAAAGTCTCTGCGGGGTCCT
GGGATTTCTGCTGCTGGCTGCAGGACTGCCTCTCCAGGCTGCCAAGCGATTTCGTGAT
GTGCTGGGCCATGAACAGTATCCCGATCACATGAGAGAGCACAACCAATTA
(SEQ ID NO. 122)

AAGGTGAAAGATGTGTATGTGATAACAGATCAGATCCCTGTATTCGTGACCATGTCCC
AGAAGAATGACAGGAACTTGTCTGATGAGATCTTCCTCAGAGACCTCCCCATCGTCTT
CGATGTCCTCATTCATGATCCCAGCCACTTCCTCAACGACTCTGCCATTTCCTACAAGT
GGAACTTTGGGGACAACACTGGCCTGTTTGTCTCCAACAATCACACTTTGAATCACAC
TTATGTGCTCAATGGAACCTTCAACCTTAACCTCACCGTGCAAACTGCAGTGCCCGGG
CCATGCCCTCCCCCTTCGCCTTCGACTCCGCCTCCACCTTCGTA (SEQ ID NO. 123)

TACCATCGGAGAAAGAAGACCAAGCAAGGCTCAGGCAGCCACCGCCTGCTTCGCACT
GAGCCTCCTGACTCAGACTCAGAGTCCAGCACAGACGAAGAGGAATTTGGAGAATTG
GAAATCGCTCTCGTTTTGTCAAGGGAGACTATCCCGATGCTGCAAGATCTGCTGTCCCT
CTGGCCTTTGTCATCCTCGCGCCTGCGTTGTGGCCTCTGTGGGCTTGGTGTGGAGCAAA
TGGCTCTCAAGGAGGACTGAGTCTCAAGGAAATT (SEQ ID NO. 124)

FIG. 12EE

AGCTAAGGTCAGGAGGTGTCTGAAGAATTGGCTGATGCATGGCAGGGATGTTGTTGAC
CTGCTTTTAGAACAATACTTCCATTTAATTATAGCATATCTTATGTGTGTATTAAAGCA
GAGCCGATCTGGTGGGGCTCATTAAGTAAATGTACTTACTGCAAAAGGTTCAACTGGT
GACCCCAGTTTTCCCCAGAAGCAATATGATAGGACAGAGGCGACTCCTGCAAGTTGTC
TCAGACTTCACACATACATTGTGACATTCTCTGAGCATGTGCACTGTACATGATATGAC
ACTATCAA (SEQ ID NO. 125)

AGCTAAGGTCCACTACCTTGTGAAGATGTATAAACACCTGAAATGTAGAAGCGATCCG
TATGTCAAGATCGAGGGGAAGGACGCTGACGACTGGCTGTGTGTGGACTTTGGGAGTA
TGGTGATCCATTTGATGCTTCCAGAAACCAGAGAAACCTATGAATTAGAGAAACTATG
GACTCTACGTTCTTTTGATGACCTTAGCTAAGCCGAATCAGCACACTGGCGGCGTTACT
AGTGGATCGAGCTCGTACAGCTGATGCATAGCTTGAGTATCTATAGGTTACTAATAGC
TGGCTATCATGTCAAGCGTTC (SEQ ID NO. 126)

GCTGAGCTGCAGAGAGTAGCACATCCTTGCTAATTCAATAACTACCAGTTTTTATTGGT
GAAACATGAATCCAGATGGTATGGTTGCTCTCCTGGACTACCGTGAAGATGGTGTGAC
TCCATTCATGATTTTCTTTAAGGATGGCTTAGAGATGGAGAAATGTTAACAAATTGGA
TCTATCACCTGTCACCATAATTGGCTGCTGCTTACCATCCATACAACACCAGGACTTAG
GACAAATGGGACTGATGTCATCTTGAGCTTTTATTTTGACCTTAGCT
(SEQ ID NO. 127)

AGCTAAGGTCAGAGCCAATAGTATCATGAGAACTGAAGAAGTAATAAAGCAACTTCT
CCAGAAATTTAAGATTGAGAATAGCCCTCGGGATTTCGCTCTTTACATTATTTTTGGGA
CAGGAGAGCAGAGAAAGCTAAAGAAGACCGATGTCCACTGCTGCAGAGGTTACTACA
AGGACCATCCAAAAGCAATGCTCGGATCTCTCATGGATAAAGATGCAGAAGAATCAC
GAGAGATGTGGCTCGTACATTATTTCACTTTCTTCTGATCATACTCAAGATAGATGAGA
GAGAAT (SEQ ID NO. 128)

FIG. 12FF

TTGACTTCTGAGTCTAACACAGACACTGCAAGGGTTAATTTTCCAAGAGGTGGTTGTT
GTTGACGATAAATTCATTAAGAATTTTTAAAAATTTAGTTAGATTTACCAAAGTCACTG
GAGACAAATTCAGAAGGCATATATACCTGCCAGTTTTGTGGACTACATTAATAGGGAG
GCTTTTATGTTTGATGTAATTCTTACAGTTCTAAGAATTAAGTTCCATTGCATGAGACC
TTAGCT (SEQ ID NO. 129)

AAGGTGAATCCCCGACGGCTCTGGGCCCGAGGAGAAGCGTCGCCGTGGCAAATTGGC
ACTGCAGGAGAAGCCCTCCACAGGTACTTGGAAAAACTGGTCTCTGAGGCCAAGGCC
AGCTCCGAGACATTCAGGACTTCTGGATCAGCCTCCAGGGACACTGTGCAGTGAGAAG
ATGGCCATGAGTCCTGCCAGTGAG (SEQ ID NO. 130)

AATTTTTTTTTTCGACGGCCCAACGGGGGCTTGGTGGATGGAAATATGGTTTTGTGAGT
TATTGCACTACCTGGAATATCTATGCCTCTTATTTGCGTGTACTGTTGCTGCTGATCGT
TTGGTGCTGTGTGAGTGAACCTATGGCTTAGAAAAACGACTTTGTCTTAAACTGAGTG
GGTGTTCAGGG (SEQ ID NO. 131)

CACCTGATTTAAAGGAAAAGCATTCTGACGTAAGAAGCTGAAAGGCGGCCCTTGCGTG
CTTTGAACTTTCTTATACAGCACAGTCATCTGAAGCTTCCTGTGTGACCAAGACAAGA
ACGCGTGCACAAGACTGAGAAACAGCAAGAAACAACCCGGCATTCTACTTTCTCAAC
ACTATCATACTTTAAACCTTTCAC (SEQ ID NO. 132)

FIG. 12GG

CTAGCTTACGCTAGTCCCCCATGCATAAAGACTGATCGCTTTTCCTTAGAAAGGTGAG
AGGGTTAGGACAAGGCCGTGTGGTAACAACACCCGCAGCTCGAAAAACCAATGGCTT
GTTAACGTGTCAGTGAGGCACTGTACGGACGTCCATAGTCCACATCTTCAAATTCCCG
CAGAAGGCTTCCTATTCTTAAACTCTA (SEQ ID NO. 133)

CTACATTTCTGTATCCATTCCTCTGTTGAAGGCTCTGGTTCTTTCCAGCTTCTGGCTATT
ATAAATAAGGCTGCTATAAACACAGTGGAGGCATGTGTCCTTGTTATATTTTGGAGCA
TCTTTTGGGTATATGCCCAGAAGTGCTATAGCTGGTTCCTCAGGTAGTACTATGTCGAA
TTTTCTGAGGAACTGCCAGACTGATTTCCAGAGTGGTTGTACCAGCTTGCAATCCCACC
AGCAATAGAGGAGTGTTCCTCTTTCTCTATATTCTTGCCAACATCTGCTGTCACCTGAG
TGTTT (SEQ ID NO. 134)

TGGTAAAGGGGGAATGATGTCGAGGCCATCCTGGGCTGTAGAGCCAGGCCCTGGCTTG
GGGAGTGGGCATTGTTAACTTGTTGCTGACTTTGTGTTGACCCCTGCATCAGCAACTAT
TTCCTTAAATCCAGGATACAACTTGTTAAGTGTGACAGCTTTCCTTTACACACCATTTT
TGTGGGTGTATATATATATTTGACTTGGGGAGAATTATTTTTTACAAAAATACAAAAT
AGCTTTTAA (SEQ ID NO. 135)

AGCTAAGGTCCGGACTCTATGGCATGACCCCAAAAACATTGGCTGGAAAGATTACACT
GCCTACAGGTGGCACCTGATTCACAGGCCTAAGACAGGCTACATGAGAGTCTTAGTGC
ATGAAGGAAAGCAAGTCATGGCTGACTCAGGACCAATTTATGACCAAACCTACGCTG
GTGGACGGCTGGGCTGTTTGTCTTCTCCAAGAGATGGTCTATTCTCGGACCTCAAGTAT
GAGTGCAGAGATGCTAGAGAGCAGGCTCAGTCTCAGCA (SEQ ID NO. 136)

FIG. 12HH

TGACCTACGTGTAGTTGGTGTGCTTGTTGTCGAAGATGAGGGCCTCCTGGATGAGCTG
GTGCTGCTGCTCCAGCAGGTCCAGGCTGGGCTTGTAGTCCACGAGTCTGCGCTCGTAC
TGCTTCAGGTGGCTCAGCTGGTCTTCCAGAGTCCCGTTCATCTCAATGGAGATGCGCCC
GATCTCCTCCATCTTAGTCTGGATCCACGGCCCCACCATATTGGCTTGGCTGGCGAACT
GTCGGCGAAGGCTGCATTGGATTGCT (SEQ ID NO. 137)

AATTTTTTTTTTCGACGGCCCAACGGGGGCTTGGTGGATGGAAATATGGTTTTGTGAGT
TATTGCACTACCTGGAATATCTATGCCTCTTATTTGCGTGTACTGTTGCTGCTGATCGT
TTGGTGCTGTGTGAGTGAACCTATGGCTTAGAAAAACGACTTTGTCTTAAACTGAGTG
GGTGTTCAGGG (SEQ ID NO. 138)

CACCTGATTTAAAGGAAAAGCATTCTGACGTAAGAAGCTGAAAGGCGGCCCTTGCGTG
CTTTGAACTTTCTTATACAGCACAGTCATCTGAAGCTTCCTGTGTGACCAAGACAAGA
ACGCGTGCACAAGACTGAGAAACAGCAAGAAACAACCCGGCATTCTACTTTCTCAAC
ACTATCATACTTTAAACCTTTCAC (SEQ ID NO. 139)

CTAGCTTACGCTAGTCCCCCATGCATAAAGACTGATCGCTTTTCCTTAGAAAGGTGAG
AGGGTTAGGACAAGGCCGTGTGGTAACAACACCCGCAGCTCGAAAAACCAATGGCTT
GTTAACGTGTCAGTGAGGCACTGTACGGACGTCCATAGTCCACATCTTCAAATTCCCG
CAGAAGGCTTCCTATTCTTAAACTCTA (SEQ ID NO. 140)

CTACATTTCTGTATCCATTCCTCTGTTGAAGGCTCTGGTTCTTTCCAGCTTCTGGCTATT
ATAAATAAGGCTGCTATAAACACAGTGGAGGCATGTGTCCTTGTTATATTTTGGAGCA
TCTTTTGGGTATATGCCCAGAAGTGCTATAGCTGGTTCCTCAGGTAGTACTATGTCGAA

FIG. 12II

TTTTCTGAGGAACTGCCAGACTGATTTCCAGAGTGGTTGTACCAGCTTGCAATCCCACC
AGCAATAGAGGAGTGTTCCTCTTTCTCTATATTCTTGCCAACATCTGCTGTCACCTGAG
TGTTT (SEQ ID NO. 141)

TGGTAAAGGGGGAATGATGTCGAGGCCATCCTGGGCTGTAGAGCCAGGCCCTGGCTTG
GGGAGTGGGCATTGTTAACTTGTTGCTGACTTTGTGTTGACCCCTGCATCAGCAACTAT
TTCCTTAAATCCAGGATACAACTTGTTAAGTGTGACAGCTTTCCTTTACACACCATTTT
TGTGGGTGTATATATATATTTGACTTGGGGAGAATTATTTTTTACAAAAATACAAAAT
AGCTTTTAA (SEQ ID NO. 142)

AGCTAAGGTCCGGACTCTATGGCATGACCCCAAAAACATTGGCTGGAAAGATTACACT
GCCTACAGGTGGCACCTGATTCACAGGCCTAAGACAGGCTACATGAGAGTCTTAGTGC
ATGAAGGAAAGCAAGTCATGGCTGACTCAGGACCAATTTATGACCAAACCTACGCTG
GTGGACGGCTGGGCTGTTTGTCTTCTCCAAGAGATGGTCTATTCTCGGACCTCAAGTAT
GAGTGCAGAGATGCTAGAGAGCAGGCTCAGTCTCAGCA
(SEQ ID NO. 143)

TGACCTACGTGTAGTTGGTGTGCTTGTTGTCGAAGATGAGGGCCTCCTGGATGAGCTG
GTGCTGCTGCTCCAGCAGGTCCAGGCTGGGCTTGTAGTCCACGAGTCTGCGCTCGTAC
TGCTTCAGGTGGCTCAGCTGGTCTTCCAGAGTCCCGTTCATCTCAATGGAGATGCGCCC
GATCTCCTCCATCTTAGTCTGGATCCACGGCCCCACCATATTGGCTTGGCTGGCGAACT
GTCGGCGAAGGCTGCATTGGATTGCT
(SEQ ID NO. 144)

TGACCATCGATAAGTTTAATAACTACAGACTTTTCCCAAGACTACAAAAGCTTCTTGA
AAGTGACTACTTTAGATATTACAAGGTGAACTTGAAGAAGCCTTGTCCTTTCTGGAAT

FIG. 12JJ

GACATCAACCAGTGTGGAAGAAGAGACTGTGCCGTCAAACCCTGCCATTCTGATGAAG
TTCCTGATGGAATTAAGTCTGCCGAGCTACAAGTATTCTG
AGGAAGCCCAACCGCATTGAAGAATGTGAGCAAGCTGAGCG (SEQ ID NO. 145)

AACTCTGTGAACCGTGCCTTTCTCTGTGGAGGTGGAGGTGTCGGTTGAAGACAAGCGA
GGTCCTCCAAGGGGCTGTGTCTTATGTTGCCATCTCCCCTTGTAGCTTGGCTGCCCACC
CTCCAGACTGTGCGCCATGGCTCCAAGGCTGTGACCCGCCACTGGAGTCATGCACTTC
CAGCGGCAGAAGCTGATGCTATAACTGAGTATATTCCTCCAAACCTGCCATCAACCCG
AGA (SEQ ID NO. 146)

ACTTCTCCAGAGAATTTAAGATTGAGAATAGCCCTCGGGATTTCGCTCTTTACATTATT
TTTGGGACAGGAGAGCAGAGAAAGCTAAAGAAGACCGATGTCCCACTGCTGCAGAGG
TTACTACAAGGACCATCCAAAAGCAATGCTCGGATCTTCCTCATGGATAAAGATGCAG
AAGAAATCAGCAGAGATGTGGCTCCGTACATTAATTTCACTTTTCTTTCTTGGATCCAT
CCTTCAAGATTAGATGAAGAAGAGAAATGGAGATTGAGAGAATATGCAATCATACCGA
(SEQ ID NO. 147)

AGGGTTACTTCAGGCTAAGGCAATAGAAATCCATTTTAAGATGGTGTGCTAAAGGCTT
GATGGATGTTCATCGTCTGTCTAAAGGAGAATGAAGTCATCAACAGGATGTCAGGGGA
AAGTGAGATCATCGCAGAAAGTATCAACTTAGCACAAACACACAGGCATAGCTCCTG
CAAGAGGTGAATGCTGTCCCCAAATACCTGAGGAACTATCCCTTTGGGCAAGAAAATA
GACAAGTCCATGAAGTCTGGGTGA
(SEQ ID NO. 148)

GACCAGGTACACTTGAGCAAAGCACCCAGTATTTAATTCCTTACAGAAAGGAGAGGA
AAGGTCTGCAGTTGGACTGATGGTATGCTAACACCGCAAATGACTGTCATTTGATCTC

FIG. 12KK

AGAAGTTCAGGATTGATTGCTATGTTTTAGCTCTAATTGTGAGAAACAGTAGTCATTTT
AGTCTTAAATTTTGCCCTCAGGAAATTCAGGGAGACTGAGCCTTCCTTCCCCCACCTTC
GTAAAGCCGAATTCCAGCACACGGCGGCCGTTACTAGTGGATCCGAGCTCG
(SEQ ID NO. 149)

TACAAGGTGGGATGGCAGGAACTGAAGGCTTCTGTAAATCCAGTTTTGGCTCTCTCTC
TGGTCTTTCTTTCTCTTCTGTTCTGTTTGGAAGGGTTTCTGGTCTTTCAGGAGGTATTTT
TTTAATTTCATGTTTTCTCTCTGTGGTACCTGCCCCTTGTTTGACGACAGGAGCTGATG
GAGGTGGCGGTTTCTTGGGTCTATTCCCTTCCTTGTCAAAGTCCGATGGAAGTAACTTC
ACGAAGTTGTCAGGAAACACGCCTCGTCTGCCATTGAGTTCTCCTTCCCACCAGCCTA
CGCGATGCAGTCTTATTGATGAGAGTCACTATATCTCCTTA (SEQ ID NO. 150)

TCACCCATGACTTCTATGGACTTGTCTATTTTCTTGCCCAAAGGGATAGTTCCTCAGGT
ATTTGGGGACAGCATTCACCTCTTGCAGGAGCTATGCCTGTGTGTTTGTGCTAAGTTGA
TACTTTCTGCGATGATCTCACTTTCCCCTGACATCCTGTTGATGACTTCATTCTCCTTTA
GACAGACGATGAACATCCATCAGGCCTTTATGCACACCATCTTAAAATGGATTTCTAT
TGCCTTAGCCTGAAGTCC (SEQ ID NO. 151)

CCCATAGAGATAGGTTTGCTCCAGAACCTGCAGCATTTGCACATCACAGGGAACAAGG
TGGACATTCTGCCAAAACAGTTGTTTAAGTGCGTGAAGTTGAGGACTTTGAACCTGGG
GCAGAACTGTATCGCCTCCCTGCCTGAGAAAATCAGTCAGCTCACCCAGCTCACTCAG
CTGGAGCTGAAGGGCAACTGCCTAGACCGCCTGCCAGCCCAGCTGGCAGTGTCGATGC
TCAAGAAGA (SEQ ID NO. 152)

CAATAATCCAGGTAAAATAGAGTAAAATAGTCTGCTAGCAGCAAGTTCCTACCATACT
TTCAACAACACTCACGAGATACGGAATGATTACAGCATTAAGAATATTTCAGAAATGA
CAGGTAGGTGTGGTGGACAGGTGGCTCACATTCAAGACTCAAGTCTACTTAAAAAAGA

FIG. 12LL

AAATCTCACTAGCACTAGATTCTAGCTCCTTTGTTTCCCCCTTTCTTTTGGTTTCAAAG
GCGTTTCTACAACCCATAAGAGG (SEQ ID NO. 153)

GCCAAGCTATTATGACACTATAGATACTCAACGTATCGATCAACGTTGGTACCGAGCT
CGGATCCACTAGTAACGGCCGCCAGTGTGCTGGAATTCGGCTTGGATTGGTCAGAGCA
GTGTGCAATATGATCCAACTAAGTCTCCTCCCTTGGCCCCTCCCCAAAATGTTTGCAGT
GTTATTTTTGTGGGTTTTTTTTTAACACCCTGACACCTGTTGTGGACATTGTCAACCTTT
GTAAGAAAACCCAAATAAAAATTGAAAAATAAAATAAAAAGAAACCCATGAACATTC
GCACCACTTGTGGCTTCTGACTATCTTCCACAGAGGGAAGTTTAAAACCCAAACTTCC
AAAGGTTTGAACTACCTCAAGACACTTTCGCAGTGGAGTCGTAGACCAATCCCA (SEQ ID NO. 154)

TAAATAAATTAAAAAACTATTAAACCTAAAAACGTCCACCAAACCCTAAAACCATTAA
ACAACCAACAAACCCACTAACAATTAAACCTAAACCTCCATAAATAGGTGAAGGCTTT
AATGCTAACCCAAGACAACCAACCAAAAATAATGAACTTAAAACAAAAATA (SEQ ID NO. 155)

GGTAAAGGGGACCTGGAGAACGCCTTCCTGAACCTGGTCCAGTGCATCCAGAACAAG
CCCCTGTACTTCGCTGACCGGCTGTACGACTCCATGAAGGGCAAGGGGACTCGAGACA
AGGTCTGATTAGAATCATGGTCTCTCGCAGTGAAGTGGACATGCTGAAAATCAGATCT
GAATTCAAGAGGAATATGGCAAGTCCTGTACTACTACAT (SEQ ID NO. 156)

AGAGCAGCAGGCCAGCTGTACTTGGTTTGGCAAGAAAAAGAAGCAGTACAAAGATAA
ATATTTGGCAAAGCACAACGCAGTGTTTGATCAATTAGATCTTGTCACATATGAAGAA
GTAGTCAAACTGCCAGCATTCAAAAGGAAAACATTAGTCTTATTAGGTGCACATGGTG
TTGGAAGAAGACACATAAAAAATACCCTCATCACAAAGCAC (SEQ ID NO. 157)

FIG. 12MM

TCGGTCATAGTAGTAAGGGAAATCTCCCAGGTAAGATGAATACTGCGGTAGGACGAA
CAATCCTCCAGGATGTTTGTTCCATATTAAACTGTTACGTGATATGTGCTTGAATATTC
TGTCCTGAATAATCTCTAGTGTAGTTAATACAATCTTCTCAACTGAAGAAAAATAAGC
CTCCCACAAGAACTGTGTCTGCTGTCTAAGTGCTAGGATTTTATCCTGATGAATAGACC
TGATTGTAGAAGGAATCTGTAATAGCAATCTCTCATCGCCTATGACCGAAAGCCGAAT
TCTGCAGATATCCATCACACTGGCCGGCCGCTCGAGCATCGATCTAGAGGG (SEQ ID NO. 158)

CTGCTTGATGACAAAGGGTGTAGTCTTCATCTTTTCCTGGATTATTTTGGAAGTGACAG
GTGGAAATTCCATCGTCACGTTTATGTGGTCTGTAAAGCCAACGATCTCAAATTCTGG
CGGCTCAAGAGGAGCGTTTGCAGGCACGATGTAGTCTGAGCAGCGGCACACGGTCAA
GTCCCCTCTGTGCACTATGACGATGGCGACGACGTAGCTCTCCATGCCCTCCAACCAC
TTATCTGTCACGTCACATGATGACTTCGTGGTATCTGAACAGTTCTTAACCTTCGTCAG
ATTTTCGTCTTT (SEQ ID NO. 159)

AAATCGTTGCTTCAGAAAGACTCAATAACACTTACTTGTGCCTGGCTGTGCTGACAGT
ACATTCTGTGTCATTTTCCTTCATGGGCGGAACAGTCCACAGAGCTCACCAACAAGTA
CTCCAAAACTGAGCAAGAGTTTAAGCTTCGAGATGCAACCAGATGAGCTTCTAGAAAA
GCCCATGTCTCCCATGCAGTACGCACGGTCTGGACTAGGGACAGCAGAGATGAATGGC
AAACTCATAGCTGCAGGTGGTTATAACAGAGAGGAATGTCTTCGAACAGTTGAATGCT
ATGATCCACATACAGATCACTGGTCCTTCCTTGCTCCCATGAGAACATCAAGCAG (SEQ ID NO. 160)

CTTTCCGAAGAGCACACCCTCCTCTCAATGAGCTTGTGAGGTCTCTTTCTTCTCTTCCT
TCCAACGTGGTGCTAGCTCCAGGCGAGCGACGTGAGAGTGCCACCTGAGACAGACAC
CTTGGTCTCAGTTAGAAGGAAGATGCAGGTCTAAGAGGAATCCCCGCAGGTCTGTCTG
AGCTGTGATCAAGAATATTCCGCAATGTGCCTTTTCTGAGATCGTGTTAGCTCCAAAG

FIG. 12NN

CTTTTTCCTATCGCAGAGTGTTCAGTTTGTGTTTGTTTGTTTTTGTTTTGTTTTGTTTTTC
CCTTGGCGGATTTCCCGTGTGT (SEQ ID NO. 161)

CCTATTGAACGGTCTTGCAATGACGAGCATTCAGATGCTTAAGGAAAGCATTGCTGCT
ACAAATATTTCTATTTTTAGAAAGGGTTTTTATGGACCAATGCCCCAGTTGTCAGTCAA
AGCCGTTGGTGTTTTCATTGTTTAAAATGTCACCTATAAAACGGGCATTATTTATGTTT
TTTTTCCCTTTGTTCATATTCTTTTGCATTCCTGATTATTGTATGTATCGTGTAAAGGAA
GTCTGTA (SEQ ID NO. 162)

CCTATTGAACGGTCTTGCAATGACGAGCATTCAGATGCTTAAGGAAAGCATTGCTGCT
ACAAATATTTCTATTTTTAGAAAGGGTTTTTATGGACCAATGCCCCAGTTGTCAGTCAA
AGCCGTTGGTGTTTTCATTGTTTAAAATGTCACCTATAAAACGGGCATTATTTATGTTT
TTTTTCCCTTTGTTCATATTCTTTTGCATTCCTGATTATTGTATGTATCGTGTAAAGGAA
GTCTGTA (SEQ ID NO. 163)

CCTGGGTCCGTCCTCCAACCCCTCACGCCCAAACCCTCCGACTTTCACTTCTTGAAGTG
ATCGGAAAGGGCAGTTTTGGAAAGGTTCTTCTGGCTAGGCACAAGGCAGAAGAAGTA
TTCTATGCAGTCAAAGTTTTACAGAAGAAGCCATCCTGAAGAAGAAAGGAAGGAAGC
ATATTATGTCAGAGCGGAATGTTCTGTTGAAGAATGTGAAGCACCCTTTCCTGGTGGG
CCTTCACTTCTCATTCCAGACCGCTGACAAGCTCT (SEQ ID NO. 164)

GATGCTGAACACAAAAAGAAAGAAGAAAAGGAAGAGGAGGAGCAAGAGAAGCTGAA
GGGAGGGAGCCTTGGCGAAAATCAGATCAAAGATGAGAAGATTAAAAAGGACAAAG
AGCCCAAAGAAGAGTCAAGAGCTTCTTGGATAGAAAGAAAGGATTTACAGAGTGAGG
CGCAGAATGGAGATTCATGACCCACAAACTTAAAC
(SEQ ID NO. 165)

FIG. 12OO

AAAGCCAATTGGTAGAGAAATTGAAGACACAAATGCTGGATCAGGAAGAGCTTCTGG
CATCAACCAGAAGGGATCAAGATAATATGCAAGCTGAACTGAATCGCCTCCAAGCAG
AAAATGATGCTTCTAAAGAAGAGTAAAGAGTTTTACAGGCCTTAGAGGACTGCTGTTA
ATTATGATCAGAGTTCAGGAGTTAAGAC (SEQ ID NO. 166)

CTGCTTGATGTCCTGTGTAGCGAATGTCACAGCGTACAACATTGTTAGTGTAGTCTGAT
TCAGGCACCAGGTAGCTGGGGTTTACACTGACCTTTAGAATGTAGTTTCCAGGTTGTA
CATCTGTAATATCAATCCACTGGCAGTCTATGTCTGCCGCATAGGTGTCATAACATCCA
GGACTCAATCCCTGTGTGTGTGCAGTGCACGCAAAGGCCCTGTGGTACCCATAGTCAC
AGGACGTGTCCTCCAGACAGAAGCTTGCTTTGTGGCCTTCAGCCACTCTCCTCTGTGTG
TTGGCATCAACGAGAAGCCGAATTCTCGAGATATCCATCACACT (SEQ ID NO. 167)

CTGCTTGATGTCCTGTGTAGCGAATGTCACAGCGTACAACATTGTTAGTGTAGTCTGAT
TCAGGCACCAGGTAGCTGGGGTTTACACTGACCTTTAGAATGTAGTTTCCAGGTTGTA
CATCTGTAATATCAATCCACTGGCAGTCTATGTCTGCCGCATAGGTGTCATAACATCCA
GGACTCAATCCCTGTGTGTGTGCAGTGCACGCAAAGGCCCTGTGGTACCCATAGTCAC
AGGACGTGTCCTCCAGACAGAAGCTTGCTTTGTGGCCTTCAGCCACTCTCCTCTGTGTG
TTGGCATCAACGAGAAGCCGAATTCTCGAGATATCCATCACACT (SEQ ID NO. 168)

GATCTGACACTACAGCATGAGCGTTAGATTTCATAAAATTATTTTTCTTCTAAATGCTG
GAAACTCTAAGGGTTTATTCAGAAAAAAAACTGGCCAATTTTCAAATGGCTTAGAAGC
AGGGTTAATTAAGTATTGAATGAGCCACTGTGATATCCTGATGACACCCAGTCACAAT
GACAGTTTTGAAGCATACAACCAAAACAATTGAGATCTCAAAACTATTTTACATCACT
TATGGTAATGTTATGTAAAAATGAAAATGCTTTCTGTGGAAGTTACATTCTTTACCAGG
TCTTTAACATAAATTAACACGACGTCGAGTAAGCCTTTGTTCGGAAGACAAACTAGTT
TGTGAGTTCAGTCAGATCCCAGCT (SEQ ID NO. 169)

FIG. 12PP

AGTTGCCAGGACCACCACCATAGTTGCCAGGTTCATCATAAACAAATCCAACATCAAT
CTTAAATTCCCCCATCAGACAATCTGCCCTCAAAGAATGGGAATTATAAACCCGGATA
CTGATGATCTCATCCATGAGCTCAGAGGGTGTGATGTGCACATTGTAGAAAAATAACT
CGTCAAAAAACGGATTGTTCCCTCTCTTGATTCTCGTGCGATGCGTCTGACCACAGATG
TGAACTTTCACCACGGGCCTTATGTTGTTGCCGCATAACTGACGGCCCTCGATCACTCT
GACACGGATCTGGAAATCTGTGGCTTGTTGGACAGCATCCTT (SEQ ID NO. 170)

AAGCCGTGTCCCAAAGAATGGATAGAGACGCGATCAGATGCGACAGTGCTGTGGAGA
AAGCCCAGGAACCTGCACAATTGCCCTGGTCCAATGGCTCGTGGATCAGGTTGGGCCA
CTTCTCTGAAGCTTCAAAGGCAGTGGGTAGCACTTCCCCTTGGCCCAGCACCGTATAA
ATCTCATTCATATTCATGACAGTGGAGGATGGGCGGATTGTGCCCAGGCGGTACGGAA
TGCCCTCATCCAGGGTCATGCCCCAGAAGGCACTGTGGTTCCCAGCCTGCCACCCGTA
GTTGCCTCGGTTGATGGCTTTAATCATGTCTGGTCACTAGACACGGCTTAAGCGAATCT
CGAGATATCCATCACACTGGCGGCGTCGAGAT (SEQ ID NO. 171)

AAGCCGTGTCTGATGATGGAGGTAGTGGTGGGGGAGGAGGGACTGAGGGTCCTGAGG
TGGTGGCCCCTGGAACTGATCCCACATAGTTACCCACTGCTAGTTCTGACCCCGTGGA
CAACGTGCCAGAGGCCATGACTGGCAGTATGGCAATGTCCCCATCCCCTTTCTTCTTA
ATTTTAATGGTCCCTTGTTTCTCCAGTTCGTGAATCTTTTTTTCCAGGGTAGACTGTCTT
TGAATGGCTTCTTCCTTTTCTTTGACCATTTTTCTTAACGTGTGAACTTGGGTATTTGCA
TCTTTGTAGATTTCCGGACAACATCAGTTCCTTATTCCTCTGCATAAGTTGCTTTCAGTT (SEQ ID NO. 172)

CGAGTCAGACACATGAAAGCAAAACGCGGGCAGATAAAACGATCGCCTTACCTTCTA
GCAAAAATCTGAAGCTTGTGTCAGAAACAAAGACTCAGAAAGGTTTGTTTTCAGATGA
AGAAGACTCTGAGGATTTGTTTTCTTCTCAAAGTTCAAGTAAGCCAAAAAGTGCATCA

FIG. 12QQ

CTTTCATCCAGCCAGCCCCCAACATCAGTCTCCCTTTTTGGTGATGAAGATGAAGAGG
ACAGTCTTTTTGGGAGTGCAGCAGCTAAGAAGCAGACTTCATCTCTACAACCTCAGAG
TCAAGAGAAAGCAAAGCCTTCCGAGCAGCCCTCAAAGAAGACATCTGCCTTGTTGTTC
AGA (SEQ ID NO. 173)

CGAGTCAGACTTAATTTAAAAACGAAACAAAACAAAAATAACATAGTTTAGAAATCA
AGGAGAAAGGACAGATAGTCTAAGAAAAAAGACAACACAAAAGAGGGGCAGGGCGG
CCAGCTTGCATCAGGGATCTTGGCTGGAGACCTGCTTTGAATAGGTTTCTTGCAGGTAT
TTCTTAAATGCTGTGGGGTTTTTCCAGAGTTCCGCAGCGTGTGTGTTCAAAGGGCTATC
GATGTTGGGTTCTCCTAGCAGGCTCTGGATAGAGAGCAAGATAGTCCTGACATCATAT
AGTGCAGACCACTTATCCTTGAGGATGTCCGGCAGATGTTGCCTGGGTGTCACGTTGG
GGTGGTAGCAGGGTGTGAGGAACTTCACTG (SEQ ID NO. 174)

CGAGTCAGACACTCCTGGCTCCTGGATTCTTTAGATGCCTCCATCAGACTGGGTACTTT
AGATGCCTCCATCAGACTACTTCGTCATTGTATTTCTCAGTTCGCTCAGGGCAAGCGGC
AGTCTCTGGGCTGCTGTGGCAGGTGCCACCACTGCATTTAAAAGTTAAAATTTCTTCA
AATATTCCCATCAAGGCCTTGTAGCCTCTGAGATTGGTTTACTATTTGCCCAGTTATTT
AAAGCTCTCTGCATTCCTTCCTGATTTAATATTGCTATGGCCAGGACAATGTGTAGAAG
TAAAAAGGATATCATATTTACAGGTGTAACGC (SEQ ID NO. 175)

FIG. 12RR

| DD-PCR PRIMER AND PCR SIZE (nt) | cDNA FROM CELL LINE | MOUSE HOMOLOGY (%nt) | HUMAN HOMOLOGY (%nt) | NORTHERN (P-MT) (SCREEN 1) | NORTHERN-CLONED DNA (P-MT) (SCREEN 2) |
|---|---|---|---|---|---|
| .P17-6 cl10 (1100) | 151-1 LM1 | MUSCLE NICOTINIC ACETYLCHOLINE RECEPTOR APLHA (54.3%) | | NO | 151-1LM1 UP, 151-1LMA DOWN |
| P19-6 cl2 (500) | 151-2 PA | | LYMPHOCYTE IgE RECEPTOR (52.6%) | NO | 151-2LMA DOWN,DOWN |
| P21-6 cl3 (450) | 151-2 PA | HISTON H2b (94.2%) | | 151-1LM1 DOWN,DOWN | 151-1LM1 DOWN,DOWN |
| P21-9 cl6 (500) | 151-1 PB | RATTUS NORVEGICUS THIOL- SPECIFIC ANTIOXIDANT mRNA(94.4.%) | | 151-1LM1 DOWN,DOWN 151-2LMA UP,UP | 151-1LM1 DOWN,DOWN 151-2LMA UP,UP |
| P21-17 cl9 (1000) | 148-1 LMD | MUS MUSCULUS PUTATIVE PROTEIN TYROSIN PHOSPHATASE mRNA(98.3%) | | 148-1LMD UP,UP 151-1LM1 UP,UP | 148-1LMD UP,UP 151-1LM1 UP,UP |
| P22-5 cl3 (600) | 148-1 LMD | RAT DIHYDROPYRIDINE-SENSITIVE L-TYPE CALCIUM CHANNEL ALPHA-2 SUBUNIT GENE (92.5%) | | 148-1LMD UP,UP | 148-1LMD UP,UP |

FIG. 13A-I

| | | | | | |
|---|---|---|---|---|---|
| P22-6 cl4 (600) | 148-1 LMD | SAME AS P22-5 Cl3 | | 148-1LMD UP<br>151-1LM1 UP | 148-1LMD UP,UP |
| P22-9 cl3 (800) | 148-1 LMD | RAT KIDNEY ZN-PEPTIDASE AMINOPEPTIDASE N mRNA (90.5%) | | 148-1LMD UP,UP,UP | 148-1LMD UP,UP,UP |
| P24-6 cl3 (550) | 151-1 PB | | UBIQULTIN CARRIER PROTEIN (E2-EPF) mRNA (53.3%) | 151-1LM1 DOWN<br>151-2LMA UP<br>151-2LMB UP | 151-2LMA UP |
| P24-10 cl3 (1400) | 151-1 LM1 | RATTUS NORVEGICUS CALPAIN I1 80 kDa SUBUNIT mRNA (93%) | | 151-1LM1 UP,UP | 151-1LM1 UP,UP |
| P25-1 cl3 (400) | 148-1 PA | M. MUSCULUS KERATINOCYTE GROWTH FACTOR Fgf-7 (99.4%) | | 148-1LMD DOWN<br>151-1LM1 DOWN,DOWN<br>151-2LMB UP,UP<br>151-2MMA UP | 148-1LMD DOWN<br>151-1LM1 DOWN<br>151-2LMB UP<br>151-2LMMA UP |
| P25-9 cl8 (1300) | 151-1 PB | M. MUSCULUS mRNA FOR INSULIN-LIKE GROWTH FACTOR BINDING PROTEIN-3(98.1%) | | 148-1LMD UP<br>151-1LM1 DOWN,DOWN,DOWN<br>151-2LMA UP,UP,UP | 148-1LMD UP<br>151-1LM1 DOWN,DOWN,DOWN<br>151-2LMA UP,UP,UP |
| P2-27 (cl18-3) | 148-1 PA | RATTUS NORVEGLUS GLYPICAN mRNA (93.4%) | | | 148-1LMD DOWN<br>P53(+)12 DOWN |

FIG. 13A-2

| CLONE # | cDNA FROM CELL LINES | DD PRIMER | PCR SIZE (nt) | MOUSE HOMOLOGY | HUMAN HOMOLOGY | NORTHERN BIG BIOT # | REGULATION TYPE | SEQUENCING PRIMER | SEQUENCING LENGTH |
|---|---|---|---|---|---|---|---|---|---|
| CI 3#1<br>CI 4#1<br>(SAME FRAG & ORIENTATION | 151-2 LMB | P3 | | TYROSINE KINASE? VIP2 | CAVEOLIN (70%) | N123<br>148-1 UP<br>151-1 UP<br>151-2 UP | UP | -40 | 241<br>156 |
| CI 5A#4 | 148-1 PA | P2 | | THROMBO-SPONDIN 100% | THROMBO-SPONDIN | N124<br>148-1 DOWN<br>151-1 DOWN<br>151-2 UP | DOWN | -40 | 233 |
| CI 25#3 | 151-2 LMA | P5 | | | 53BP2 P53-BINDING PROTEIN (53.3%) | 148-1 DOWN<br>151-1 DOWN<br>151-2 UP | DOWN | | |
| CI 29#3<br>CI 28#1<br>(SAME FRAG; DIFFERENT ORIENTATION | 148-1 LMD | P5 | 335<br>332 | | TGF-BETA 2 (53.0.%)<br>Kvi-1 nmls(53.0%) | N119<br>148-1 UP<br>151-1 UP<br>151-2 UP | UP | T7 | 335<br>332 |
| CI 54A#2 | 141-1 PA | P8 | | MUSCULUS RECEPTOR TYROSIN KINASE CYCLIN G | PROTO-ONCOGENE TYROSINE PROTEIN KINASE GENE | N126<br>148-1 DOWN (WEAK)<br>151-1 DOWN (WEAK)<br>151-2 UP (WEAK) | DOWN | Sp6 | 220 |

FIG. 13B-1

FIG. 13B-2

| | | | | | | | | | |
|---|---|---|---|---|---|---|---|---|---|
| CI 63#4 | 151-2 LMA | P10 | | | Y316 GENE (53.8%) 1AC GENE (53.8%) Rb SUSCEPTI-BILITY GENE (50%) | N127 | UP | Sp6 | 340 |
| CI 74#2 | 151-2 LMA | P11#3 | | 86.8% SERUM & GLUCOCORTICOID REGULATED KINASE (sgk) | | N120 148-1 UP 151-1 DOWN 151-2 UP | | Sp6 | 320 |
| CI 75#1 | 151-2 LMA | P11#10 | | 87% MATCH sgk | | | UP | Sp6 | 250 |
| CI 78B#4 MATCH THE SAME GENE BUT DIFF. FRAG. | 148-1 LMD | P12 | | 92.2% MATCH sgk | PROTEIN KINASE C-L (57%) | | | Sp6 | 270 |

| DD-PCR PRIMER AND PCR SIZE (nt) | MOUSE HOMOLOGY(%nt) | HUMAN HOMOLOGY (%nt) | TGF-BETA STIMULATORY RESPONSE (12 hr.) | NORTHERN (P-MT) | CELL LINE |
|---|---|---|---|---|---|
| P11-2 cl5 (310) | LYSYL OXIDASE (100%) | | ⇧⇧⇧ | ⇩⇩ | N132: 148-1 LMD, 151-1 LM1 DOWN, 151-2 LMB, 151-2 LMC UP |
| P20-23 cl9 (850) | ACTIN BINDING PROTEIN(100%) | | ⇧⇧ | ⇧⇧ | N142: 148-1 LMD, 151-2 LMA,LMB,MMA UP, 151-1 LM1 UNCHANGED |
| C129-3 (P5) (335) | | NMB(79.8%) | ⇩⇩ | ⇧⇧ | N119: 148-1 LMD 151-1 LM1, 151-2 LMA,LMB,LMC,MMA UP |
| P17-3 cl8 (1000) | UBIQUITIN ACTIVATING ENZYME E1(100%) | | ⇧ | ⇩⇩ | N142: 151-2 LMA DOWN |
| P20-3 (400) | | ALPHA ACTININ 3 mRNA (77.5%) | ⇧⇧ | | |
| P18-12 cl3 (1000) | RAT mRNA FOR P34 PROTEIN (89.6%) | | ⇧ | | |
| P25-7 cl3 (1000) | M.MUSCULUS mRNA FOR P19-PROTEIN TYROSINE PHOSPHATASE (100%) | | ⇧ | ⇧⇧ | 148-1IMD UP |
| P19-1 cl3 (310) | | POLYMORPHIC LOCI IN Xq28 (30%) | ⇧ | | |

FIG. 13C

| DD-PCR PRIMER AND PCR SIZE (nt) | MOUSE (RODENT) HOMOLOGY (%nt) | HUMAN HOMOLOGY (%nt) | SCREEN 1 P53 STIMULATORY RESPONSE (12h. OR 24h.) | SCREEN 2 CLONED DNA |
|---|---|---|---|---|
| P1-8 cl10 (1000) | | DYSTROPHIN GENE (50.4%) | P53(+)24 DOWN,DOWN | P53(+)24 DOWN,DOWN |
| P1-9 cl10 (500) | M.MUSCULUS mRNA FOR CYCLIN G (96.5%) | | P53(+)12 UP,UP P53(+)24 UP,UP,UP | P53(+)12 UP,UP,UP P53(+)24 UP,UP,UP |
| P7-4 cl1 (600) | RATTUS NORVEGLOUS SGK mRNA (51.3%), RAT LUNG DERIVED L01 C-ros-1 PROTO-ONCOGENE mRNA (48.4%) | NITRIC OXIDE SYNTHASE (47.1%) | 148-1LMD DOWN P53(+)12 UP,UP P53(+)24 UP,UP,UP | P53(+)12 UP P53(+)24 UP |
| P9-17 cl9 (500) | RAT mRNA FOR CYCLIN D1 (79.1%) | | P53(+)24 UP | P53(+)24 UP |
| P9-20 cl3 (850) | | H. SAPIENS LDLC mRNA (51.8%) | P53(+)12 DOWN P53(+)24 DOWN,DOWN | P53(+)24 DOWN |
| P11-23 cl2 (800) | SYRIAN HAMSTER GENE FOR CYTOCHROME P-4 (52.5%), RAT CARBOHYDRATE BINDING RECEPTOR GENE (50.6%) | | P53(+)24 UP,UP | P53(+)24 UP |
| P15-9 cl1 (600) | MOUSE (CLONE BALB11N) mRNA (47.2%) | PTGS2 GENE FOR PROSTAGLANDIN ENDOPEROXIDE SYNTHASE-2 (46.6%) | P53(+)24 DOWN | P53(+)24 DOWN,DOWN |
| P15-14 cl5 (500) | | | P53(+)12 UP P53(+)24 UP | P53(+)24 UP |
| P18-23 cl10 (500) | | | 148-1LMD DOWN P53(+)12 DOWN P53(+)24 DOWN | 148-1LMD DOWN P53(+)12 DOWN P53(+)24 DOWN |

FIG. 13D

METHOD FOR IDENTIFYING METASTATIC SEQUENCES

Matter enclosed in heavy brackets [ ] appears in the original patent but forms no part of this reissue specification; matter printed in italics indicates the additions made by reissue.

REFERENCE TO RELATED APPLICATION

[This patent application is a continuation of] *This application is a continuation of U.S. application Ser. No. 09/469,316, filed Dec. 22, 1999, which is a broadening Reissue Application of U.S. Pat. No. 5,783,182, issued Jul. 21, 1998. The patent application issuing as U.S. Pat. No. 5,783,182 claims priority on* United States provisional patent application, serial number 60/006,838, filed Nov. 16, 1995.

*More than one reissue application has been filed for the reissue of U.S. Pat. No. 5,783,182. Application Ser. No. 09/469,316, filed, now abandoned, is a reissue application of U.S. Pat. No. 5,783,182. Application Ser. No. 09/977,371, filed Oct. 16, 2001, is a continuation of Ser. No. 09/469,316 and a reissue of U.S. Pat. No. 5,783,182. Application Ser. No. 09/985,799, filed Nov. 16, 2001, is a continuation of Ser. No. 09/977,371 and a reissue of U.S. Pat. No. 5,783,182.*

RIGHTS IN THE INVENTION

This invention was made in part with United States Government support under grant number CA350129, awarded by the National Cancer Institute, National Institute of Health and the United States Government has certain rights in the invention.

BACKGROUND

1. Field of the Invention

The present invention relates to methods for the identification and isolation of metastatic sequences, to diagnostic probes and kits which contain metastatic sequences and to therapeutic treatments for neoplastic disorders based on metastatic sequences.

2. Description of the Background

The development of higher organisms is characterized by an exquisite pattern of temporal and spatially regulated cell division. Disruptions in the normal physiology of cell division are almost invariably detrimental. One such type of disruption is cancer, a disease that can arise from a series of genetic events.

Cancer cells are defined by two heritable properties, uncontrolled growth and uncontrolled invasion of normal tissue. A cancerous cell can divide in defiance of the normal growth constraints in a cell leading to a localized growth or tumor. In addition, some cancer cells also gain the ability to migrate away from their initial site and invade other healthy tissues in a patient. It is the combination of these two features that make a cancer cell especially dangerous.

An isolated abnormal cell population that grows uncontrollably will give rise to a tumor or neoplasm. As long as the neoplasm remains in a single location, it is said to be benign, and a complete cure may be expected by removing the mass surgically. A tumor or neoplasm is counted as a cancer if it is malignant, that is, if its cells have the ability to invade surrounding tissue. True malignancy begins when the cells cross the basal lamina and begin to invade the underlying connective tissue. Malignancy occurs when the cells gain the ability to detach from the main tumor mass, enter the bloodstream or lymphatic vessels, and form secondary tumors or metastases at other sites in the body. The more widely a tumor metastasizes, the harder it is to eradicate and treat.

As determined from epidermiological and clinical studies, most cancers develop in slow stages from mildly benign into malignant neoplasms. Malignant cancer usually begins as a benign localized cell population with abnormal growth characteristic called a dysplasia. The abnormal cells acquire abnormal growth characteristics resulting in a neoplasia characterized as a cell population of localized growth and swelling. If untreated, the neoplasia in situ may progress into a malignant neoplasia. Several years, or tens of years may elapse from the first sign of dysplasia to the onset of full blown malignant cancer. This characteristic process is observed in a number of cancers. Prostate cancer provides one of the more clear examples of the progression of normal tissue to benign neoplasm to malignant neoplasm.

The walnut-sized prostate is an encapsulated organ of the mammalian male urogenital system. Located at the base of the bladder, the prostate is partitioned into zones referred to as the central, peripheral and transitional zones, all of which surround the urethra. Histologically, the prostate is a highly microvascularized gland comprising fairly large glandular spaces lined with epithelium which, along with the seminal vesicles, supply the majority of fluid to the male ejaculate. As an endocrine-dependent organ, the prostate responds to both the major male hormone, testosterone, and the major female hormones, estrogen and progesterone. Testicular androgen is considered important for prostate growth and development because, in both humans and other animals, castration leads to prostate atrophy and, in most cases, an absence of any incidence of prostatic carcinoma.

The major neoplastic disorders of the prostate are benign enlargement of the prostate, also called benign prostatic hyperplasia (BPH), and prostatic carcinoma; a type of neoplasia. BPH is very common in men over the age of 50. It is characterized by the presence of a number of large distinct nodules in the periurethral area of the prostate. Although benign and not malignant, these nodules can produce obstruction of the urethra causing nocturia, hesitancy to void, and difficulty in starting and stopping a urine stream upon voiding the bladder. Left untreated, a percentage of these prostate hyperplasia and neoplasias may develop into malignant prostate carcinoma.

In its more aggressive form, transformed prostatic tissues escape from the prostate capsule and metastasize invading locally and throughout the bloodstream and lymphatic system. Metastasis, defined as tumor implants which are discontinuous with the primary tumor, can occur through direct seeding, lymphatic spread and hematogenous spread. All three routes have been found to occur with prostatic carcinoma. Local invasions typically involve the seminal vesicles, the base of the urinary bladder, and the urethra. Direct seeding occurs when a malignant neoplasm penetrates a natural open field such as the peritoneal, pleural or pericardial cavities. Cells seed along the surfaces of various organs and tissues within the cavity or can simply fill the cavity spaces. Hematogenous spread is typical of sarcomas and carcinomas. Hematogenous spread of prostatic carcinoma occurs primarily to the bones, but can include massive visceral invasion as well. It has been estimated that about 60% of newly diagnosed prostate cancer patients will have metastases at the time of initial diagnosis.

Surgery or radiotherapy is the treatment of choice for early prostatic neoplasia. Surgery involves complete removal of the entire prostate (radical prostatectomy), and often removal of the surrounding lymph nodes, lymphadenectomy. Radiotherapy, occasionally used as adjuvant therapy, may be either external or interstitial using $^{125}$I. Endocrine therapy is the treatment of choice for more advanced forms. The aim of this therapy is to deprive the prostate cells, and presumably the transformed prostate cells as well, of testosterone. This is accomplished by orchiectomy (castration) or administration of estrogens or synthetic hormones which are agonists of luteinizing hormone-releasing hormone. These cellular messengers directly inhibit testicular and organ synthesis and suppress luteinizing hormone secretion which in turn leads to reduced testosterone secretion by the testes. Despite the advances made in achieving a pharmacologic orchiectomy, the survival rates for those with late stage carcinomas are rather bleak.

SUMMARY OF THE INVENTION

The present invention overcomes the problems and disadvantages associated with current strategies and designs and provides new methods for the identification of sequences related to metastasis.

One embodiment of the invention is directed to methods for the identification of a metastatic sequence. One or more oncogenic sequences are transfected into a cell to form a transfected cell. The transfected cell is introduced into a primary site of a host animal to establish a colony which is incubated in the animal for a period of time sufficient to develop both a primary tumor and a metastatic tumor. Expressed sequences are harvested from the primary tumor and the metastasis. Harvested sequences are compared to each other and to non-metastatic cells to identify sequences related to metastasis. Dominant metastatic genes are genes whose expression leads to metastasis. Such genes are typically expressed at high levels in metastatic cells and not significantly expressed in normal or nonmetastatic cells. Recessive metastatic genes, genes whose expression prevents metastasis, may be selectively expressed in normal and nonmetastatic cells and absent in metastatic cells. Dominant and recessive metastatic genes may act directly or act pleiotropically by enhancing or inhibiting the expression or function of other dominant and recessive metastatic genes.

Another embodiment of the invention is directed to methods for identifying metastatic sequences. A mammalian cell is treated with a metastatic agent and the treated cell is implanted into a primary site of a host mammal. The host animal is maintained for a period of time sufficient for the cells to proliferate and to develop a [metastatsis] *metastasis* at a secondary [cite] *site*. Expressed squences from cells of the primary cite and cells of the secondary site are reverse transcribed into cDNA by differential display polymerase chain reaction to identify differentially expressed sequences.

Another embodiment of the invention is directed to sequences isolated by the methods of the invention. Sequences may be in the form of DNA, RNA or PNA. The nucleic acid may be single-stranded or double-stranded. Single stranded nucleic acid may be in the form of a sense strand or an antisense strand. In addition, the sequence may be part of a homologous recombination vector designed to recombine with another metastatic sequence.

Another embodiment of the invention is directed to a method for treating a neoplastic disorder comprising administering a pharmaceutically effective amount of a metastatic nucleic acid to a patient. The nucleic acid may be single-stranded in the sense or the antisense direction. Alternatively, the nucleic acid may be packaged in a viral vector such as, for example, a retroviral, a vaccinia or an adenoviral vector. Administration may be performed by injection, pulmonary absorption, topical application or delayed release of the nucleic acid along with a pharmaceutically acceptable carrier such as water, alcohols, salts, oils, fatty acids, saccharides, polysaccharides and combinations thereof.

Another embodiment of the invention is directed to a kit for detecting [of] the presence or absence of a metastatic sequence.

Other objects and advantages of the invention are set forth in part in the description which follows, and in part, will be obvious from this description, or may be learned from the practice of the invention.

FIG. A-RR 12 Nucleotide sequences of metastatic nucleic acids.

FIG. 13 A–D Characterization of metastatic sequences isolated.

Figure 14A:
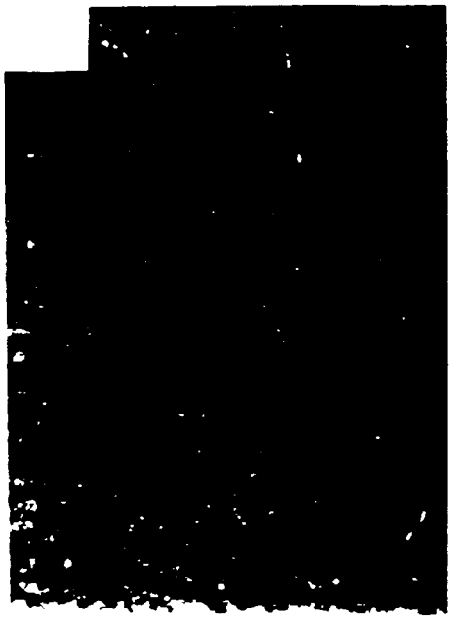
Figure 14B:
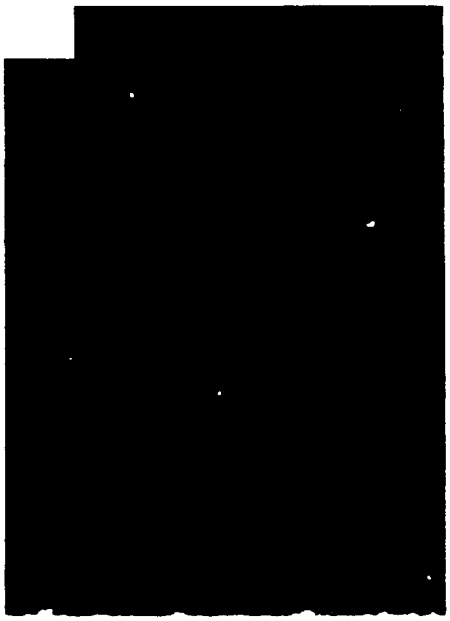

FIG. 14 Immunohistological staining of primary and metastatic human prostate tumors using anti-caveolin antibodies.

DESCRIPTION OF THE INVENTION

As embodied and broadly described herein, the present invention is directed to methods for identifying metastatic sequences, to the metastatic sequences identified, to methods for the detection, diagnosis and treatment of disorders related to metastasis, and to diagnostic kits which comprise these sequences.

Figure 1A:
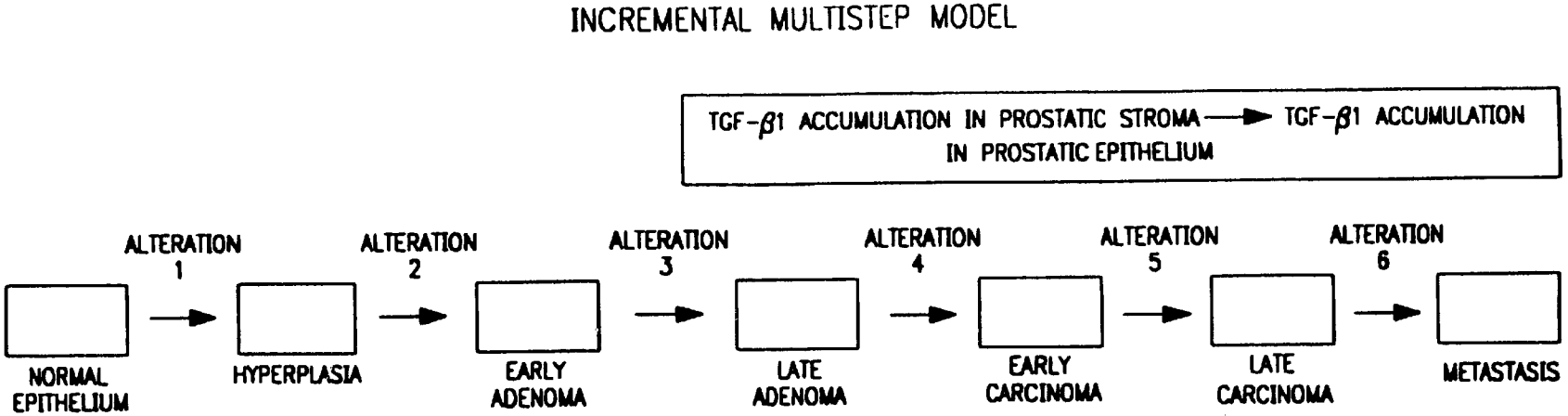
FIG. 1 Schematic showing two paths in the multistep progression to cancer.
Figure 1B:
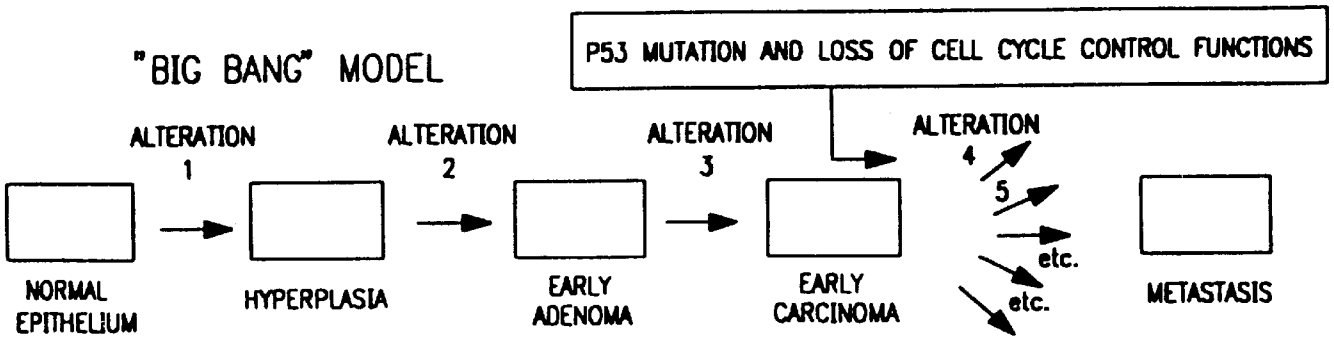

The ability of cancers to metastasize makes tumors difficult to eradicate by any means. Malignant cancer involves a multistage progression from, for example, normal tissue through hyperplasia, early adenoma, early carcinoma and finally to a metastatic tumor (FIG. 1). Cells of a typical tumor loosen their adhesion to their original cellular neighbors and cross the basal lamina and endothelial lining to enter the body's circulation. Once in circulation, the metastatic cell exits from the circulation to disseminate throughout *the* body and proliferate in a new environment.

Like the initial oncogenic event, the ability of a cell to metastasize requires additional mutationic or epigenetic changes. An understanding of the molecular mechanisms of metastasis allow for the design of treatments to inhibit metastasis. Knowledge of stage specific gene expression for neoplastic disorders allows for early detection and typing of tumors. With early detection and typing, proper treatment may be administered to a patient with the neoplastic disorder earlier, which will lead to a higher probability of a complete cure.

For human prostate tumors, the study of stage specific tumors is difficult, if not impossible, as cell lines are extremely difficult to grow and it is rare that tissue becomes available from the primary tumor as well as metastatic disease from the same patient. This problem is exacerbated because of the infrequent biopsy of metastatic deposits in conjuntion with isolation of material from the primary tumor. Furthermore, the growth of cell lines from malignant prostates has proved to be problematic over the last few decades. This is evidenced by the lack of cell lines from prostate cancer obtained under any conditions.

One embodiment of the invention is directed to a method for identifying a metastatic sequence. A mammalian cell is transformed into a pre-neoplastic or neoplastic state or phenotype by transfection with one or more oncogenic sequences. Alternatively, or in addition to transfection, the mammalian cell may be treated with an agent or subjected to a condition that potentiates the metastatic character of the cell or predisposes the cell to metastasis. The transfected or treated cell is implanted into a host animal at a primary site and grown for a period of time sufficient to develop a metastasis at a secondary site. Expressed sequences from cells of the primary site and cells at the secondary site are amplified by differential display polymerase chain reactions. PCR products from these reactions are compared and the metastatic sequence identified by alteration in the levels or patterns of the resulting products.

Mammalian cells from a wide variety of tissue types and species are suitable for transfection or treatment including surgically obtained or primary or immortalized cells and cell lines. Cells may be from humans or primates, mice, rats, sheep, cows, rabbits, horses, pigs or guinea pigs or from transgenic or xenogeneic host mammals. Cells may be obtained from adult, juvenile or fetal tissue, and used directly from the mammal, from cryogenically preserved samples, or after culturing in vitro or in vivo for a period of time. In vitro culturing typically involves tissue culture conditions (e.g. 37° C.; 5% $CO_2$) while in vivo culturing may involve successive passage of cells through host animals such as, for example, mice or rabbits. Cells passed in vivo may be obtained from sites proximal or distal to the site of implantation. The tissue type from which the cells are derived or obtained may be any tissue which is susceptible to transfection or other treatment including, for example, urogenital tissues, epithelial cells, hepatic cells, fibroblasts lymphatic tissues, hematopoietic cells, cells of the immune system, cells of the gastrointestinal system and cells of the nervous system.

Figure 5A:
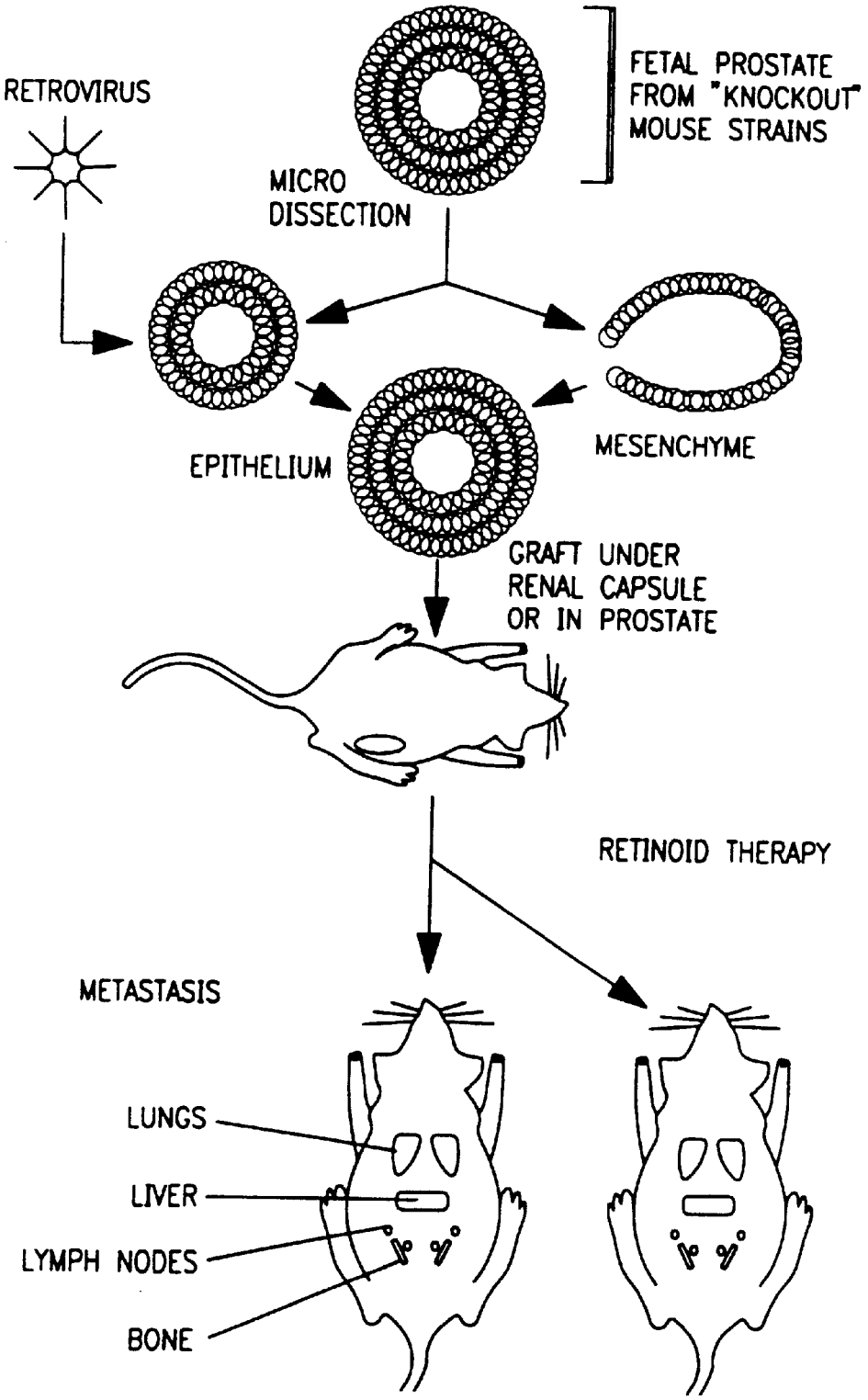
FIG. 5 A–B Schematic showing method to establish a tumor and a metastatic transplant from fetal tissue(A) and from cell lines and tumors (b).

Cell types useful for the identification of metastatic sequences related to prostate cancer include cells and cell lines of the fetal prostate lineage from normal or transgenic animals, and cells from normal or reconstituted prostate tissue. One method of generating reconstituted prostate cells is to isolate fetal prostate tissue and microdissect the fetal prostate epithelium away from fetal mesenchyme. Fetal prostate epithelium may be genetically manipulated before reassociation with fetal mesenchyme (FIG. 5A). Genetic manipulation involves treatment or transfection with a metastatic agent or a nucleic acid sequence that affects neoplastic or metastatic potential of the cell. Reassociation of fetal epithelium and mesenchyme is performed by implanting epithelial tissue within a pocket of mesenchymal tissue. After manipulation, cells are reimplanted into a mammalian host in a similar manner as other cells, such as reimplantation into or under the renal capsule.

Mammalian cells may be transfected by a variety of techniques, all of which are well-known to those of ordinary skill. Direct methods involve the introduction of genetic material into the nucleus of a cell by injection. These techniques include high velocity projectile injection, microinjection, and electroporation. Indirect methods, involving the active or passive uptake of the genetic information by the cell, include transduction with recombinant vectors, and chemical or physical treatments such as calcium phosphate uptake, lipofection or dextran sulfate transfection. Chemical techniques rely on chemical carriers to introduce nucleic acids into a cell. These methods, for example, utilize unilamellar phospholipid vesicles (e.g. liposomes) loaded with DNA (or RNA). The approach relies on the fusion of the DNA containing vesicles with the plasma membrane of the recipient cells. After entry, DNA traverse the cytoplasm and enter the nucleus. Another lipofection technique uses a synthetic cationic lipid such as N-[1-(2,3-dioleyloxy) propyl]-N,N,N-trimethylammonium chloride (DOTMA). DOTMA spontaneously associates with nucleic acids and forms unilamellar vesicles upon sonication. Genetic material is incorporated into these vesicles and subsequently transfected into the cell. Calcium phosphate co-precipitation involves mixing of purified nucleic acid with buffers containing phosphate and calcium chloride which results in the formation of a fine precipitate. Presentation of this precipitate to cells results in incorporation of the nucleic acid into cellular genome. Other chemicals, such as DEAE dextran or polybrene, when present in media with nucleic acids, can also cause the transfection of mammalian cells.

Physical methods of transfection rely on electric fields, needles and particles to enable nucleic acids to traverse the cellular membrane. Electric field mediated DNA transfection, commonly called electroporation, is based on the principle that membranes, when subjected to an electric field, undergo a reversible breakdown resulting in pores large enough to permit the passage of nucleic acids. In micro-projectile mediated gene transfer, micro-projectiles of subcellular dimensions are coated with nucleic acid and propelled at high velocity into a cell using a particle gun. The nucleic acid is introduced into the nucleus directly when the particles impinge upon the nucleus. In microinjection, nucleic acid is injected directly into the nucleus of a cell with a needle. Lasers have also been used to introduce minute holes in cellular membrane to allow introduction of nucleic acids. All these methods may be used for transfection and the selection of the method will depend on the cell type, the desired transfection efficiency and the equipment available.

The efficiency of transfection may be monitored and enhanced by the co-transfection of a selectable marker. If a marker is co-transfected with a genetic construct, positively transformed cells may be separated from nontransformed cells by chemical selection. The efficiency of transfection will be increased in most cases because the chemicals will selectively kill non-transfected cells. The number of transfected cells may also be monitored by analyzing the degree of chemical resistance of the transfected cells. Markers commonly used for selection purposes include, for example, nucleic acids encoding dihydrofolate reductase, metallothionein, CAD, adenosine deaminase, adenylate deaminase, UMP synthetase, IMP 5'-dehydrogenase, xanthine-guanine phosphoribosyltransferase, mutant thymidine kinase, mutant HGPRTase, thymi dylate synthetase, P-glycoprotein 170, ribonucleotide reductase, glutamine synthetase, asparagine synthetase, arginosuccinate synthetase, ornithine decarboxylase, HMG-CoA reductase, N-acetylglucosaminyl transferase, theronyl-tRNA synthetase, sodium or potassium dependent ATPase or derivatives or mutants of these nucleic acids. Markers may be used individually or in combination. Chemicals useful for selection include methotrexate, cadmium, PALA, Xyl-A, adenosine, 2'-deoxycoformycin, adenine, azaserine, coformycin, 6-azauridine, pyrazofuran, mycophenolic acid, limiting xanthine, hypoxanthine, aminopterin, thymidine, 5-fluorodeoxyuridine, adriamycin, vincristine, colchicine, actinomycin D, puromycin, cytocholasin B, emetine, maytansine, Bakers' antifolate, aphidicolin, methionine sulfoximine, β-aspartyl hydroxamate, albizziin, canavanine, α-difluoromethylornithine, compactin, tunicamycin, borrelidin, ouabain, and derivatives and analogs and combinations of these chemicals. Some chemicals, such as methotrexate, may be used individually while other chemicals, such as HAT (hypoxanthine, aminopterin and thymidine), need to be used in combination to be effective.

The oncogene transfection efficiency, the fraction of live cells tranfected by an oncogene, may be indirectly enhanced by chemical selection for a co-transfected marker. An oncogene is a sequence which can predispose, or induce the cell into a pre-neoplastic or neoplastic condition or otherwise enhance the metastatic potential of the cell. Sequences with these properties are referred to as oncogenes and include abl, ahi, akt, bcl, crk, dsi, erb, ets, evi, fes/fps, fim, fis, fgr, flv, fms, fos, gin, gli, int, jun, kit, mas, lck, met, mil/raf, mis, mlv, mos, myb, myc, neu, onc, pim, raf ras, rel, ros, seq, sis, ski, spi, src, tcl, thy, trk, and yes. Some oncogenes, such as ras, are oncogenic when mutated. Other oncogenes, such as myc, are oncogenic when overexpressed or underexpressed. Many oncogenes represent members of multigene families or homologs families. Homologs are proteins that have similar primary, secondary or tertiary structures. Genes may differ in nucleic acid sequence or encoded peptide sequence and still be homologs when the encoded polypeptides have similar spatial folding. Many oncogenes can be classified into dominant oncogenes and recessive oncogenes. One or more dominant oncogenes can confer a neoplastic or preneoplastic phenotype to a cell. One or more recessive oncogenes, when silenced, may also confer a neoplastic or preneoplastic phenotype. Gene silencing is performed by transfecting cells with nucleic acids which cause genetic ablation or by antisense suppression.

While any oncogene may be used, the preferred oncogenes are those that are normally associated with metastasis such as a metastasis specific gene. Such genes include for example, TGF-β1, Cyclin D1 p21, p34, *mutant* p53, lysyl oxidase, caveolin, actin binding protein, ubiquitin activating enzyme E1, nmb or α-actinin 3. Metastatic-specific genes may be used individually or in combination with other oncogenes.

The metastatic potential of a cell may be altered, for example, by gene ablation [with] *of* a sequence specific for a recessive oncogene. Recessive oncogenes are those genes which encode products which can suppress oncogenesis and metastasis. A gene ablation sequence can be designed to specifically suppress a recessive oncogene. Ablation may include pre-transcriptional inhibition such as homologous recombination with endogenous recessive oncogenes and post transcriptional inhibition such as the expression of antisense oncogenes to suppress translation. Gene ablation sequences may be targeted towards well known recessive oncogenes such as, for example, the retinoblastoma gene (Rb) or [Bcg] *Bcl*. Other candidates for ablation include metastatic genes previously isolated by the invention such as, for example, TGF-β1, cyclin D1, p21, p34, *mutant* p53, lysyl oxidase, caveolin, actin binding protein, ubiquitin activating enzyme E1, nmb or α-actinin-3. The effects of ablating a recessive oncogene may include oncogenesis and metastases.

Alternatively, or in addition to transfection the mammalian cell may be treated with an agent, either before or after transfection, that alters the expression of the cell's nucleic acids. Treatment may comprise contacting the cells with one or more agents which affect the neoplastic predisposition (e.g. neoplastic agents; phorbol esters), metabolization (e.g. metabolic agents), metastasis (e.g. metastatic agents), differentiation (e.g. differentiation agents; retinoic acid), activation or proliferation (e.g. growth factors) of the cell. Agents which can alter gene expression include chemicals such as benzanthracene (BA), dimethyl benzanthracene (DMBA) or 5-azacytidine. Alternatively, treatment may also comprise altered conditions such as hypoxia which involves subjecting a cell to a reduced oxygen content, exposable to radiation or other stresses to the cell.

Treatment may be in vitro or in vivo and may include for example, direct or indirect induction or suppression of well known oncogenic sequences and genes isolated by the invention such as, for example, TGF-β1, Cyclin D1, *mutant* p53, lysyl oxidase, caveolin, actin binding protein, ubiquitin activating enzyme E1, nmb, α actinin 3, and p34. Gene expression induction includes transfecting expression vectors encompassing coding regions of the gene. Gene repression comprises introducing a gene ablation sequence or a repressor of the gene to the cell.

Cells which have one or more genes ablated may also be used. For example, a metastatic suppressor gene may be ablated to prevent inhibition to metastases. A useful gene for ablation is a gene capable of affecting the phenotype and behavior of a cell or tumor. For example, with prostate tumors, suitable genes include both well known genes and genes isolated by the methods of the invention such as for example, TGF-β1, Cyclin D1, p21, p34, *mutant* p53, lysyl oxidase, caveolin, actin binding protein, ubiquitin activating enzyme E1, nmb and α actinin 3. Genetic ablation (gene knockout) refers to a process of silencing the expression of a particular gene in a cell. The silencing process may include, for example, gene targeting or antisense blocking. Gene targeting refers to a process of introducing a nucleic acid construct into a cell to specifically recombine with a target gene. The nucleic acid construct inactivates the targeted gene. Inactivation may be by introduction of termination codons into a coding region or introduction of a repression site into a regulatory sequence. Antisense blocking refers to the incorporation into a cell of expression sequences which directs the synthesis of antisense RNA to block expression of a target gene. Antisense RNA hybridizes to the mRNA of the target gene to inhibit expression.

The host animal is preferably the same species as the implanted cell. In cases of xenogeneic transplants, the host may be immunocompromised genetically or by treatment with drugs such as immunosuppressants. A host may be immunocompromised genetically by breeding such as with nude mice or severe combined immunodeficient (SCID) mice. A host may also be immunocompromised by chemical or irradiation methods. An additional route to immunocompromise a host is to use transgenic technology to introduce an immunosuppressing gene or to introduce a foreign antigen gene. An immunosuppressing gene is a gene that affects the efficiency of the immune system such as a gene which inhibits the formation of cells of the B cell or T cell lineage. A foreign antigen gene, when expressed, may cause the host to tolerate the antigens in a xenogeneic transplant and not mount an immune response.

Cells may be implanted into any primary site in a host animal, such as, for example, subcutaneous implantation, intravenous injection, or implantation into the abdominal cardiac, chest, pulmonary, thoracic or peritoneal cavity. Using techniques known to those of ordinary skill in the art, cells can be placed on or in nearly any organ or tissue. Reasons for choosing a site include ease of implant, proximity of similar tissue type, immunoprivileged position and ease of inspection. Metastasises migrate from the primary site to one or more secondary sites such as, for example, the lung, kidney, liver, lymph nodes, brain, testis, bone, spleen, ovaries or mammary. Preferred sites include the renal capsule, the testes, the prostate and the ovaries.

To avoid histocompatibility problems, the implant may be placed into a histocompatible host animal. Such problems are generally avoided if the implant and host animal are syngeneic. Alternatively, a non-histocompatible host may be used if the host can be made immunotolerant. Hosts may also be transgenic or immunocompromised animals or genetically matched to the mammalian cells to be introduced. Immunocompromised animals may be derived from established mouse lines such as nude mice or severe combined immune deficiency (SCID) mice, or by treatments such as radiation, chemical, pharmaceutical or genetic targeting. Sufficiently immunosuppressed animals can be made tolerant to xenogeneic transplants.

After implantation the host animal is maintained under normal conditions to develop metastases. Alternatively, the host animal may be subjected to an altered treatment or environmental condition to stimulate or repress metastasis or induce other cellular functions. In metastasis, a subpopulation of cells of the implantation site invade and establish one or more secondary colonies in the host animal. The behavior of the implanted cell will depend on the cell type, the transfected sequence and the implantation location. Typical secondary sites for metastatic colonies include lung, kidney, liver, lymph nodes, brain, testis, spleen, bone, ovary, skin and mammary tissue. Metastatic development times vary from days to weeks even months. Cells with a high metastatic potential tend to progress to metastasis quickly while cells with a low metastatic potential may require very long periods of time that span significant portions of the lifespan of the animal.

The host animal may be analyzed for metastatic development weekly, from one week to 20 weeks to six months, nine months or one year after implantation. For animals with longer lifespans such as sheep, the animal may be inspected yearly from one year on up to ten years for metastatic tumors. Metastases can be detected by examinations such as palpation, biopsy, imaging, exploratory surgery, CAT scans, autopsy, X-ray and direct observation. In addition, tissue samples may be taken surgically from the host mammal and subjected to histological or other examination for the detection of metastases.

Expressed sequences include mRNA, rRNA, hnRNA, DNA, cDNA and any nucleic acid sequence that is expressed in the cell. These sequences may be amplified by in situ techniques or by purification of nucleic acid from collected cells. Expressed sequences may be obtained by extracting nucleic acids from cells before implantation, at the primary site or at the secondary site. Cells collected at these sites may optionally be cultured for a time before nucleic acid extraction. The effects of treatment with gene expression modifying agents or environmental conditions can be ascertained by collecting cells before and after treatment. Treatment may be applied to the cells while the cells are in the host mammal or after the cells are excised and in culture. Nucleic acid are collected from cells using techniques that are well known to those of ordinary skill in the art.

Expressed sequences may be used directly for polymerase chain reaction (PCR) analysis using, for example, the technique of reverse transcriptase polymerase chain reaction (RT-PCR). Alternatively, RNA may be enriched for mRNA using a poly-A RNA enrichment method. Numerous poly-A RNA enrichment methods exist and are commercially available. Techniques used for poly-A RNA enrichment include oligo-dT columns, oligo-dT magnetic beads, and oligo-dT cellulose. RNA may be further processed into cDNA before analysis by reverse transcription using reverse transcriptase. The cells or the extracted nucleic acid may be preserved, such as by freezing, and analyzed at a later time.

Differential display polymerase chain reactions (DD-PCR) are performed on the expressed sequences using two variable primers which may contain the same or entirely different sequences or an anchor primer and a variable primer. If an anchor primer is used, one anchor primer and one variable primer create a single or a single set of reaction products for each reaction. A complete profile may include 25 or more different PCR reactions per sample wherein each PCR reaction is performed with the same anchor primer and a different variable primer. DD-PCR may also be performed using anchor and variable primers which contain the same sequence. Whether a particular reaction is used depends on whether a difference exists between the products of two PCR reactions using the same primers. When a significant difference exists between the expression sequences amplified, one pair of PCR reactions may be sufficient and informative.

Anchor primers are preferably oligonucleotides with a poly-T sequence at the 5'-[terminas]*terminals* and a dinucleotide selected from the group consisting of AA, AG, AC, AT, GA, GG, GC, GT, CA, CG, CC and CT at the 3'-[terminas]*terminals*. For example, the sequence may be 5'-TTTTTTAA-3' or 5'-TTTTTTAG-3'. The length of the poly-T sequence is typically between about 5 to about 30 bases in length and preferably between about 10 to about 20 nucleotides long. The total length of the anchor primer can vary greatly for each experiment but is preferably between about 7 to about 32 and more preferably between about 12 and about 22. Differential diagnostic *display* polymerase chain reaction may also be performed using an anchor primer of any sequence and a length between about 5 to about 30, preferably between about 5 to about 20 and more preferably between about 7 to about 12 bases.

The variable primer may comprise a random sequence, or a specific sequence such as, for example, a sequence of SEQ ID NO. 1 to SEQ ID NO. 24. Variable primers preferably are oligonucleotides with a length between about 5 to about 30, preferably between about 5 to about 20, and more preferably between about 7 to about 12 bases in length.

To enhance detection of the PCR product, the anchor primer or the variable primer, or both, may comprise a detectable moiety. Examples of detectable moieties include radioactive moieties, phosphorescent moieties, magnetic moieties, luminescent moieties, conjugatable moieties or other detectable moiety. A plurality of detectable moieties may be used to enhance detection or to simplify data analysis. Other detectable moieties include conjugatable moieties and molecules which can bind specifically to other molecules which are themselves detectable. Examples of conjugatable moieties include avidin, streptavidin, biotin, antibody, antigen, cell adhesion molecules and other molecules with similar activities. Detectable moieties are preferably labeled nucleotides. A nucleotide may be any natural or synthetic nucleotide or nucleotide analog capable of incorporation into an elongation reaction in a polymerase chain reaction. Labeled nucleotides include nucleotide triphosphates labeled with one or more radioactive atoms such as $^{32}P$, $^{33}P$, $^{3}H$, $^{14}C$ and $^{35}S$. Products of DD-PCR reactions are compared to detect the metastatic sequence. Comparisons can be performed between expressed sequences from cells at secondary sites with cells at any stage in the method including untreated mammalian cells, transfected or treated manmmalian cells, implanted cells or cells obtained from the primary site in the host animal. DD-PCR products may be analyzed by any method which reliably compares the products of two polymerase chain reactions. Typical analytical methods used for this purpose include polyacrylamide gel electrophoresis, capillary electrophoresis and high pressure liquid chromatography (HPLC). Product produced from DD-PCR may be analyzed in double-stranded or single-stranded forms. When the products of the DD-PCR reaction are labeled the sizes and distribution of the products may be monitored and analyzed by following the labels using a radiation monitor or by autoradiography. For example, DD-PCR performed in the presence of radioactive primers or nucleotide triphosphates, can be analyzed by gel electrophoresis, by capillary electrophoresis, or by HPLC. Products are easily monitored by the presence of radioactivity.

Another method for analyzing and isolating metastatic sequences is to sequence the amplified nucleic acid sequences. Sequencing may be performed using standard methods well known to those of ordinary skill in the art. The resulting sequence may be compared to a sequence database created or well-known, such as Genbank, for identification or for locating homologs. The sequencing information may be used to calculate the physical characteristics of the nucleic acids such as melting temperature and secondary structure. The primary sequence and the physical characteristic may be used to synthesize optimal nucleic acid probes for the detection or staging of metastasis or conditions that are predictive of the presence or absence of the metastatic condition.

Another embodiment of the invention is directed to a method for identifying a metastatic sequence. A mammalian cell is pretreated with a metastatic agent to form a population of cells predisposed to metastasize. The treated cells are introduced into a host mammal at a primary site. The host animal is maintained for a period of time sufficient to develop a metastasis at a secondary site. Expressed sequences of cells at the primary site and cells at the secondary site are treated with a genotoxic agent or subjected to genotoxic conditions. Expressed sequences of the treated cells are amplified by differential display polymerase chain reaction and compared with untreated cells from any previous step to identify the metastasis sequence.

The metastatic agent may be a chemical compound, a nucleic acid or a protein that alters the metastatic potential of a cell or relates to or is associated with the metastatic process. Chemical compounds include retinoids such as 4-hydroxyphenyl (4HP). Other agents include the proteins TGF-β1, Cyclin D1, p21, p34, *mutant* p53, lysyl oxidase, caveolin, actin binding protein, ubiquitin activating enzyme E1, nmb or α-actinin 3, or their respective genes. The metastatic agent may be a metastatic stimulant or a metastatic suppressant. Metastatic stimulants may be used to enhance the sensitivity of the metastasis sequence detection method. Conversely metastatic suppressants may be used to decrease the sensitivity of the method enabling the selective identification of potent [metastatis] *metastatic* sequences or sequences specific to a particular tissue type or detastatic disorder. Treatment may comprise direct contact with the metastatic agent or incubation for a period of time. Metastatic agents enhance the metastatic potential of the implanted cells and increase the sensitivity and the speed of the overall method.

The cells at the primary site and the metastatic cells at the secondary site may be treated with a genotoxic agent in vivo or in vitro. In vivo treatment may comprise injecting genotoxic agents directly into the host mammal or specifically applying the agent with, for example, topical formulations. The cells at the primary site and the secondary site may also be isolated from the host animal and treated with the genotoxic agent in culture. Genotoxic agents are chemical compounds, nucleic acids or proteins that alter gene expression by effecting the nucleic acid genome directly by, for example, chemical modification, or indirectly by, for example, altering components associated with gene expression. Such agents include, for example, benzanthracene (BA), dimethyl benzanthracene (DMBA) and 5-azacytidine, and may include metastatic agents as well. In addition to or in place of genotoxic agents, the cells may be treated to hypoxic conditions or radiation to alter gene expression. Metastatic sequences identified in these methods may be specific for particular genotoxic agents or conditions.

Another embodiment of the invention is directed to the use of a host animal with an altered genotypic or phenotypic predisposition for metastases. A host animal may be screened for endogenous expression of metastases gene. Examples of metastatic sequences which may be screened for include sequences isolated by the method of the invention, such as, for example, the sequences listed in FIG. 12 and FIG. 13. Particularly useful metastatic sequences include TGF-.beta.. A host animal with reduced levels of a metastatic gene product may be used to isolate novel metastatic genes. Host animals may be screened for reduced levels of metastatic gene expression. In addition, transgenic technology may be use to ablate a metastatic gene in the germline of a host animal.

Another embodiment of the invention is directed to analysis of a cell line before their use as a starting material to isolate metastatic genes in a particular pathway. Analysis is useful in identifying cells, and consequently sequences specific to these cells, which are particularly susceptible or resistant to metastatic transformation. For example, a cell highly predisposed to metastasis may be especially sensitive for detecting metastatic genes. Conversely, a cell showing high resistance to metastasis can be used to isolate especially potent metastatic sequences. One method to analyze susceptibility to metastasis is to determine the cellular response to growth factors or growth inhibitors. Briefly, a control population and a test population of cells are exposed to a growth factor or a growth inhibitor and the cellular response (e.g. proliferation, metabolism) recorded. Cells showing abnormal responses to the growth factor or growth inhibitor may be used as the starting material for metastatic gene isolation. Cellular response include changes in the rate of cellular division (e.g. thymidine uptake), changes in the expression of RNA or proteins, changes in cellular localization or modification patterns of RNA or proteins, and changes in the rate of uptake, release or metabolism of nutrients.

Figure 2A:
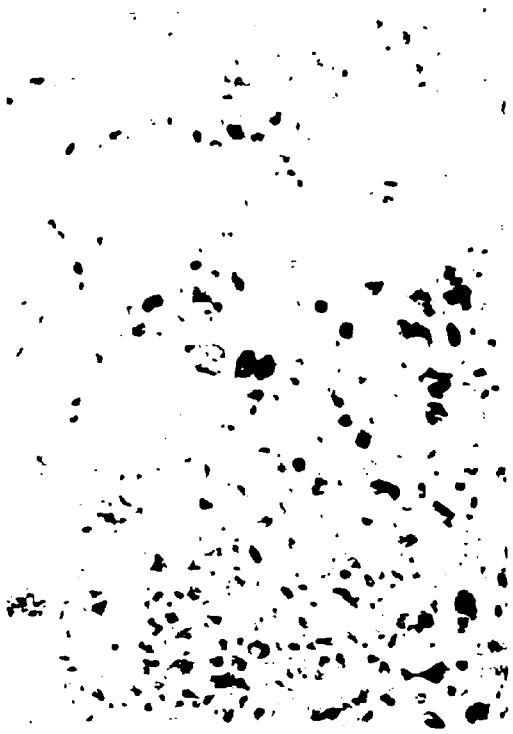
FIG. 2 A–B Staining of primary tumor (A) and metastatic deposit (B) from the lung of the same animal FIG. 3 A–D Staining of normal human prostate (A), moderately differentiated human prostate tumor (B and C), and poorly differentiated prostate tumor (D).
Figure 2B:
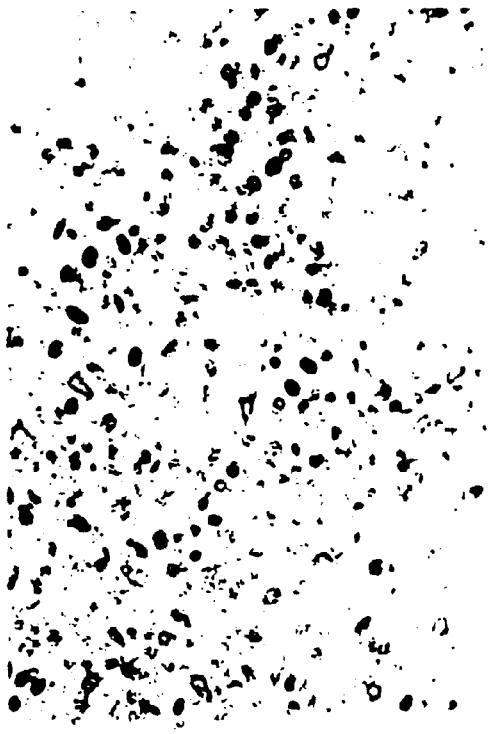
Figure 3A:
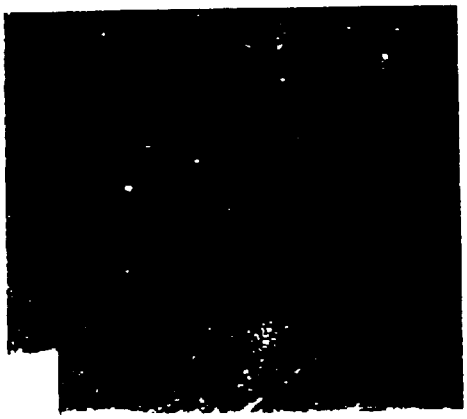
Figure 3B:
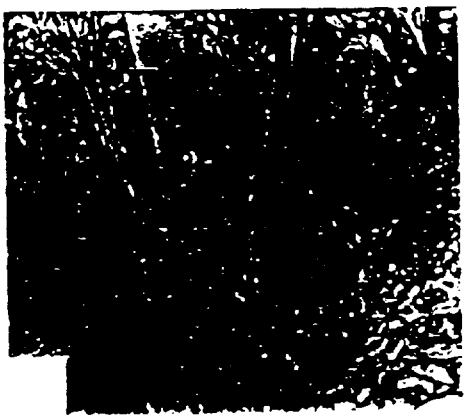
Figure 3C:
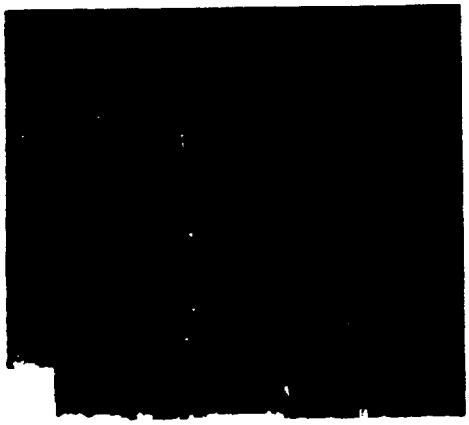
Figure 3D:
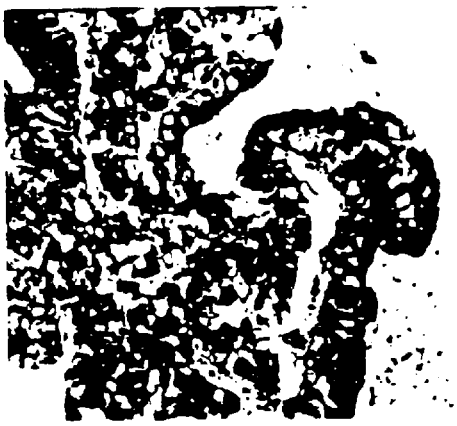

Especially potent or weak metastatic genes may be detected by treating and analyzing the metastatic potential of different cells and selecting a suitable cell type as the starting material. For example, cells may be treated with myc, ras, *mutant* p53 or combinations thereof and analyzed for cyclin D1 expression which is shown to [correlates] *correlate* with metastasis. FIG. 2 shows the in situ analysis of cyclin D1 in primary MPR tumors (FIG. 2A) and in metastatic deposits from the lung of the same animal (FIG. 2B). The gene expression pattern of cyclin D1 in MPR correlates with that of human prostate tumors (FIG. 3) analyzed with stains specific for cyclin D1 expression. Normal human tissue shows no cyclin D1 expression or staining (FIG. 3A). Moderately differentiated prostate cancers with dispersed (FIG. 3B) or focal positively staining (FIG. 3C) show moderate staining. Advanced poorly differentiated prostate cancer *cells* show strong nuclear as well as cytoplasmic staining (FIG. 3D) implying strong expression of cyclin D1. After treatment with myc, ras or *mutant* p53, cyclin D1 expression shows correlation with the metastatic potential of the cell. Thus, cyclin D1 expressing cells are a source of cells with high metastatic potential. Conversely, cells with low cyclin D1 expression are a source of potentially [metastatically] *metastasis* resistant cells.

Figure 4:
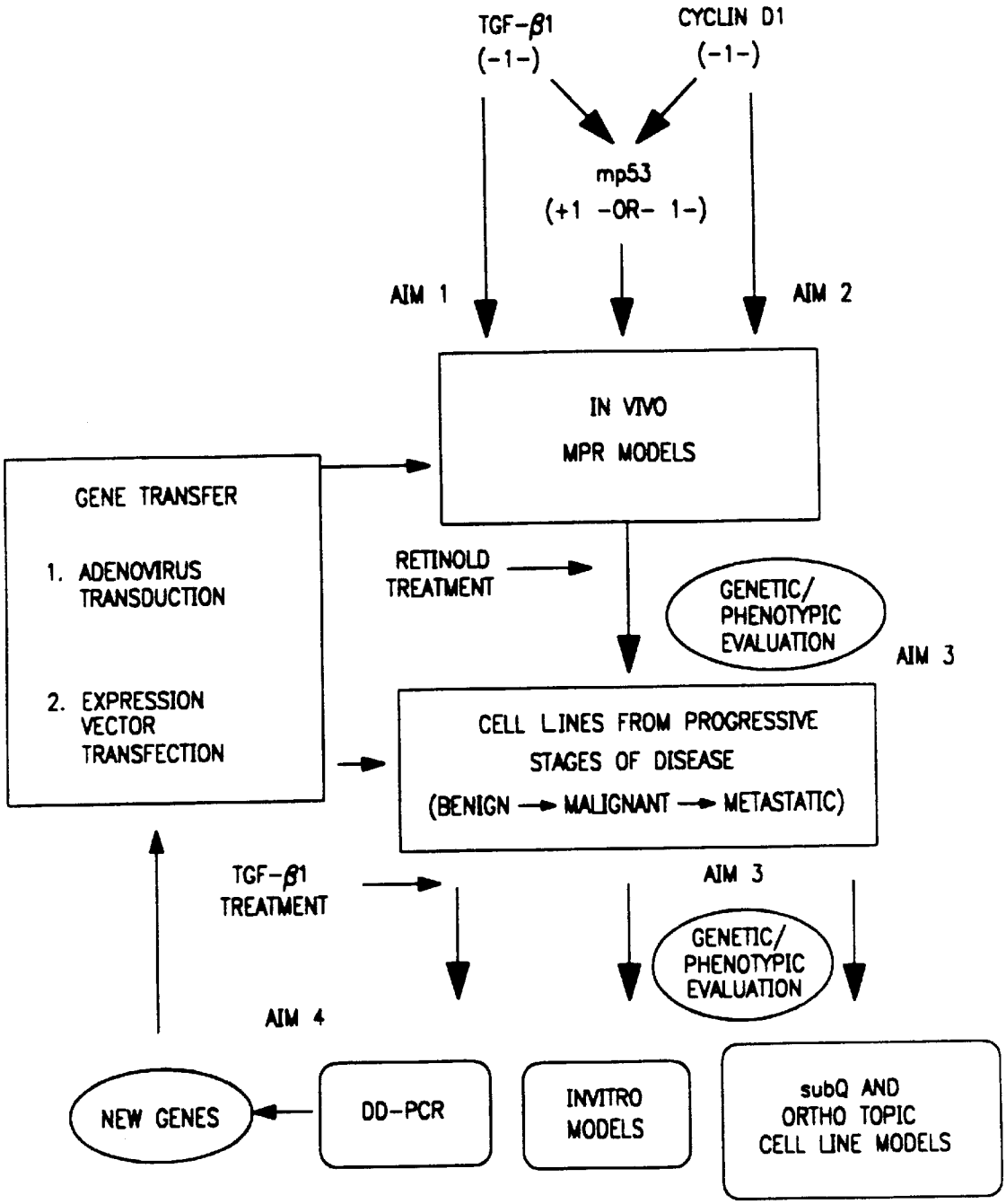
FIG. 4 Schematic of method for isolating a metastatic gene from a gene ablated mouse strain.

This method may be adjusted for the isolation of metastatic sequences expressed along a particular developmental or differentiation pathway by combining the various treatment and analytical techniques. This approach is schematically represented in FIG. 4. For example, a mammalian cell may be genetically ablated for TGF-β6, Cyclin D1, *mutant* p53, lysyl oxidase, caveolin, actin binding protein, ubiquitin activating enzyme E1, nmb, α actinin 3, or p34. The genetically altered cell is used in an in vivo mouse prostate reconstitution (MPR) model. Metastatic and nonmetastatic cells isolated from the MPR may be analyzed directly or after induction with an agent such as the TGF-β gene or its product. Analysis involves the use of differential display polymerase chain reaction to identify differentially expressed bands. Sequences identified may be used for subsequent ablation, transformation or differential analysis.

Genetic ablation (gene knockout) may be performed after a cell is selected or by selecting a cell comprising a genotype with the proper genetic ablation. Cells already comprising gene ablation may be acquired from a cell depository, from other laboratories or from a transgenic animal. As transgenic animals comprise genetically ablated genes in every cell, any tissue from a transgenic animal may be used as the starting material.

The effects of oncogenes are at least additive and often synergistic. Thus, dominant oncogenes may be transfected together or multiple recessive oncogenes ablated together for a stronger effect. Furthermore, both methods may be combined and dominant oncogene transfection may be accompanied by recessive oncogene ablation.

The function of the metastatic sequence may be determined by the differential expression pattern. For example, a [dominate] *dominant* metastatic gene will be present in a metastatic cell while a recessive metastatic gene is present in a non-metastatic cell. Metastatic sequences may be detected as bands which are present in the DD-PCR of metastases isolated in secondary sites [and] *yet* absent from DD-PCR products of primary cells. These sequences may be dominant metastatic genes whose expression is directly responsible for metastases, or they may be metastasis associated genes whose expression correlates with metastasis. Either are useful for therapy and diagnosis. Conversely, DD-PCR bands which are present in primary site tumors, but absent in secondary metastatic sites, may be dominant metastasis suppression genes. Dominant metastasis suppression genes comprise genes whose expression suppresses metastasis while nonmetastatic genes comprise genes whose expression correlates with non-metastatic tissue. Genes which are highly correlative with either the metastatic phenotype or the non-metastatic phenotype may be isolated. Isolation can be performed by cutting the appropriate nucleic acid [in the] *containing* band [of] *from* a polyacrylamide gel or by collecting the appropriate fraction in an HPLC or capillary electrophoresis. The nucleic acid may be cloned into a plasmid vector, and sequenced, or synthetically prepared.

Figure 5B:
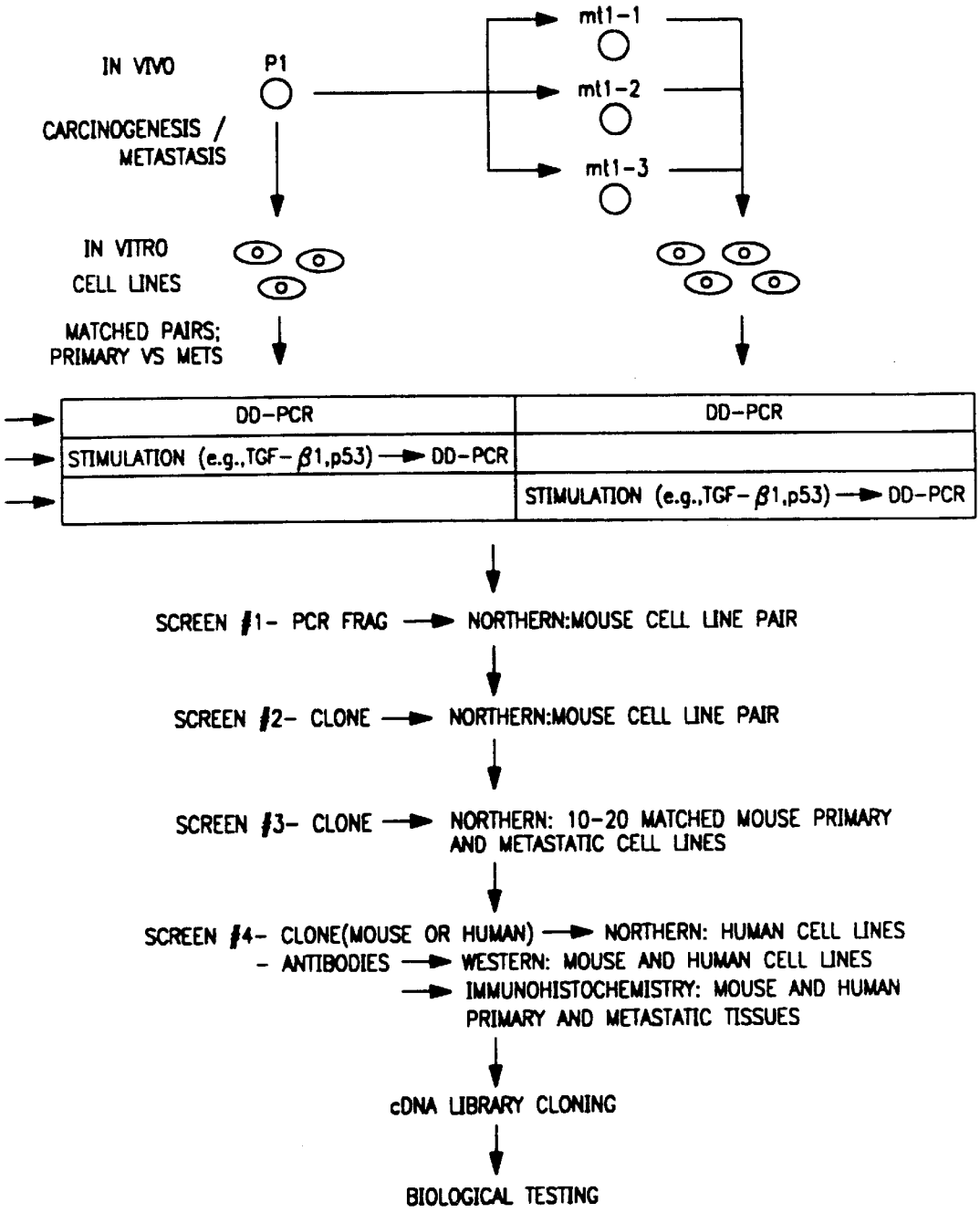

Another embodiment of the invention is directed to a method for identifying sequences in a metastatic pathway which are responsive or unresponsive to extracellular signals. Such sequences may be used in therapy and diagnosis of metastatic disorders. Implanted cells or cells from a primary site and cells from a secondary site are treated with extracellular signals. RNA sequences from the treated cells are compared with RNA sequences of the untreated cells (FIG. 5B). Treated cells and untreated cells may be derived from a short term or long term in vitro culture of primary tumors and malignant tumors. Alternatively, a part of a primary tumor and a part of a malignant tumor may be collected before the animal is treated with an extracellular cytokine or other factor. Long term cultures, or cell lines of primary and malignant cells may also be used as recipients of extracellular growth signal treatment. Suitable signals for each experiment will depend on the cell type. Generally, growth factors, lymphokines, inhibitory factors, migratory factors or hormones may be used. Factors previously isolated by commercial or methods of the invention and factors associated with or causative or suppressive of metastasis are preferred. Thus, transforming growth factor β1 (TFG-β1) may be used to treat cells before DD-PCR analysis. Proteins encoded by the genes isolated by this method are especially useful for the treatment of cells for the isolation of additional sequences. The identification of one sequence responsive to the extracellular signal pathway allows for identification of additional genes upstream and downstream from that sequence.

Another embodiment of the invention is directed to metastatic sequences identified by the methods of the invention. Metastatic sequences are sequences associated with the presence or absence of a metastasis or related to the metastatic process can be used in the therapeutic treatment of metastasis. Metastatic-related sequences include dominant metastatic sequences, recessive metastatic sequences, metastasis associated sequences, dominant oncogenes, recessive oncogenes and cell cycle genes. These genes encode for example, proteins involved in cell cycle, signal processing, DNA replication, growth regulation, inter and intra cellular signaling transcription control and translation control. Isolated sequences are useful in the treatment and for the detection of metastatic and other disorders. Disorders which may be treated comprise diseases involving proteins and sequences which are isolated by interaction with the sequences and proteins isolated by the method of the invention. Both malignant or nonmalignant disorders may be treated. Non malignant disorders include hyperplasia, dysplasia and hypertrophy. Examples of nonmalignant disorders include benign enlargement of the prostate, nodular hyperplasia, and benign prostatic hypertrophy.

Treatment may involve gene replacement, gene targeting, antisense inhibition, gene expression or gene suppression. Gene replacement involves replacing a copy of a defective gene with another copy by homologous recombination. Gene targeting involves the disruption of a cellular copy of a gene by homologous recombination. Antisense inhibition exploits the specificity of hybridization reactions between two complementary nucleic acid chains to suppress gene expression. Cloned genes can be engineered to express RNA from only one or the other DNA strands. The resultant RNA hybridizes to the sense RNA and inhibits gene expression. Gene expression and gene suppression involve the introduction of genes whose expression actively inhibits neoplastic transformation and metastasis.

Another embodiment of the invention is directed to nucleic acids which comprise a sequence identified by the methods of the invention. The nucleic acid may be DNA, RNA or PNA and may be used as a diagnostic tool in the treatment of neoplastic disorders and malignant tumors. The nucleic acids may comprise additional sequences such as promoters, for expression of a sense or antisense message, recombination sequences for gene targeting, selectable markers for transfections, or replication origins for passage in a prokaryotic or eukaryotic host such as animal cells, bacteria or yeast.

Another embodiment of the invention is directed to nucleic acids which comprise sequences identified by the method of the invention such as, for example, the caveolin *gene*, ABP280 (actin binding protein 280), the lysyl oxidase gene, and the nmb gene (clone 29), and other sequences listed in FIG. 12 and FIG. 13. Nucleic acids comprising a sequence corresponding to these genes may be used in treatment or diagnosis and in diagnostic kits for screening biological samples for the presence or absence of metastasis or metastatic potential. Treatment may involve using the sequences in gene therapy, including gene ablation, gene expression and antisense suppression. Diagnosis may involve genotypic analysis of samples to determine the existence and expression levels of the expressed sequences.

Another embodiment of the invention is directed to the use of caveolin gene and protein in the isolation of oncogenes and in the treatment of neoplastic disorders such as, for example, prostate cancer. Caveolin is an integral membrane protein and a principal component of caveolae. Caveolae are small invaginations at or near the plasma membrane of most smooth muscle cells and may function as a component of specific signal transduction pathways. Surprisingly, caveolin expression increases in metastatic human prostate cells as compared to human primary prostate tumors.

As caveolin expression correlates with metastasis, application of biological technologies designed to block the activity of caveolin or the function of caveolae may have therapeutic benefits for the treatment of neoplastic disorders such as human prostate tumors. Specific treatment approaches using caveolin may include the delivery of antisense or dominant negative caveolin sequences using expression or viral vectors; as well as the use of specific anti-caveolin antibodies. Additional approaches could also target the cavoeolae, but are not specifically based on caveolin function. Additional protein and non-protein components of caveolae could also be targeted for abrogation or the local or systemic administration of nutritional or biological agent may also be used. For example, caveolae are extremely rich in cholesterol and disruption or depletion of this molecule may alter the function of caveolae.

Another embodiment of the invention is directed to methods for treating a neoplastic disorder comprising administering a pharmaceutically effective amount of composition containing a nucleic acid having a sequence identified according to the methods of this invention, its expression product or fragments of either. The nucleic acid may be in the form of a sense or antisense single-stranded or double-stranded nucleic acid. The composition may be combined with a pharmaceutically acceptable carrier such as water, alcohols, salts, oils, fatty acids, saccharides, polysaccharides administered by injection, pulmonary absorption, topical application or delayed release. More than one carrier may be used together to create a pharmaceutical with desirable properties.

Another embodiment of the invention is directed to a kit or diagnostic [acid] *aid* for screening biological samples for detection of metastasis[,] *or* neoplasia [or kits]. *Kits* comprise sequences isolated according to the methods of the invention and reagents and materials useful in such kits, such as, for example, buffers, salts, preservatives, and carriers, all of which are well known to those of ordinary skill in the art. Kits are useful for the analysis of tissues to screen those for the determination of normal, nonmalignant neoplastic or malignant cells. Kits may comprise additional reagents useful for the extraction of nucleic acids from a tissue sample. Reagents for analyzing the nucleic acid extracted from a tissue sample such as polymerase chain reaction reagents and Southern blots reagents may also be included.

The following experiments are offered to illustrate embodiments of the invention and should not be viewed as limiting the scope of the invention.

EXAMPLES

Example 1

Production of Mouse Prostate Reconstitution Tumors and Metastasis.

Mouse Urogenital Sinus (UGS) tissue was isolated from 17 day old mice embryos. Each isolated UGS was digested with 1% trypsin for three hours at 4° C. The trypsin was inactivated by the addition of fetal calf serum. UGS cells were digested with 0.125% collagenase for 1.5 hours, counted and mixed at the appropriate cell ratios prior to infection with retrovirus in the presence of polybrene. Retroviruses used include Zipras/myc-9. Control experiments were performed using BAGA virus. After a two-hour infection, the infected cells were centrifuged and individual reconstitutions containing $1.5 \cdot 10^6$ cells produced by resuspending the cells in rat tail collagen at a density of $6.0 \cdot 10^7$ cells per ml. Aliquots of the infected UGS cells were placed in (DME) with 10% fetal calf serum overnight at 37° C., 5% $CO_2$.

The next morning each cell/collagen reconstitution was implanted under the renal capsule of an adult male +/+ animal. Reconstitutions were harvested from the mice five weeks later when they showed signs of obvious distress from the tumor burden. Metastasized tumors were isolated from the same mice at sites outside the renal capsule. Isolated tumors and metastasises were either stored in liquid nitrogen or in preservatives such as 10% buffered formalin.

Cell lines were derived from fresh tumors by mincing a small portion of the primary and metastatic tumor and placing each in explant culture in Dulbecco's Modified Eagle Medium (DMEM) supplemented with 10% fetal calf serum. Cells which grow from each explant were propagated in DMEM and 10% fetal calf serum.

For histological analysis, a portion of a fresh tumor was fixed in 10% buffered formalin and embedded in paraffin for sectioning and staining with hematoxylin and eosin (H&E) or immunohistochemical staining. Immunohistochemical localization of cytokeratins was detected using polyclonal cytokeratin antiserum A575 (Dake Co.; Carpinteria, Calif.) and Vectastain ABC kit (Vector Laboratories; Burlingame, CA).

Example 2

Isolation of C-DNA for DD-PCR.

Total cellular RNA was isolated by ultracentrifugation through cesium chloride. Briefly, up to one gram of cells from culture, tumors or organs was placed into 4 ml of ice-cold GIT buffer (4M guanidine isothiocyanate, 0.025M sodium acetate, 0.1M M β-mercaptoethanol) and homogenized in a tissue homogenizer (Polytron or equivalent). The homogenate was carefully layered over 4 ml of 5.7M CsCl, 0.024M sodium acetate (1.8 g CsC1 per ml) in a centrifuge tube. The layers were centrifuged at 35,000 RPM for 18 hours in a SW50.1 rotor. DNA was collected from the interface between the cushion and the supernatant, diluted two folds with water, added to 2.5 volumes of ethanol and spooled out on a glass rod. RNA that formed a pellet on the bottom of the CsCl layer was resuspended, and once extracted with an equal volume of phenol:chloroform (1:1), twice with chloroform and precipitated with ethanol and resuspended in diethylpyrocarbonate treated water. The concentration of DNA and RNA were be determined by absorption at 260 nanometers.

Example 3

Differential Display Polymerase Chain Reaction.

mRNA isolated from primary tumors or metastasis was reverse transcribed with one of the primers and subjected to DD-PCR using the same primer as both the forward and reverse primer. A set of 24 primers comprising short oligonucleotides were used for both the reverse transcription of mRNA into c-DNA and for differential display polymerase chain reaction. The sequence of the primers used are shown in Table 1.

TABLE 1

| Primer No. | Sequence | Sequence number |
|---|---|---|
| 1 | 5'-TGACAATCG-3' | (SEQ. ID. NO. 1) |
| 2 | 5'-ACTAAGGTC-3' | (SEQ. ID. NO. 2) |
| 3 | 5'-TCTGCGATCC-3' | (SEQ. ID. NO. 3) |
| 4 | 5'-ATACCGTTGC-3' | (SEQ. ID. NO. 4) |
| 5 | 5'-TACGAAGGTC-3' | (SEQ. ID. NO. 5) |
| 6 | 5'-TGGATTGGTC-3' | (SEQ. ID. NO. 6) |
| 7 | 5'-CTTTCTACCC-3' | (SEQ. ID. NO. 7) |
| 8 | 5'-GGAACCAATC-3' | (SEQ. ID. NO. 8) |
| 9 | 5'-TGGTAAAGGG-3' | (SEQ. ID. NO. 9) |
| 10 | 5'-TCGGTCATAG-3' | (SEQ. ID. NO. 10) |
| 11 | 5'-CTGCTTGATG-3' | (SEQ. ID. NO. 11) |
| 12 | 5'-GATCAAGTCC-3' | (SEQ. ID. NO. 12) |
| 13 | 5'-GATCCAGTAC-3' | (SEQ. ID. NO. 13) |
| 14 | 5'-GATCACGTAC-3' | (SEQ. ID. NO. 14) |
| 15 | 5'-GATCTGACAC-3' | (SEQ. ID. NO. 15) |
| 16 | 5'-TTAGCACCTC-3' | (SEQ. ID. NO. 16) |
| 17 | 5'-ACCTGCATGC-3' | (SEQ. ID. NO. 17) |
| 18 | 5'-GCTATACTGC-3' | (SEQ. ID. NO. 18) |
| 19 | 5'-AGTTGCCAGG-3' | (SEQ. ID. NO. 19) |
| 20 | 5'-AAGCCGTGTC-3' | (SEQ. ID. NO. 20) |
| 21 | 5'-TCAACGCTCA-3' | (SEQ. ID. NO. 21) |
| 22 | 5'-TGTTCGAATC-3' | (SEQ. ID. NO. 22) |

TABLE 1-continued

| Primer No. | Sequence | Sequence number |
|---|---|---|
| 23 | 5'-CGAGTCAGAC-3' | (SEQ. ID. NO. 23) |
| 24 | 5'-TATGAGTCCG-3' | (SEQ. ID. NO. 24) |

Figures 6A, 6B:
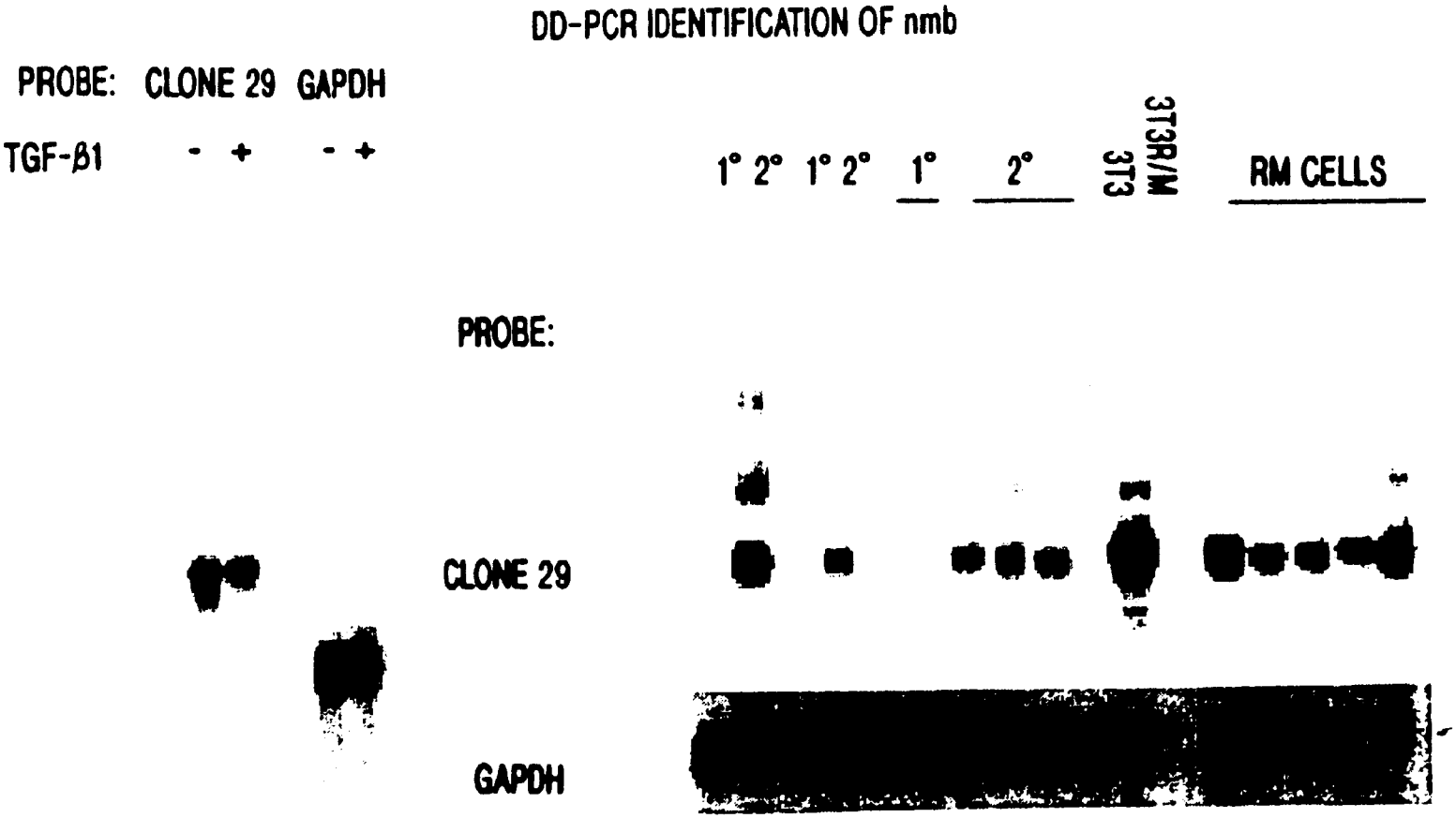
FIG. 6 Isolation and characterization of nmb gene expression by DD-PCR and RNA blot in primary and metastatic cells.
Figures 7A, 7B:
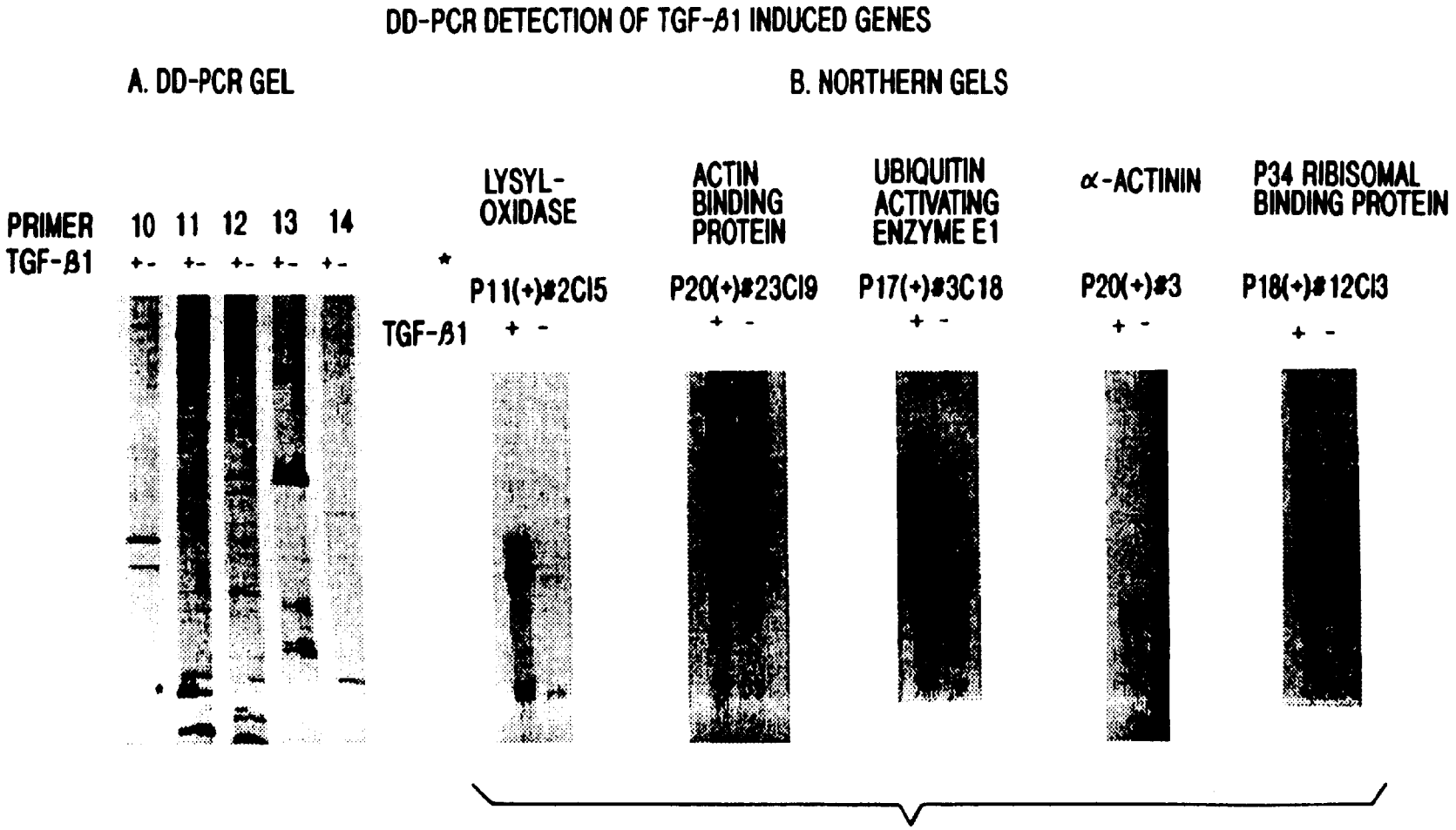
FIG. 7 Differential expression of multiple genes is determined by DD-PCR and RNA blot of primary and metastatic cells.
Figure 8:
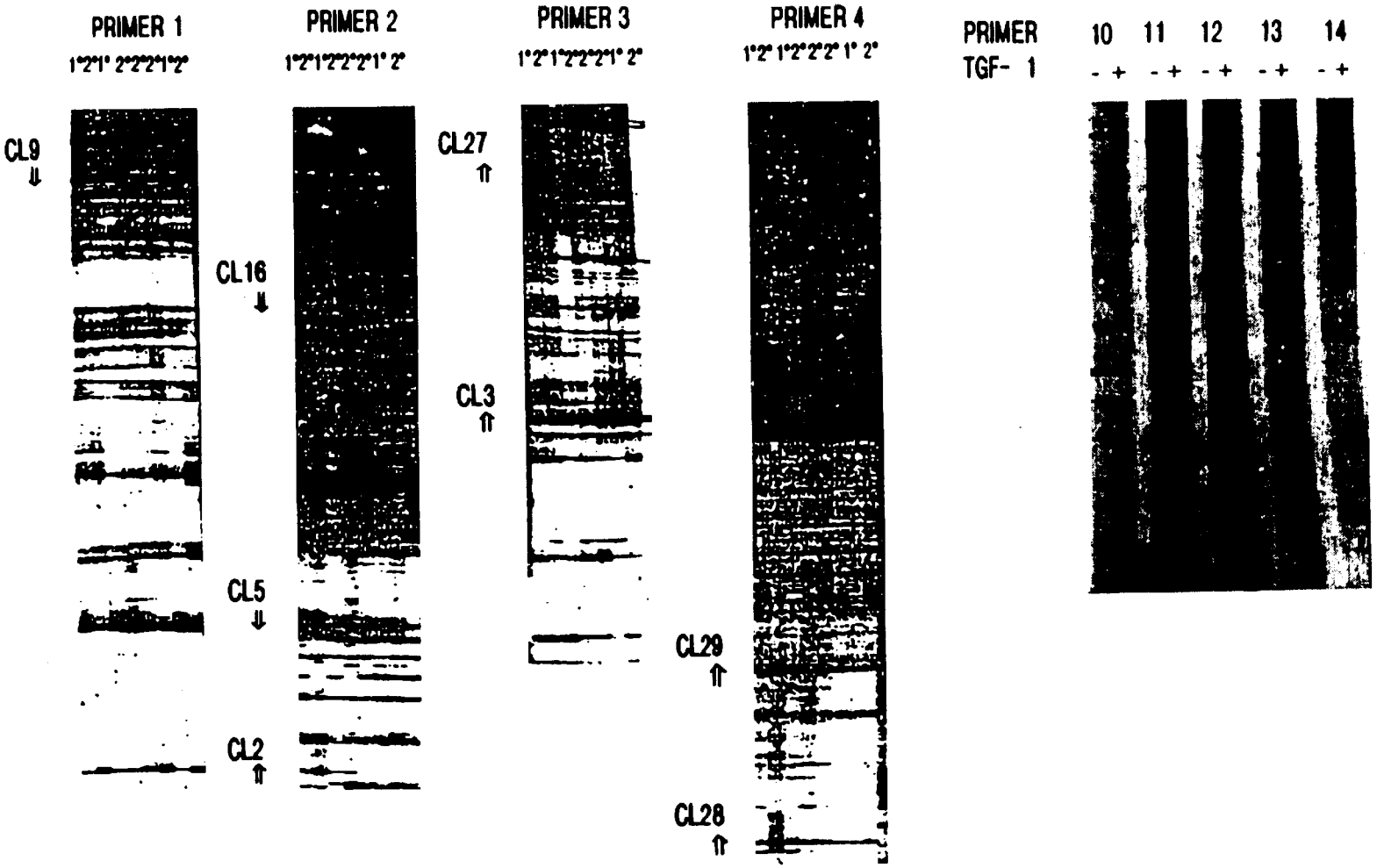
FIG. 8 Caveolin identified as a differentially expressed gene by DD-PCR.
Figure 9:
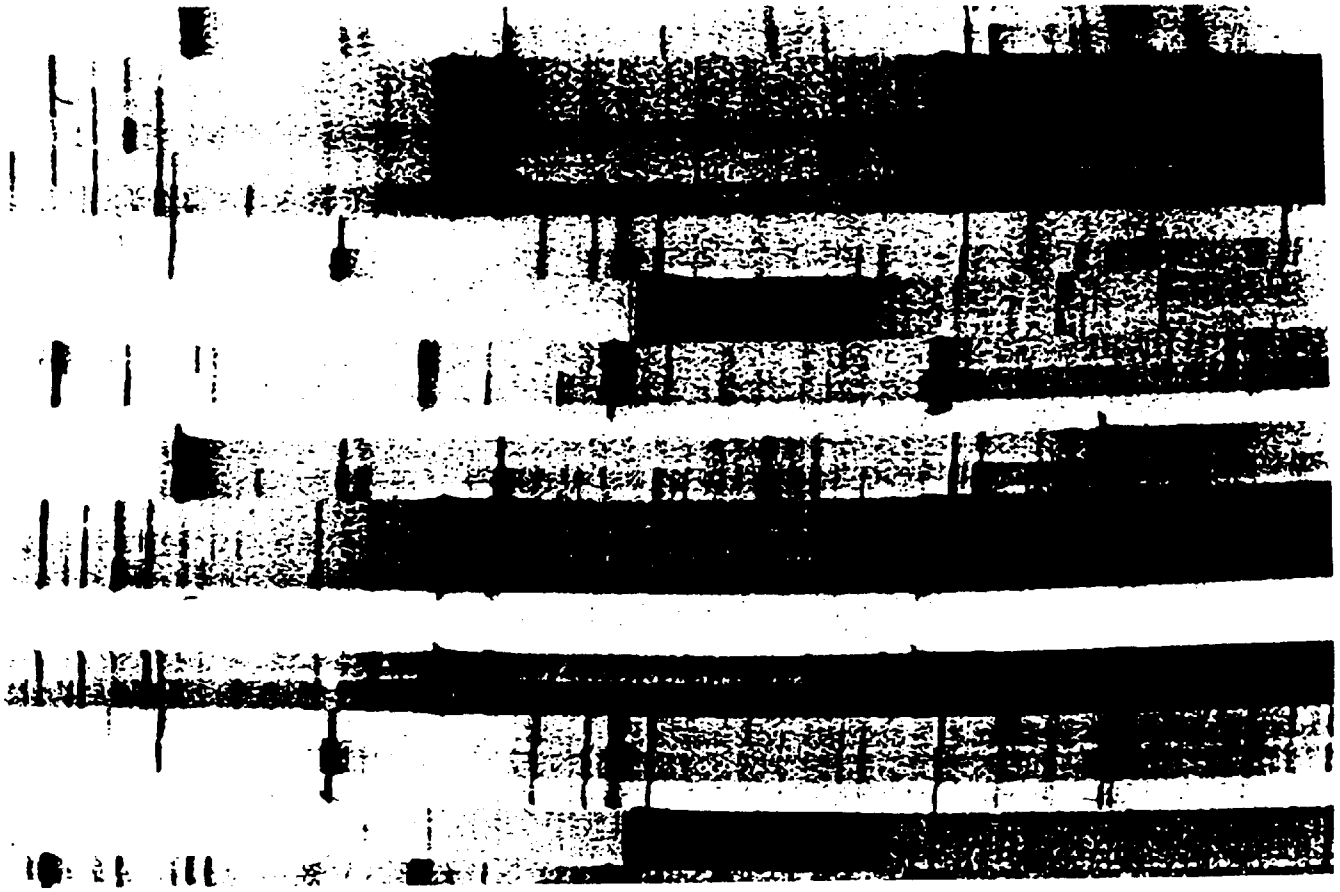
FIG. 9 Differential expression of genes isolated by DD-PCR confirmed by RNA blots.

PCR was performed using standard conditions with 40 cycles of denaturation at 94° C. for 40 seconds, annealing at 40° C. for 2 minutes, and elongation at 72° C. for 35 seconds. After PCR, the products were analyzed with non-denaturing polyacrylamide gel electrophoresis (PAGE) at 12 watts for 15 hours. Bands which differed between test and control samples were eluted from the gel, subjected to reamplification by PCR and cloned. Polyacrylamide gel electrophoresis of DD-PCRs, and the accompanying RNA blot analysis showing the isolation of sequences with substantial similarity to nmb and TGF-β is shown in FIG. 6 and FIG. 7 respectively. Additional sequences isolated by this method show substantial similarity to lysyl oxidase, actin binding protein, ubiquitin activating enzyme E1, α-actinin, and P34 ribosomal binding protein sequence (FIG. 8). Differential expression of caveolin was demonstrated by DD-PCR followed by PAGE (FIG. 9).

Example 4 p53 Allelotype Determination.

The p53 allelotype of a cell sample was determined by PCR. Briefly, nucleic acid is extracted from a tissue sample or a cell culture sample. An aliquot of nucleic acids in placed in 45 μl aliquot of a master mix which contained a final concentration of 0.2 mM of each dATP, dTTP, dGTP, dCTP, 1.5 mM $MgCl^2$, 0.5 unit Taq polymerase, 0.05 μM of each of two primers set specific for the normal wildtype allele of p53 (5'-GTGTTTCATTAGTTCCCCACCTTGAC-3', SEQ. ID NO. 25; 5'-AGAGCAAGAATAAGTCAGAAGCCG-3', SEQ. ID NO. 26). A control set of primers specific for the fibroblast growth factor-7 gene was used to monitor the polymerase chain reaction experiment (5'-ACAGACCGTGCTTCCACCTCGTC-3', SEQ. ID NO. 27; 5'-CCTCATCTCCTGGGTCCCTTTCA-3', SEQ. ID NO.28). One μl of the reaction from the first round of PCR was used as the starting material for a second round of PCR using a second set of wildtype p53 specific primer (5'-GTCCGCGCCATGGCCATATA-3', SEQ. ID NO. 29; 5'-ATGGGAGGCTGCCAGTCCTAACCC-3', SEQ. ID NO. 30). This second round of PCR was also monitored using a control set of primers specific for the fibroblast growth factor-7 (5'-ACAGACCGTGCTTCCACCTCGTC-3', SEQ. ID NO 27; 5'-CCTCATCTCCTGGGTCCCTTTCA-3', SEQ. ID NO 28).

After PCR the products were analyzed with non-denaturing polyacrylamide gel electrophoresis (PAGE) at 12 watts for 15 hours. Bands which differed between test and control were eluted from the gel, subjected to reamplification by PCR and cloned.

Example 5

Induction of cell lines with TGFβ6 Influence Cellular Gene Expression.

1481-PA cells were grown overnight in DME supplemented with 10% fetal calf serum overnight at 37° C., and 5% $CO_2$. Induction was performed by treatment with TGF-β1 at a concentration of 2 nanograms per ml. The treated cells were returned to the incubator and cultured for 12 hours. After induction, cells were washed in phosphate buffered saline and harvested and concentrated by centrifugation.

Figure 10:
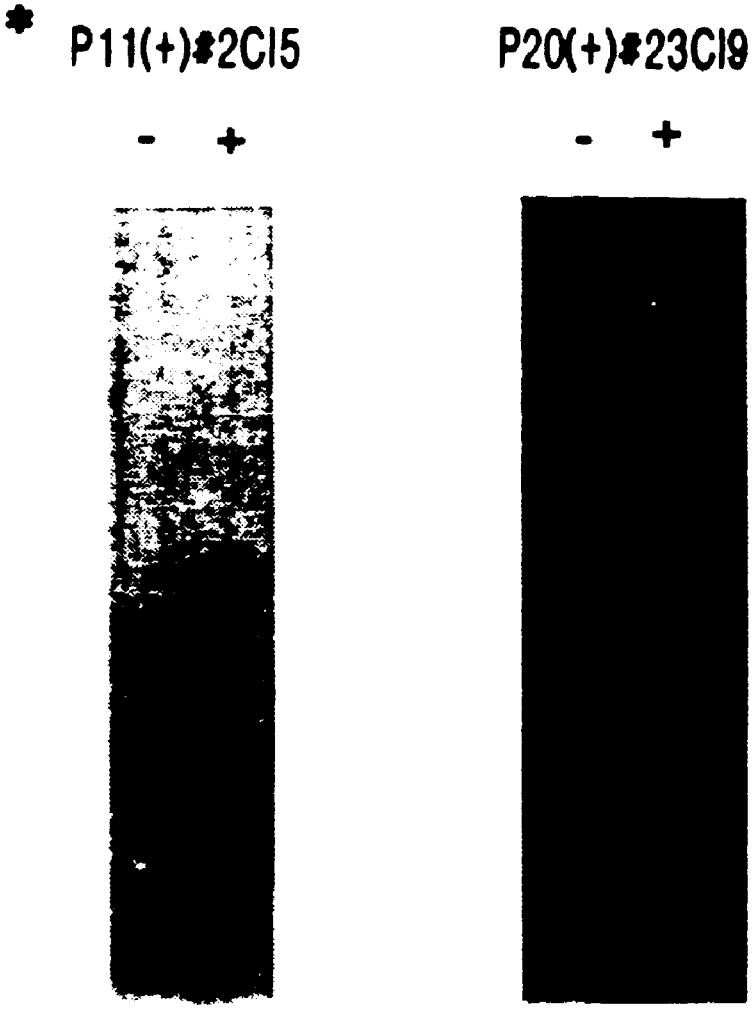
FIG. 10 RNA blot analysis of total tumor mRNA using clone 29 GADPH probes.

RNA was extracted from treated and untreated cells and subjected to DD-PCR. Differentially expressed bands detected by DD-PCR were cloned and differential expressions were confirmed using RNA blots (FIG. 10). Subsequent cloning and sequencing identified the bands as ABP280 or filamin.

Figure 11:
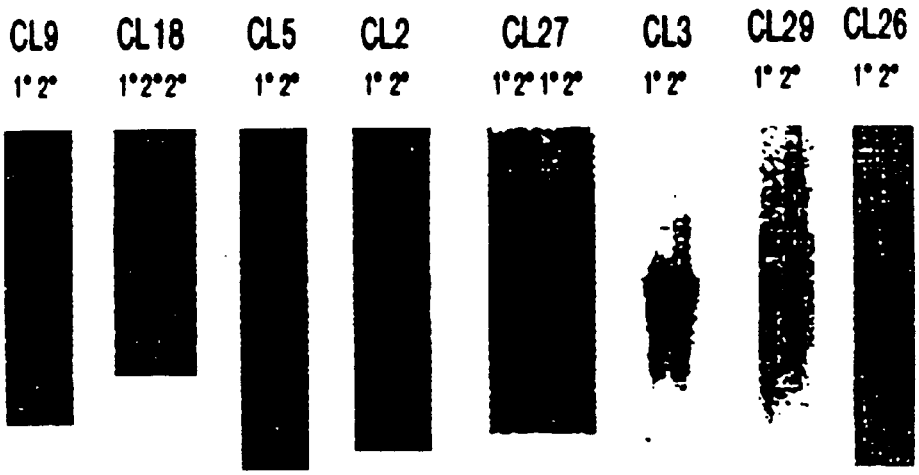
FIG. 11 RNA blot of three independent MPR metastatic tumors and 5 MPR non-metastatic tumors.

One gene isolated showed differential expression in cells induced by TGF-β (FIG. 11, clone 29), while a control probe on the same cell line showed no difference in expression levels (FIG. 11, GAPDH).

Example 6

Metastatic Sequences Isolated.

Using the methods of Examples 1, 2, 3, 4, and 5, a plurality of metastatic sequences were isolated and sequenced. The expression of the metastatic sequences in primary cells and in metastatic cells were determined using RNA blots. The nucleic acid sequences of other isolated sequences are listed in FIG. 12. Sequence analysis and expression analysis was performed on the isolated cloned and the results of these studies are summarized in FIG. 13.

Example 7

Caveolin Immunoassay in Human Prostate Cancers.

Primary site human prostate tumors and metastases were isolated and analyzed for caveolin expression by immunoassay. The results of the assay is shown in Table 3. Metastases shows higher levels of caveolin proteins in metastases than in primary tumors. Immunohistology of tissue sections reveals both elevated levels and distinct distribution of caveolin protein in metastatic human prostate when compared to a primary human prostate tumor (FIG. 14).

TABLE 3

| Patients | Primary-site | Metastases in lymph node |
|---|---|---|
| 1 | + | ++ |
| 2 | ++ | +++ |
| 3 | ++ | +++ |
| 4 | ++ | ++ |
| 5 | + | + |
| 6 | ++ | ++ |
| 7 | ++ | +++ |
| 8 | + | + |
| 9 | – | – |
| 10 | + | + |
| 11 | + | + |
| 12 | ++ | ++ |
| 13 | + | + |
| 14 | ++ | +++ |

Other embodiments and uses of the invention will be apparent to those skilled in the art from consideration of the specification and practice of the invention disclosed herein. The specification and examples should be considered exemplary only with the true scope and spirit of the invention indicated by the following claims.

SEQUENCE LISTING (1) GENERAL INFORMATION:

(iii) NUMBER OF SEQUENCES: 175

(2) INFORMATION FOR SEQ ID NO: 1:

(i) SEQUENCE CHARACTERISTICS:
(A) LENGTH: 9 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 1:

TGACAATCG 9

(2) INFORMATION FOR SEQ ID NO: 2:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO -continued (iv) ANTI-SENSE: NO (v) FRAGMENT TYPE: <Unknown>

(vi) ORIGINAL SOURCE:

(xi) SEQUENCE DESCRIPTION: SEQ ID NO: 2:

AGCTAAGGTC 10

(2) INFORMATION FOR SEQ ID NO: 3:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 3:

TCTGCGATCC 10

(2) INFORMATION FOR SEQ ID NO: 4:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 4:

ATACCGTTGC 10

(2) INFORMATION FOR SEQ ID NO: 5:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 5:

TACGAAGGTG 10

-continued (2) INFORMATION FOR SEQ ID NO: 6:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 6:

TGGATTGGTC 10

(2) INFORMATION FOR SEQ ID NO: 7:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 7:

CTTTCTACCC 10

(2) INFORMATION FOR SEQ ID NO: 8:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 8:

GGAACCAATC 10

(2) INFORMATION FOR SEQ ID NO: 9:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA -continued (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 9:

TGGTAAAGGG 10

(2) INFORMATION FOR SEQ ID NO: 10:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 10:

TCGGTCATAG 10

(2) INFORMATION FOR SEQ ID NO: 11:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 11:

CTGCTTGATG 10

(2) INFORMATION FOR SEQ ID NO: 12:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 12:

-continued

GATCAAGTCC 10

(2) INFORMATION FOR SEQ ID NO: 13:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 13:

GATCCAGTAC 10

(2) INFORMATION FOR SEQ ID NO: 14:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 14:

GATCACGTAC 10

(2) INFORMATION FOR SEQ ID NO: 15:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 15:

GATCTGACAC 10

(2) INFORMATION FOR SEQ ID NO: 16:

(i) SEQUENCE CHARACTERISTICS:
(A) LENGTH: 10 base pairs
(B) TYPE: nucleic acid
(C) STRANDEDNESS: single -continued (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 16:

TTAGCACCTC 10

(2) INFORMATION FOR SEQ ID NO: 17:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 17:

ACCTGCATGC 10

(2) INFORMATION FOR SEQ ID NO: 18:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 18:

GCTATACTGC 10

(2) INFORMATION FOR SEQ ID NO: 19:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

-continued (vi) ORIGINAL SOURCE:

(xi) SEQUENCE DESCRIPTION: SEQ ID NO: 19:

AGTTGCCAGG 10

(2) INFORMATION FOR SEQ ID NO: 20:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 20:

AAGCCGTGTC 10

(2) INFORMATION FOR SEQ ID NO: 21:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 21:

TCAACGCTCA 10

(2) INFORMATION FOR SEQ ID NO: 22:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 22:

TGTTCGAATC 10

(2) INFORMATION FOR SEQ ID NO: 23:

(i) SEQUENCE CHARACTERISTICS:

-continued (A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 23:

CGAGTCAGAC 10

(2) INFORMATION FOR SEQ ID NO: 24:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 24:

TATGAGTCCG 10

(2) INFORMATION FOR SEQ ID NO: 25:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 25:

GTGTTTCATT AGTTCCCCAC CTTGAC 26

(2) INFORMATION FOR SEQ ID NO: 26:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO -continued (v) FRAGMENT TYPE: <Unknown>

(vi) ORIGINAL SOURCE:

(xi) SEQUENCE DESCRIPTION: SEQ ID NO: 26:

AGAGCAAGAA TAAGTCAGAA GCCG 24

(2) INFORMATION FOR SEQ ID NO: 27:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 27:

ACAGACCGTG CTTCCACCTC GTC 23

(2) INFORMATION FOR SEQ ID NO: 28:

(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 28:

CCTCATCTCC TGGGTCCCTT TCA 23

(2) INFORMATION FOR SEQ ID NO: 29:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 29:

GTCCGCGCCA TGGCCATATA 20

-continued (2) INFORMATION FOR SEQ ID NO: 30:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 30:

ATGGGAGGCT GCCAGTCCTA ACCC 24

(2) INFORMATION FOR SEQ ID NO: 31:

(i) SEQUENCE CHARACTERISTICS:
(A) LENGTH: 234 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 31:

AATTTTTTTT TTCGACGGCC CAACGGAATT TTTTTTTTCG ACGGCCCAAC GGAATTTTTT 60

TTTTCGACGG CCCAACGGGA ATTCGGCTTA GCTAAGGTCA CCCAGACTTC ATGGACTTGT 120

CTATTTTCTT GCCCAAAGGG ATAGTTCCTC AGGTATTTGG GGACAGCATT CACCTCTTGC 180

AGGAGCTATG CCTGTGTGTT TGTGCTAAGT TGATACTTTC TGCGATGATC TCAC 234

(2) INFORMATION FOR SEQ ID NO: 32:

(i) SEQUENCE CHARACTERISTICS:
(A) LENGTH: 266 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 32:

TACCATCGGA GAAAGAAGAC CAAGCAAGGC TCAGGCAGCC ACCGCCTGCT TCGCACTGAG 60

CCTCCTGACT CAGACTCAGA GTCCAGCACA GACGAAGAGG AATTTGGAGA ATTGGAAATC 120

GCTCTCGTTT TGTCAAGGGA GACTATCCCG ATGCTGCAAG ATCTGCTGTC CCTCTGGCCT 180

TTGTCATCCT CGCGCCTGCG TTGTGGCCTC TGTGGGCTTG GTGTGGAGCA AATGGCTCTC 240

-continued

AAGGAGGACT GAGTCTCAAG GAAATT 266

(2) INFORMATION FOR SEQ ID NO: 33:

(i) SEQUENCE CHARACTERISTICS:
(A) LENGTH: 300 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 33:

AGCTAAGGTC AGGAGGTGTC TGAAGAATTG GCTGATGCAT GGCAGGGATG TTGTTGACCT 60

GCTTTTAGAA CAATACTTCC ATTTAATTAT AGCATATCTT ATGTGTGTAT TAAAGCAGAG 120

CCGATCTGGT GGGGCTCATT AAGTAAATGT ACTTACTGCA AAAGGTTCAA CTGGTGACCC 180

CAGTTTTCCC CAGAAGCAAT ATGATAGGAC AGAGGCGACT CCTGCAAGTT GTCTCAGACT 240

TCACACATAC ATTGTGACAT TCTCTGAGCA TGTGCACTGT ACATGATATG ACACTATCAA 300

(2) INFORMATION FOR SEQ ID NO: 34:

(i) SEQUENCE CHARACTERISTICS:
(A) LENGTH: 312 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 34:

AGCTAAGGTC CACTACCTTG TGAAGATGTA TAAACACCTG AAATGTAGAA GCGATCCGTA 60

TGTCAAGATC GAGGGGAAGG ACGCTGACGA CTGGCTGTGT GTGGACTTTG GGAGTATGGT 120

GATCCATTTG ATGCTTCCAG AAACCAGAGA AACCTATGAA TTAGAGAAAC TATGGACTCT 180

ACGTTCTTTT GATGACCTTA GCTAAGCCGA ATCAGCACAC TGGCGGCGTT ACTAGTGGAT 240

CGAGCTCGTA CAGCTGATGC ATAGCTTGAG TATCTATAGG TTACTAATAG CTGGCTATCA 300

TGTCAAGCGT TC 312

(2) INFORMATION FOR SEQ ID NO: 35:

(i) SEQUENCE CHARACTERISTICS:
(A) LENGTH: 281 base pairs
(B) TYPE: nucleic acid
(C) STRANDEDNESS: single
(D) TOPOLOGY: linear (ii) MOLECULE TYPE: cDNA (iii) HYPOTHETICAL: NO -continued (iv) ANTI-SENSE: NO (v) FRAGMENT TYPE: <Unknown>

(vi) ORIGINAL SOURCE:

(xi) SEQUENCE DESCRIPTION: SEQ ID NO: 35:

AGCTAAGGTC AAAATAAAAG CTCAAGATGA CATCAGTCCC ATTTGTCCTA AGTCCTGGTG 60

TTGTATGGAT GGTAAGCAGC AGCCAATTAT GGTGACAGGT GATAGATCCA ATTTGTTAAC 120

ATTTCTCCAT CTCTAAGCCA TCCTTAAAGA AAATCATGAA TGGAGTCACA CCATCTTCAC 180

GGTAGTCCAG GAGAGCAACC ATACCATCTG GATTCATGTT TCACCAATAA AAACTGGTAG 240

TTATTGAATT AGCAAGGATG TGCTACTCTC TGCAGCTCAG C 281

(2) INFORMATION FOR SEQ ID NO: 36:

(i) SEQUENCE CHARACTERISTICS:
(A) LENGTH: 240 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 36:

AGCTAAGGTC TCATGCAATG GAACTTAATT CTTAGAACTG TAAGAATTAC ATCAAACATA 60

AAAGCCTCCC TATTAATGTA GTCCACAAAA CTGGCAGGTA TATATGCCTT CTGAATTTGT 120

CTCCAGTGAC TTTGGTAAAT CTAACTAAAT TTTTAAAAAT TCTTAATGAA TTTATCGTCA 180

ACAACAACCA CCTCTTGGAA AATTAACCCT TGCAGTGTCT GTGTTAGACT CAGAAGTCAA 240

(2) INFORMATION FOR SEQ ID NO: 37:

(i) SEQUENCE CHARACTERISTICS:
(A) LENGTH: 203 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 37:

GAATTCGGCT TAGCTAAGGT CAGCGTGAAG TTTAAGCAGA CATGAGTCTG AAACAGTCTC 60

ATGACACATC TGATAGGATT TTTTAAGACT GCCTGGCTTA GTCTTACTGC TGTTAGTGTA 120

TATTAGGTGT TGTACACATT ATAAAGAAAA TTATGTCTCA TTATCTTGTT TAAGTCAAGG 180

AAAATAGAGA ACTTTGGTCA AAT 203

(2) INFORMATION FOR SEQ ID NO: 38:

-continued (i) SEQUENCE CHARACTERISTICS:
(A) LENGTH: 194 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 38:

GAATTCGGCT TAGCTAAGGT CAGCGTGAAG TTTAAGCAGA CATGAGTCTG AAACAGTCTC 60

ATGACACATC TGATAGGATT TTTTAAGACT GCCTGGCTTA GTCTTACTGC TGTTAGTGTA 120

TATTAGGTGT TGTACACATT ATAAAGAAAA TTATGTCTCA TTATCTTGTT TAAGTCAAGG 180

AAAATAGAGA ACTT 194

(2) INFORMATION FOR SEQ ID NO: 39:

(i) SEQUENCE CHARACTERISTICS:
(A) LENGTH: 230 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 39:

GAATTCGGCT TAGCTAAGGT CAAAATACAC GGATTGCAAT CACTTTTCTA AACAAAAGAA 60

ACAAAGTAAC TGCTGAGGTT AGCAAAGATG AGTTCTCGTC ATACTGCCTT GTACTGTTTT 120

GTGAACTGTG TTATTAAAAA TCTGAGCTTA ACAAAATCTT TACAAGTCAC CTCATGAAAA 180

CAGCATTTGG CCAATAAGAG TTTAATTCCA CACCAGTGAG ACCTTAGCCT 230

(2) INFORMATION FOR SEQ ID NO: 40:

(i) SEQUENCE CHARACTERISTICS:
(A) LENGTH: 242 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 40:

GAATTCGGCT TTCTGCGATC CACTCTTTGA AGCTATTGGC AAGATATTCA GCAACATCCG 60

-continued

```
CATCAGCACG CAGAAAGAGA TATGAGGGAC ATTTCAAGGA TGAAAGGTTT TTTTCCCCCC    120

TTACTATTTC CTTGGTGCCA ATTCCAAGTT GCTCTCGCAG CAGCAAATTT ATGAATGGTT    180

TGTCTTGATC AAGAACAAAG AATTCATTCC CACCATTCTC ATATATACTA CTTTCTCTTC    240

TT                                                                   242
```

(2) INFORMATION FOR SEQ ID NO: 41:

(i) SEQUENCE CHARACTERISTICS:
(A) LENGTH: 240 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 41:

```
GAATTCGGCT TTCTGCGATC CACTCTTTGA AGCTATTGGC AAGATATTCA GCAACATCCG     60

CATCAGCACG CAGAAAGAGA TATGAGGGAC ATTTCAAGGA TGAAAGGTTT TTTTCCCCCC    120

TTACTATTTC CTTGGTGCCA ATTCCAAGTT GCTCTCGCAG CAGCAAATTT ATGAATGGTT    180

TGTCTTGATC AAGAACAAAG AATTCATTCC ACCATTCTCA TATATCTACG TCTCTTCTAG    240
```

(2) INFORMATION FOR SEQ ID NO: 42:

(i) SEQUENCE CHARACTERISTICS:
(A) LENGTH: 154 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 42:

```
GAATTCGGCT TTCTGCGATC CTAGAGCAGG TAAGTGAAGA AGGCCAGTAA GTTTTAAGGA     60

TGGCCTTGTT GCCTTCTATC AAGTTCTCTG GGACTTTGTA ATTTTGATTA CTACTATTGA    120

TACATGGTTA TGGTCAGAAG GCCTCTTCTC CCTT                                154
```

(2) INFORMATION FOR SEQ ID NO: 43:

(i) SEQUENCE CHARACTERISTICS:
(A) LENGTH: 270 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO -continued (v) FRAGMENT TYPE: <Unknown>

(vi) ORIGINAL SOURCE:

(xi) SEQUENCE DESCRIPTION: SEQ ID NO: 43:

AGCTAAGGTC CGGACTCTAT GGCATGACCC CAAAAACATT GGCTGGAAAG ATTACACTGC 60

CTACAGGTGG CACCTGATTC ACAGGCCTAA GACAGGCTAC ATGAGAGTCT TAGTGCATGA 120

AGGAAAGCAA GTCATGGCTG ACTCAGGACC AATTTATGAC CAAACCTACG CTGGTGGACG 180

GCTGGGCTGT TTGTCTTCTC CAAGAGATGG TCTATTCTCG GACCTCAAGT ATGAGTGCAG 240

AGATGCTAGA GAGCAGGCTC AGTCTCAGCA 270

(2) INFORMATION FOR SEQ ID NO: 44:

(i) SEQUENCE CHARACTERISTICS:
(A) LENGTH: 285 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 44:

TGACCATCGA GTGCATCAGC CTCATCGGGC TGGCCGTCGG GAAGGAGAAA TTCATGCAGG 60

ATGCTTCAGA TGTGATGCAG CTATTGTTGA AGACACAGAC AGACTTCAAT GATATGGAAG 120

ATGACGACCC CCAGATTTCT TACATGATCT CAGCATGGGC CAGGATGTGC AAAATCTTGG 180

GAAAGAATTC CAGCAGTACC TTCCCGTGGT TATGGGGCCG CTGATGAAGA CTGCTTCAAT 240

TAAGTCCTGA GTGCCTCTAG ACACCAGGAC ATGAGATATG AGGTA 285

(2) INFORMATION FOR SEQ ID NO: 45:

(i) SEQUENCE CHARACTERISTICS:
(A) LENGTH: 260 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 45:

TGACCATCGT GTAGTTGGTG TGCTTGTTGT CGAAGATGAG GGCCTCCTGG ATGAGCTGGT 60

GCTGCTGCTC CAGCAGGTCC AGGCTGGGCT TGTAGTCCAC GATGCTGCGC TCGTACTGCT 120

TCAGGTGGCT CAGCTGGTCT TCCAGAGTCC CGTTCATCTC AATGGAGATG CGCCCGATCT 180

CCTCCATCTT AGTCTGGATC CACGGCCCCA CCATATTGGC TTGGCTGGCG AACTGTCGGC 240

GAAGGCTGCA TTGGATTGCT 260

-continued (2) INFORMATION FOR SEQ ID NO: 46:

(i) SEQUENCE CHARACTERISTICS:
(A) LENGTH: 283 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 46:

TGACCATCGA ACACCCCAAC ACTCTCCACT ACCTGCCATT TCTTCCAGCC TTATCCACAC 60

CACCCCGTTT CTCCTGAAGA CTGATTTGCT TAGCAACTGC ACTGAGCCAA CCCTGAAGAC 120

ACATGATTAT TGGTTGGGCT CCATTAAACA ACAAGCCTAG TGCTTGGGAA GGGGGGTGGG 180

GAGGGGAAGA GACGTGAGAA GCATGTTGGC GTAGACCTTG AGGCATGGAT GAAGCATCTG 240

CCGGCCTGAC CTGGTACAGG TGGCATCTGC ACTGCAGCAA GGC 283

(2) INFORMATION FOR SEQ ID NO: 47:

(i) SEQUENCE CHARACTERISTICS:
(A) LENGTH: 277 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 47:

TGACCATCGA AGTGCAAAGG AAATGACTTG ATTTCATGAA GTATCTCCAG AAGTAACGCT 60

TTGTTTTCTG CATCCTGAAC TTTATTCCCA GTGAAGAGCT GAAAATCTGG ACGCTCAAAA 120

AATGGAAGCA CTTTGGAGAG AGCCCTTAAC TCTATCAGGT ACAGGAAGTA CAAGTTCCTC 180

AGCCTTCGTG GGCCTTCTCC TTCAGTCAGA ATCCATCAAA GGTGCTGGAA CTCTGTGACA 240

TTGTGACCCA TTCTTTCAGC CAGTATCTGT AAGATAC 277

(2) INFORMATION FOR SEQ ID NO: 48:

(i) SEQUENCE CHARACTERISTICS:
(A) LENGTH: 215 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

-continued (xi) SEQUENCE DESCRIPTION: SEQ ID NO: 48:

GGGAACGAAT GATCTGGAAC TGTGGCTTGT AGACAACCCA AATATCTTAG GTAGGTAAGA 60

AATTCCAGCA TCACACTATA TAGGAAATAC TGTGCGAAAC TGACAGTTAA CTGTGCACAA 120

AGTTCAATGG CTTCAAAATA ATGTATAAAG GATAAGAAGA AACCAGTTTA CCATTTTGGT 180

ATTATTTTGG TTGCTTTGTA TAACTTCAAT AATTT 215

(2) INFORMATION FOR SEQ ID NO: 49:

(i) SEQUENCE CHARACTERISTICS:
(A) LENGTH: 215 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 49:

GGGAACGAAT GATCTGGAAC TGTGGCTTGT AGACAACCCA AATATCTTAG GTAGGTAAGA 60

AATTCCAGCA TCACACTATA TAGGAAATAC TGTGCGAAAC TGACAGTTAA CTGTGCACAA 120

AGTTCAATGG CTTCAAAATA ATGTATAAAG GATAAGAAGA AACCAGTTTA CCATTTTGGT 180

ATTATTTTGG TTGCTTTGTA TAACTTCAAT AATTT 215

(2) INFORMATION FOR SEQ ID NO: 50:

(i) SEQUENCE CHARACTERISTICS:
(A) LENGTH: 10 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 50:

GACGTAAGCC 10

(2) INFORMATION FOR SEQ ID NO: 51:

(i) SEQUENCE CHARACTERISTICS:
(A) LENGTH: 189 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 51:

CCACAAAGCA AGCTTCTGTC TGGAGTACAG CTCCTGTGAC TATGGGTACC ACAGGGCCTT 60

TGCGTGCACT GCACACACAC AGGGATTGAG TCCTGGATGT TATGACACCT ATGCGGCAGA 120

CATAGACTGC CAGTGGATTG ATATTACAGA TGTACAACCT GGAAACTACA TTCTAAAGGT 180

CAGTGTAAA 189

(2) INFORMATION FOR SEQ ID NO: 52:

(i) SEQUENCE CHARACTERISTICS:
(A) LENGTH: 227 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 52:

CTATCAATGA AGGGGGAGAT CACTGGGTAA GTTCGAATGC CCTCAGGCAA GGTGGCCCAG 60

CCTTCCATTA CTGAATTCAA AGATGGCACT GTTACTGTAC GTTACTCACC CAGTGAAGCT 120

GGCCTGCATG AAATGGACAT TCGCTATGAC AATATGCATA TCCCAGGAAG CCCTCTGCAG 180

TTCTATGTTG ATTATGTCAA CTGTGGCCAC ATCACTGCTT ATGGTCC 227

(2) INFORMATION FOR SEQ ID NO: 53:

(i) SEQUENCE CHARACTERISTICS:
(A) LENGTH: 373 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 53:

TTAGCACCTC GACCACGAAA TGAGGAAGAT GCAACAGACG TGGTGGGCCT GGCTCAGGCT 60

GTAAACGCTC GGTCCCCACC TTCAGTAAAA CAGAACAGCT TGGATGAAGA CCTTATTCGG 120

AAGCTAGCTT ATGTTGCTGC TGGGGACCTG GCACCCATAA ATGCTTTCAT TGGGGGCCTT 180

GCTGCCCAGG AAGTCATGAA GGCCTGCTCT GGAAAGTTTA TGCCCATCAT GCAGTGGTTG 240

TACTTTGATG CTCTTGAATG TCTCCCAGAA CGGACAAAGA GGCTCTGACA GAGGAGAGTG 300

CCTCCCACGT CAGAACCGTT ACGATGGGCA GGTAGCTGTA TTGGTCAGAC TTCAGGAGAA 360

GCTGAGAAGC AAA 373

(2) INFORMATION FOR SEQ ID NO: 54:

-continued (i) SEQUENCE CHARACTERISTICS:
(A) LENGTH: 257 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 54:

```
TTAGCACCTC CAATGGCTGG GTACCAGCCA GCCGCAATGT CCGCTCCACA AATTTGGAGT     60

CTGTGAGGTA CTGATTAACA TTTTCTGCTG GCTGCTTGAA AAGGCCTTCA AATTCATCCC    120

GGGCCCACTG AAGAGTGTGT TCGATGGCAT TGGGAAAGTT TTTCAGGGTA CAAATGGGGA    180

TGGATTTCTC TGGTGGATCC TGGCTAGACG TGATGGATTC TGTCAGGAAG GGGATTACCA    240

CCTGCACGTT GCCCTTT                                                   257
```

(2) INFORMATION FOR SEQ ID NO: 55:

(i) SEQUENCE CHARACTERISTICS:
(A) LENGTH: 298 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 55:

```
TTAGCACCTC ACACTCACAT GCCCTTCTAC ATAGAGACTG GTTAAACAGC CCTCCCTCCC     60

TTGTCCCGAC TTGACTTCCA GGCCCCTCTG CTTTCCTCTC ACAACCACAC CAGGTCTGAT    120

GGAGTCCAGT GCCTGCAGTG ACCCAACATA GACTGCACTT TCACCTACCT ACTGGATGGT    180

CCTGCAGCCC AGACGGCTGC TCTTCTTTCT CATGGAGTTT CTCTCCTGCC TGAGATATGC    240

TATCTGGTCT GCCCCTGTGT AGCTCCCATG GGATCCCTTA AAATCGATCC TTTTTTAA      298
```

(2) INFORMATION FOR SEQ ID NO: 56:

(i) SEQUENCE CHARACTERISTICS:
(A) LENGTH: 337 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

-continued (xi) SEQUENCE DESCRIPTION: SEQ ID NO: 56:

TTAGCACCTC GTGAGGAGAC TGTTGTCCAC AGGCCAGCTA GTGGTACCCT ACTGAGAAGT 60

TGGGTTTTGG TTTTGTTTCC CTTGAAGGGT CGCTGTTAGA GGATGGAAGT AACTTCTAAT 120

TCTTGATCTG TTTGTTGGTC TTGTTTTCAG TACTTTTTGC CAGTTGTATA CACTTGGAGA 180

GGGAATTTGT ATGCCTGTAA TCTTGTTCTT GAGGTCAGAA ATTCAAAACA TTGGGAGCTT 240

TTGTTGTAAA GGTTAAACTG TGAATCCATA TAGCAAATGC AGATCCTTTT ACAGTGTAAA 300

CCACATTTCC TGCCTCAGCC TAAAGCACTG GTCATTT 337

(2) INFORMATION FOR SEQ ID NO: 57:

(i) SEQUENCE CHARACTERISTICS:
(A) LENGTH: 333 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 57:

ACCTGCATGC CTAAAGGAGT AGGCTTAGGG GTGGGGAGAG AGAAGGCATA GGCTTTTCTA 60

GTTATACAAA GCTGTGTAAG GCAAGGTTCC TTTCTACTAA ATGGTCAGCT GTCACTACAT 120

TTATACTTTT GTATGTCATA AACCCTTTCT TTCATTCCTC CCTGGGTAAC CAGGACAATC 180

GGAGGGCAGT GTGTTACTGG GATTAGAGGA CTAGCAATAC TGGGTAACCC GCCTAAGCTG 240

GAAGGTGACG TAATACGTTT CTTTAAAGAT TCAGTCAGTC AAGCAGTTTA GCAATATCAA 300

AATGTCTGGC TGTTTGGTCC AGTGTACACT GTT 333

(2) INFORMATION FOR SEQ ID NO: 58:

(i) SEQUENCE CHARACTERISTICS:
(A) LENGTH: 296 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 58:

GCTATCTGCG AAACTACAGA AAGGAAGACA GCTTGGCCCA GCGCGGTGAA GTTCAGAATT 60

CACTAGGTAG TTGTTGTTGG TTGACTTGGA GGTAGCTGGG TAATCAACAG CTTTCACTTT 120

AGATTCAATG TGAACCGCAG AGTTACTCAT GACCAAGAGT CTGGCAAACT CATTAATGCT 180

GTTTAATACT TGTTTGATAT TTTTTCACCT TTTGAGCCCT TTTCCCAAAG AATTCAATAT 240

CAGTTTAGTA GCAACAGTAC AGTTGCCATT TAAATTGGTT TAGTTGCAGT ATAGCA 296

-continued (2) INFORMATION FOR SEQ ID NO: 59:

(i) SEQUENCE CHARACTERISTICS:
(A) LENGTH: 296 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 59:

GCTATCTGCG AAACTACAGA AAGGAAGACA GCTTGGCCCA GCGCGGTGAA GTTCAGAATT 60

CACTAGGTAG TTGTTGTTGG TTGACTTGGA GGTAGCTGGG TAATCAACAG CTTTCACTTT 120

AGATTCAATG TGAACCGCAG AGTTACTCAT GACCAAGAGT CTGGCAAACT CATTAATGCT 180

GTTTAATACT TGTTTGATAT TTTTTCACCT TTTGAGCCCT TTTCCCAAAG AATTCAATAT 240

CAGTTTAGTA GCAACAGTAC AGTTGCCATT TAAATTGGTT TAGTTGCAGT ATAGCA 296

(2) INFORMATION FOR SEQ ID NO: 60:

(i) SEQUENCE CHARACTERISTICS:
(A) LENGTH: 273 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 60:

GCTATACTGC AACTAAACCA ATTTAAATGG CAACTGTACT GTTGCTACTA AACTGATATT 60

GAATTCTTTG GGAAAAGGGC TCAAAAGGTG AAAAAATATC AAACAAGTAT TAAACAGCAT 120

TAATGAGTTT GCCAGACTCT TGGTCATGAG TAACTCTGCG GTTCACATTG AATCTAAAGT 180

GAAAGCTGTT GATTACCCAG CTACCTCCAA GTCAACCAAC AACAACTACC TAGTGAATTC 240

TGAACTTCAC CGCGCTGGGC CAAGCTGTCT TCC 273

(2) INFORMATION FOR SEQ ID NO: 61:

(i) SEQUENCE CHARACTERISTICS:
(A) LENGTH: 322 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

-continued (xi) SEQUENCE DESCRIPTION: SEQ ID NO: 61:

GCTATACTGC CCACCACATT GCCACACTCG GAATGACATT TCTATATTTT CACCTCCCCA 60

GATTTCCATT TCTTCATCGT AACTTCCAAT GTGCTCAAAA TATTTTTTAG ATATAGAAAA 120

AAGGCCTCCT GCAAAGGTGG GGGTCTTAAT TGGGTAGGTT TCATCTTTCC TTCTTTGCTT 180

CTCATGATCA GGAAGTGACT CCCAGCCAAA GGAAAGGCTC CAGTCAAAAT TTCCACGGTT 240

ATGGTTGCTT CCGTACGGAG AAGGCTTGTT GAATTCAAAT GTGTTTAGAT CTATGGATGC 300

GATGTCTGGA CTCACCACGG CA 322

(2) INFORMATION FOR SEQ ID NO: 62:

(i) SEQUENCE CHARACTERISTICS:
(A) LENGTH: 262 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 62:

GCTATACTGC TGAAGGAGAT CATTTTGGTG GATGATGCTA GTGTAGACGA CTACCTGCAT 60

GAAAAGCTGG AGGAATACAT AAAACAGTTT TCTATTGTGA AAATAGTCAG GCAGCAAGAA 120

AGGAAAGGCC TGATCACCGC GCGGTTGCTA GGGGCAGCTG TAGCAACTGC CGAGACGCTC 180

ACGTTCTTAG ATGCTCACTG TGAGTGCTTC TATGGCTGGC TGGAACCTCT GCTGGCCAGG 240

ATAGCTGAGA ACTACACTGC CG 262

(2) INFORMATION FOR SEQ ID NO: 63:

(i) SEQUENCE CHARACTERISTICS:
(A) LENGTH: 295 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 63:

AGTTGCCAGG GGGCAGCTCA CGGCGCAGCT CATCCTCTGT GATGTAATTC TTATCTCCAG 60

CCAGGATCTT GAAGGAAGCC ATGACCTGAT CTGCAGTATC AGTATCTGCC GTCTCTCGGG 120

ACATAAAGTC GATGAAGGCC TGGAACGTCA CTACCCCCAA GCGGTTGGGG TCTACAATGC 180

TCATGATTCG GGCAAACTCT GCCTCTCCCA TGTTGTAACC CATGGAGATA AGGCAGGCGC 240

GGAAATCGTC TGTGTCCATC ATGCCCGTCT TCTTCCGGTC AAAGTGGTTG AAAGA 295

(2) INFORMATION FOR SEQ ID NO: 64:

-continued (i) SEQUENCE CHARACTERISTICS:
(A) LENGTH: 287 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 64:

AAGCCGTGTC GCTGAACTGG GAGGACACAC TGCTCACCCT AGAAGGCTCT GGCTGACCCT 60

CCGCCCGGTT AAACAGGGAC TTTGTGGCCA TGTGCTGGCG ACACAGGTCC TGGTACTCAA 120

AAGTAGTGTC ACCATGGGCC CCCTCCGGCC CCAGCGCTGC CAGGCGTCCT TATCCCGCTG 180

TCTCGAATGA TGGCGCATAC CAAGGCCACT GAAAGCCACT AGCAGCCCAG CGACGCCTGC 240

CAGGGCCACT AGAGTAAGCA GCACTGAGCG CATGGGAGAT ATGCCAT 287

(2) INFORMATION FOR SEQ ID NO: 65:

(i) SEQUENCE CHARACTERISTICS:
(A) LENGTH: 332 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 65:

AAGCCGTGTC TGGACGTCCG TGTGTCCGGC TCTTGCTCAC GCAGTCATGG CCTCCGGAAC 60

GCGCAAATCG GAAAGTCGGC TCCTGACTTC ACGGCCACAG CGGTGGTGGA TGGTGCCTTC 120

AAGGAAATCA AGCTTTCGGA CTACAGAGGG AAGTACGTTG TCCTCTTTTT CTACCCACTG 180

GACTTCACTT TTGTTTGCCC CACGGAGATC ATCGCTTTTA GCGACCATGC TGAGGACTTC 240

CGAAAGCTAG GCTGCGAGGT GCTGGGAGTG TCTGTGGACT CTCAGTTCAC CCACCTGGCG 300

TGGATCAATA CCCCACGGAA AGAGGGAGGC TT 332

(2) INFORMATION FOR SEQ ID NO: 66:

(i) SEQUENCE CHARACTERISTICS:
(A) LENGTH: 331 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

-continued (vi) ORIGINAL SOURCE:

(xi) SEQUENCE DESCRIPTION: SEQ ID NO: 66:

AAGCCGTGTC GGAGGGCACC AAGGCTGTCA CCAAGTACAC CAGCTCCAAG TGAGTGCTCA 60

AGACTCAGCT CTTAACCCAA AGGCTCTTTT CAGAGCCACT CAAGACTTCA AAATTGGAGC 120

TTTAATGCTG ACTTAGTGAC TACCGGGAAA ATAACTGACT TCATCTGCAG GATTGTGTAC 180

AAACACTTAT GGTTTAGTAA ATCGAAAAGA TAGACATTGC CCATCAGTTC TGTCTGGTCC 240

ACTTAAATAT GCTTTTTTCT TAGAAGTTCT AAGAACCCTG TCAATAACCT ATCTAGGTCC 300

AGTCCTTGAG TTCAAAGGCC AAATACCAAT G 331

(2) INFORMATION FOR SEQ ID NO: 67:

(i) SEQUENCE CHARACTERISTICS:
(A) LENGTH: 359 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 67:

CAACGCTCAG GATGTAAGCT GTTTCCAGCA CCTGGTTCAA GCGAATGTAA GAAATAAGAA 60

GGTGTTGAAA GATGCCGTGA ATAACATTAC AGCAAAGGGG ATCACAGATT ACAAGAAAGG 120

CTTTAGCTTT GCCTTCGAAC AGCTACTTAA TTATAATGTT TCCAGAGCTA ATTGCAATAA 180

GATTATCATG TTATTCACGG ATGGAGGAGA AGAGAGAGCC CAGGAGATAT TTGCCAAATA 240

CAATAAAGAC AAAAAAGTCC GTGTGTTTAC ATTTTCCGTC GGTCAACATA ATTATGACAG 300

AGGACCTATT CAGTGGATGG CTTGTGAAAT AAAGGTTACT ATTATGAGAT TCCTCCATT 359

(2) INFORMATION FOR SEQ ID NO: 68:

(i) SEQUENCE CHARACTERISTICS:
(A) LENGTH: 317 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 68:

TCAACGCTCA TCACACCAAG AATCAACTGG TTCTTCAAGT TTGTCTTATT TTCAGATTGG 60

CCAGTGACGT TGAAGACTGG TAGAGTTCCA GTAATGACAA GTCCCAGTTC CAGGGCATCC 120

AAATACACAT TTGTCCATTG AACTTGCTTC GCTTTGTCAC CAGCTAAAAC CATTGGTCTT 180

CCCAGAACAT CTAGATATTC CTGAGTATTG ATTCTTATTG CACCAATGGA GGGAATCTCA 240

TAATAGTAAC CTTTATTTTC ACAAGCCATC CACTGAATAG GTCTCTGTCA TAATTATGTT 300

-continued

GACCGACGGA AATGTAA 317

(2) INFORMATION FOR SEQ ID NO: 69:

(i) SEQUENCE CHARACTERISTICS:
(A) LENGTH: 317 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 69:

TAACGCTCAG GAGAAGAATA GGAATGCAGA GAACTCTGCC ACAGCCCCCA CGCTCCCGGG 60

CAGCACCTCA GCCACCACCG CAACCACCAC CCCTGCTGTA GATGAAAGCA AGCCTTGGAA 120

CCAGTATCGC TTGCCTAAGA CTCTTATACC TGACTCCTAC CGGGTGATCT TGAGACCCTA 180

CCTCACCCCC AACAATCAGG GCCTGTACAT CTTCCAAGGC AACAGTACTG TTCGCTTTAC 240

CTGCAACCAG ACCACGGATG TCATTATCAT CCACAGCAAA AAGCTCAACT ACACCCTCAA 300

AGGAAACCAC AGGGTGG 317

(2) INFORMATION FOR SEQ ID NO: 70:

(i) SEQUENCE CHARACTERISTICS:
(A) LENGTH: 287 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 70:

CGAGTCAGAC GGCTTCAGCA TCGAGACCTG TAAGATCATG GTGGACATGC TGGATGAAGA 60

TGGGAGTGGC AAGCTTGGCC TGAAGGAGTT CTACATCCTC TGGACGAAGA TTCAGAAATA 120

CCAAAAAATC TACCGGGAAA TCGATGTGGA CAGGTCTGGA ACTATGAATT CCTACGAGAT 180

GCGGAAAGCA CTGGAAGAAG CAGGTTTCAA GCTGCCCTGT CAACTCCATC AAGTCATCGT 240

TGCCCGGTTT GCAGACGACG AGCTAATCAT CGACTTTGAC AATTTTG 287

(2) INFORMATION FOR SEQ ID NO: 71:

(i) SEQUENCE CHARACTERISTICS:
(A) LENGTH: 311 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 71:

CGAGTCAGAC AACCTGTTCA AGTGGGGTGG GGACCATCCA CGGAGCAGCC GGCACCGTAT 60

ATGAAGACCT GAGGTACAAA CTCTCCCTAG AGTTCCCCAG CGGCTACCCT TACAACGCAC 120

CCACAGTGAA GTTCCTCACA CCCTGCTACC ACCCCAACGT GGACACCCAG GGCAACATCT 180

GCCTGGACAT CCTCAAGGAT AAGTGGTCTG CACTATATGA TGTCAGGACT ATCTTGCTCT 240

CTATCCAGAG CCTGCTAGGA GAACCCAACA TCGATAGCCT TTGAACACAC ACGCTGCGGA 300

ACTCTGGAAA A 311

(2) INFORMATION FOR SEQ ID NO: 72:

(i) SEQUENCE CHARACTERISTICS:
(A) LENGTH: 352 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 72:

TATGAGTCCG GAGCGACGGC TACGAGTGTG AACTGTTCCA GCCCCGAGCG ACACACCAGA 60

AGTTATGACT ACATGGAAGG AGGGGATATA AGGGTGAGAA GACTGTTCTG TCGCACCCAG 120

TGGTACCTGA GGATTGACAA ACGAGGCAAA GTGAAAGGGA CCCAGGAGAT GAAGAACAGC 180

TACAACATCA TGGAAATCAG GACCGTGGCA GTTGGAATTG TGGCAATCAA AGGGGTGGAA 240

AGTGAATACT ATCTTGCCAT GAACAAGGAA GGGAAACTCT ATGCAAAGAA AGAATGCAAT 300

GAGGATTGCA ACTTCAAAGA ACTGATTCTG GAAAACCATT ATAACACCTA TG 352

(2) INFORMATION FOR SEQ ID NO: 73:

(i) SEQUENCE CHARACTERISTICS:
(A) LENGTH: 317 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 73:

TATGAGTCCG AGGAGGAGCA CAATGCTGGG AGTGTGGAAA GCCAGGTTGT CCCCAGCACA 60

CACCGAGTGA CCGATTCCAA GTTCCATCCA CTCCATGCCA AGATGGATGT CATCAAAAAA 120

-continued

GGCCACGCCA GGGACAGCCA GCGCTACAAA GTTGACTATG AGTCTCAAAG CACAGACACC 180

CAGAACTTCT CCTCCGAGTC TAAGCGGGAG ACAGAATACG GTCCCTGCCG CAGAGAAATG 240

GAGGACACAC TGAATCATCT GAAGTTCCTC AATGTGCTGA GTCCAGAGTC TCACATCCAA 300

ACTGTGACAA GAAGGGG 317

(2) INFORMATION FOR SEQ ID NO: 74:

(i) SEQUENCE CHARACTERISTICS:
(A) LENGTH: 247 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 74:

TCGCCCGGGA CTTCATGCGA TTGAGAAGAT TGTCTACCAA ATATAGAACA GAAAAGATTT 60

ATCCCACAGC CACTGGAGAA AAAGAAGAAA ATGTTAAAAA GAACAGATAT AAGGACATAC 120

TGCCATTTGA TCACAGCCGA GTTAAGTTGA CTTTGAAGAC TCCATCCCAA GATTCAGATT 180

ATATCAATGC AAATTTTATT AAGGGTGTGT ATGGGCCAAA AGCATATGTG GCAACCCAAG 240

GGCCTTT 247

(2) INFORMATION FOR SEQ ID NO: 75:

(i) SEQUENCE CHARACTERISTICS:
(A) LENGTH: 256 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 75:

TGTGGAAAGC CAGGTTGTCC CCAGCACACA CCGAGTGACC GATTCCAAGT TCCATCCACT 60

CCATGCCAAG ATGGATGTCA TCAAAAAAGG CCACGCCAGG GACAGCCAGC GCTACAAAGT 120

TGACTATGAG TCTCAAAGCA CAGACACCCA GAACTTCTCC TCCGAGTCTA AGCGGGAGAC 180

AGAATACGGT CCCTGCCGCA GAGAAATGGA GGACACACTG AATCATCTGA AGTTCCTCAA 240

TGTGCTGAGT CCAGAG 256

(2) INFORMATION FOR SEQ ID NO: 76:

(i) SEQUENCE CHARACTERISTICS:
(A) LENGTH: 383 base pairs
(B) TYPE: nucleic acid
(C) STRANDEDNESS: single
(D) TOPOLOGY: linear -continued (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 76:

```
TGACCATCGA AGTGCAAAGG AAATGACTTG ATTTCATGAA GTATCTCCAG AAGTAACGCT     60

TTGTTTTCTG CATCCTGAAC TTTATTCCCA GTGAAGAGCT GAAAATCTGG ACGCTCAAAA    120

AATGGAAGCA CTTTGGAGAG AGCCCTTAAC TCTATCAGGT ACAGGAAGTA CAAGTTCCTC    180

AGCCTTCGTG GGCCTTCTCC TTCAGTCAGA ATCCCATCAA AGCGCTGCTG GAACTCTGTG    240

ACATTGTGAC CCCATTTCTT TTCCAGCCAA GTATCTTGTA AAAGATACCT TGCACTCAAA    300

TGCACATTAA TGCTTGCGTG CAGGCCAGAT ATAAGTCTGT AGAATCGCTC TTTCTACACA    360

GAGGCCTTCT AGCCAGTTGT AAA                                            383
```

(2) INFORMATION FOR SEQ ID NO: 77:

(i) SEQUENCE CHARACTERISTICS:
(A) LENGTH: 400 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 77:

```
CTGCTTGATG CTAAGCCCGG CAGCCTGTGT TTCATCTACA GGATGCACAA CATAAAAGAA     60

AAGATCTGAT TCCCGCAGGT TCTCTTCTGA CCTACACACA CACACACTAA AATAACATTT    120

AAAAATATGT GCCAAATTAT ATTTGTTCGG GTGCCACCTT CCACCAGCTT ACCACTACGG    180

TAGAACTGTC AAATTCATCT CCCTGAATTT GTCTTAAAGG GGTGTCCATG CACAGGCCCA    240

AGAGTCACCT CCAATGAAAT AAATGTAATA CTGAAGTATG CCATGATGTT TGTTGTTTTC    300

TTTCATCGTA AGCCTGTAAG CAGGAAAAAT AGTAATAGAT AGAATAGAGA CTTACCAGTG    360

GTCGATGGCC TGGTCAGTCT GTGCGGTGAC TAGGACCAGG                          400
```

(2) INFORMATION FOR SEQ ID NO: 78:

(i) SEQUENCE CHARACTERISTICS:
(A) LENGTH: 343 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

-continued (xi) SEQUENCE DESCRIPTION: SEQ ID NO: 78:

```
ACCTGCATGC CGAGTGTGAC GCCTTTGAGG AGAAGATCCA GGCTGCCGGA GGGATCGAAC     60

TCTTTGTCGG AGGCATTGGC CCCGATGGAC ACATTGCCTT CAATGAGCCA GGCTCCAGCC    120

TGGTGTCCAG GACCCGTGTG AAGACTCTGG TTATGGACAC CATCCTGGCC AACGCTAGGT    180

TCTTTGATGG TGATCTTGCC AAGGTGCCCA CCATGGCCCT GACAGTGGGT GTCGGCACTG    240

TCATGGATGC TAAAGAGGTG ATGATCCTCA TCACAGGCGC TCACAAGGCC TTTGCTCTGT    300

ACAAAGCCAT CGATGGAGGC GTGAACCACA TGTGGACGGT GTG                      343
```

(2) INFORMATION FOR SEQ ID NO: 79:

(i) SEQUENCE CHARACTERISTICS:
(A) LENGTH: 337 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 79:

```
GCTATACTGC AATGTTAGGG GAATGAACGC GTTTTCCTAC TGCACTGGGG ACTTTTAGAT     60

AGGTTAATGA AAGGCCTTTT ATTCTGTTAC TGGACACGAA AACTTTGTCT AATTTCTTAT    120

ACTCTATTGT ACGTTTACAG TCGCAGCACT AAAATGGAAG ACATCAAACA TTTTTAACAG    180

AAAAAAAAAA AGATGTAAAA ACTAACTAAG GACTATTTAT TGATAATGTT TTGCTACTCC    240

TGTCAGACAA TGGCTATAAA CTGAATTAGG CAGTCTTAAA AAAAAAAAAA GAAAAAAAAG    300

AAAAAAGAAA AAAAGAAAAG AAAAGAAAAA AAACTGG                             337
```

(2) INFORMATION FOR SEQ ID NO: 80:

(i) SEQUENCE CHARACTERISTICS:
(A) LENGTH: 371 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 80:

```
AGCTAAGGTC GGGTACTCTG ATACTTCAGA GTTTAAAATC ATCAGCCCTT GTAGATCTAT     60

TCCTAAATCT TATGAAAATG CTCAGATGTT TACACAGCTG TGAAACAGGG TCAGTTCAGA    120

TCGCTGATGG CTTGAGAATG TGTTTCTTGT TGACATCAGG AACTGGAAAT GTTTACTTCC    180

CGTCATTTAT GAGTCATCAA GTATCTCGGC TCTTTTAAGA GCGCAAGATA AAACAAGCTT    240

AAACCAGGTG ATAAGAGCAG AGTCCACTTG AGTCTGAGCT CACCCGAGAA CTTGCTATCG    300
```

-continued

AGGACATTTG GAATGGGAGT GTGCAGGCTT CCTTCAGTTA CTGAATGAGT CCATCTGCTA 360

GTCACCTTGA C 371

(2) INFORMATION FOR SEQ ID NO: 81:

(i) SEQUENCE CHARACTERISTICS:
(A) LENGTH: 319 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 81:

AGCTAAGGTC CAGGGGGCAA AGCGGTGACG TGTGCACATC GATATGAGAA ACGGCAGCAC 60

GTCAACACGA AGCAGGAGTC GCGGGATATC TTTGGAAGAT GTTATGTCCT AAGTCAGAAT 120

CTCAGAATTG AAGATGATAT GGACGGAGGA GACTGGAGTT TCTGCGATGG CCGGTTGAGA 180

GGCCATGAAA AGTTTGGCTC CTGTCAGCAA GGAGTAGCGG CTACTTTCAC TAAGGACTTT 240

CATTACATTG TTTTTGGAGC CCCAGGGACT TACAACTGGA AAGGGATCGT CGTGTAGAAC 300

AAAAGAATAA CACTTTTTT 319

(2) INFORMATION FOR SEQ ID NO: 82:

(i) SEQUENCE CHARACTERISTICS:
(A) LENGTH: 368 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 82:

AAGCCGTGTC TGTGCTCAAG GAAGAAACCC ACTGGACCAA CTTCTGTCAG AAAGGAAAAC 60

CTTGTTCAAA GTTTCAGGAC CCTGTTCTTT GCTTATTTGC ACATGGTCAC CTTGGTCTGA 120

GCTAGCCACC ATTGTCACCC ACAGCTGCAA AGAAAGCAGA CCTTAGGAAA CACTGTCACG 180

GCTGAGTGTG ACTGCCTTGT TCATCCCCTG GACTGGTACT GTGTTGCCTG CAGTACCATT 240

GGGATCCCAT AGCAAGAGAG GGAGAGGGAG ATGTTAGTTA GCCTTTGCTA CGAACCAAGC 300

TGTCCCAAGT CTCAACAGCT AAACAGGTAT TCATTTACCA TGATTCTATG GTTAGCTAAG 360

CTCTTGAG 368

(2) INFORMATION FOR SEQ ID NO: 83:

(i) SEQUENCE CHARACTERISTICS:
(A) LENGTH: 340 base pairs
(B) TYPE: nucleic acid
(C) STRANDEDNESS: single -continued (D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 83:

```
CTTTCTACCC TGGAGGATGT GCTTGAGGCA CACTGCTCCT GTGCTCTCCA CTTGAGGCAT     60

AAGCCCAGTC AGTTGTGCAT AGATGATTAA CCTCTGACCC CTAAAGATGG TAAGTTGCTC    120

TGGAGAAAGC ATTTTAACAG ACAAACCAGG AGGCAAATCC CAACTTAGAG AGATGTTATC    180

CACTGCACAC TGTAGAGCAA ACTTGAGAGA CCCAAGAGCC TTGGTCTGCA TCCTGTCCTT    240

GCCTGTGATA AACACTCGAG TACCCCCTGA TACCGGGCGA TATTTTTGAT TAACTGGTCG    300

AGGCTCCTTG TCCAATTCCA AAAGAGAACA TCTGTGTTTC                          340
```

(2) INFORMATION FOR SEQ ID NO: 84:

(i) SEQUENCE CHARACTERISTICS:
(A) LENGTH: 252 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 84:

```
TGGTAAAGGG CATCTGTAAA TACACTCTAT GAGGAAATTA AAACTTGAAC ATGGCAGTCT     60

GACATTGCAA AACAAAACAA AACAAAACTG ACCCTCCAAT AGCAGCGAAA ACAACGTGAA    120

AGATACAAAG CAATGAGAAT CTGGTTCTGA ACGCCTGGGA TCCTGGGAGT CATCGGTAGC    180

AGCGCCATGA GAGGAGCCGT GGCCTGTCCC ATGTGGTCCC ACCTTCACCT CTTCCCTCAC    240

ATCCCTCTTA AG                                                        252
```

(2) INFORMATION FOR SEQ ID NO: 85:

(i) SEQUENCE CHARACTERISTICS:
(A) LENGTH: 348 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 85:

```
TGGTAAAGGG GGCAAGGGCA AAGGCACGGG AGACAGAGGC CACTGCATCT GTACCCACAT     60
```

-continued

CAGACATGTT TGTCCATTTT CTCTCATTTG GCCTTAGACC ATTGGCAAGA GTAAATGCTC 120

TTAGTCCCGT TATCTAGAAA TTTCTTCCTT TGGGGAGAAC CACTTATAGA CAATATCAGC 180

TCTCTACAAA TAACACGAAA GGTCGTAACA CAGCAAGTGA CCAGAAAGTG CCCGTCCTTG 240

CGGCTCTGAT CCACGTGGCT CTCCGTAGAC AAATTGTTTT TTCTTGTAGG GATATCTGTT 300

TTGCTTCTGA ACTTTCTTAC AAGTGTTTGG GACTCTTCGG GTGGCGTT 348

(2) INFORMATION FOR SEQ ID NO: 86:

(i) SEQUENCE CHARACTERISTICS:
(A) LENGTH: 351 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 86:

TGGTAAAGGG TCAAGTGTTC GATCAGAGTG GAGCTCCATT ACCGAATGTA ATCGTGGAAG 60

TCCAAGACAG AAAGCATATC TGCCCGTTTA GAACCAACAA GCTTGGAGAA TACTATCTGC 120

TTCTGCTGCC CGGGTCCTAC GTGATCAATG TTACAGTCCC TGGACACGAC TCCTACCTCA 180

CGAAGCTTAC TATTCCAGGG AAATCCCAGC CCTTCAGTGC TCTTAAAAAG GATTTTCACC 240

TCCCGCTGCG ATGGCAGCCG GATTCCATCT CCGTATCCAA TCCTTCGTGC CGATGATTCC 300

GCTGTACAAA TTCATGCCAA GCCACTCGGC TGCCACAAAG CCTAGTCTGG G 351

(2) INFORMATION FOR SEQ ID NO: 87:

(i) SEQUENCE CHARACTERISTICS:
(A) LENGTH: 242 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 87:

GAATTCGGCT TTCTGCGATC CACTCTTTGA AGCTATTGGC AAGATATTCA GCAACATCCG 60

CATCAGCACG CAGAAAGAGA TATGAGGGAC ATTTCAAGGA TGAAAGGTTT TTTTCCCCCC 120

TTACTATTTC CTTGGTGCCA ATTCCAAGTT GCTCTCGCAG CAGCAAATTT ATGAATGGTT 180

TGTCTTGATC AAGAACAAAG AATTCATTCC CACCATTCTC ATATATACTA CTTTCTCTTC 240

TT 242

(2) INFORMATION FOR SEQ ID NO: 88:

(i) SEQUENCE CHARACTERISTICS:

-continued (A) LENGTH: 240 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 88:

```
GAATTCGGCT TTCTGCGATC CACTCTTTGA AGCTATTGGC AAGATATTCA GCAACATCCG     60

CATCAGCACG CAGAAAGAGA TATGAGGGAC ATTTCAAGGA TGAAAGGTTT TTTTCCCCCC    120

TTACTATTTC CTTGGTGCCA ATTCCAAGTT GCTCTCGCAG CAGCAAATTT ATGAATGGTT    180

TGTCTTGATC AAGAACAAAG AATTCATTCC ACCATTCTCA TATATCTACG TCTCTTCTAG    240
```

(2) INFORMATION FOR SEQ ID NO: 89:

(i) SEQUENCE CHARACTERISTICS:
(A) LENGTH: 687 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 89:

```
ACGAGGGGAA ACCTCCTCAG AGCCTGCAGC CAGCCACGCG CCAGCATGTC TGGGGGCAAA     60

TACGTAGACT CCGAGGGACA TCTCTACACT GTTCCCATCC GGGAACAGGG CAACATCTAC    120

AAGCCCAACA ACAAGGCCAT GGCAGACGAG GTGACTGAGA AGCAAGTGTA TGACGCGCAC    180

ACCAAGGAGA TTGACCTGGT CAACCGCGAC CCCAAGCATC TCAACGACGA CGTGGTCAAG    240

ATTGACTTTG AAGATGTGAT TGCAGAACCA GAAGGGACAC ACAGTTTCGA CGGCATCTGG    300

AAGGCCAGCT TCACCACCTT CACTGTGACA AAATATTGGT TTTACCGCTT GTTGTCTACG    360

ATCTTCGGCA TCCCAATGGC ACTCATCTGG GGCATTTACT TTGCCATTCT CTCCTTCCTG    420

CACATCTGGG CGGTTGTACC GTGCATCAAG AGCTTCCTGA TTGAGATTCA GTGCATCAGC    480

CGCGTCTACT CCATCTACGT CCATACCTTC TGCGATCCAC TCTTTGAAGC TATTGGCAAG    540

ATATTCAGCA ACATCCGCAT CAGCACGCAG AAAGAGATAT GAGGGACATT TCAAGGATGA    600

AAGGTTTTTT TCCCCCCTTA CTATTTCCTT GGTGCCAATT CCAAGTTGCT CTCGCAGCAG    660

CAAATTTATG AATGGTTTGT CTTGATC                                        687
```

(2) INFORMATION FOR SEQ ID NO: 90:

(i) SEQUENCE CHARACTERISTICS:
(A) LENGTH: 560 amino acids
(B) TYPE: amino acid
(C) STRANDEDNESS: single
(D) TOPOLOGY: linear -continued (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 90:

```
Met Glu Cys Leu Tyr Tyr Phe Leu Gly Phe Leu Leu Leu Ala Ala Arg
1               5                   10                  15

Leu Pro Leu Asp Ala Ala Lys Arg Phe His Asp Val Leu Gly Asn Glu
            20                  25                  30

Arg Pro Ser Ala Tyr Met Arg Glu His Asn Gln Leu Asn Gly Trp Ser
        35                  40                  45

Ser Asp Glu Asn Asp Trp Asn Glu Lys Leu Tyr Pro Val Trp Lys Arg
    50                  55                  60

Gly Asp Met Arg Trp Lys Asn Ser Trp Lys Gly Gly Arg Val Gln Ala
65                  70                  75                  80

Val Leu Thr Ser Asp Ser Pro Ala Leu Val Gly Ser Asn Ile Thr Phe
                85                  90                  95

Ala Val Asn Leu Ile Phe Pro Arg Cys Gln Lys Glu Asp Ala Asn Gly
            100                 105                 110

Asn Ile Val Tyr Glu Lys Asn Cys Arg Asn Glu Ala Gly Leu Ser Ala
        115                 120                 125

Asp Pro Tyr Val Tyr Asn Trp Thr Ala Trp Ser Glu Asp Ser Asp Gly
    130                 135                 140

Glu Asn Gly Thr Gly Gln Ser His His Asn Val Phe Pro Asp Gly Lys
145                 150                 155                 160

Pro Phe Pro His His Pro Gly Trp Arg Arg Trp Asn Phe Ile Tyr Val
                165                 170                 175

Phe His Thr Leu Gly Gln Tyr Phe Gln Lys Leu Gly Arg Cys Ser Val
            180                 185                 190

Arg Val Ser Val Asn Thr Ala Asn Val Thr Leu Gly Pro Gln Leu Met
        195                 200                 205

Glu Val Thr Val Tyr Arg Arg His Gly Arg Ala Tyr Val Pro Ile Ala
    210                 215                 220

Gln Val Lys Asp Val Tyr Val Val Thr Asp Gln Ile Pro Val Phe Val
225                 230                 235                 240

Thr Met Phe Gln Lys Asn Asp Arg Asn Ser Ser Asp Glu Thr Phe Leu
                245                 250                 255

Lys Asp Leu Pro Ile Met Phe Asp Val Leu Ile His Asp Pro Ser His
            260                 265                 270

Phe Leu Asn Tyr Ser Thr Ile Asn Tyr Lys Trp Ser Phe Gly Asp Asn
        275                 280                 285

Thr Gly Leu Phe Val Ser Thr Asn His Thr Val Asn His Thr Tyr Val
    290                 295                 300

Leu Asn Gly Thr Phe Ser Leu Asn Leu Thr Val Lys Ala Ala Ala Pro
305                 310                 315                 320

Gly Pro Cys Pro Pro Pro Pro Pro Pro Pro Arg Pro Ser Lys Pro Thr
                325                 330                 335

Pro Ser Leu Gly Pro Ala Gly Asp Asn Pro Leu Glu Leu Ser Arg Ile
            340                 345                 350

Pro Asp Glu Asn Cys Gln Ile Asn Arg Tyr Gly His Phe Gln Ala Thr
```

-continued

```
        355                 360                 365

Ile Thr Ile Val Glu Gly Ile Leu Glu Val Asn Ile Ile Gln Met Thr
    370                 375                 380

Asp Val Leu Met Pro Val Pro Trp Pro Glu Ser Ser Leu Ile Asp Phe
385                 390                 395                 400

Val Val Thr Cys Gln Gly Ser Ile Pro Thr Glu Val Cys Thr Ile Ile
                405                 410                 415

Ser Asp Pro Thr Cys Glu Ile Thr Gln Asn Thr Val Cys Ser Pro Val
            420                 425                 430

Asp Val Asp Glu Met Cys Leu Leu Thr Val Arg Arg Thr Phe Asn Gly
        435                 440                 445

Ser Gly Thr Tyr Cys Val Asn Leu Thr Leu Gly Asp Asp Thr Ser Leu
    450                 455                 460

Ala Leu Thr Ser Thr Leu Ile Ser Val Pro Asp Arg Asp Pro Ala Ser
465                 470                 475                 480

Pro Leu Arg Met Ala Asn Ser Ala Leu Ile Ser Val Gly Cys Leu Ala
                485                 490                 495

Ile Phe Val Thr Val Ile Ser Leu Leu Val Tyr Lys Lys His Lys Glu
            500                 505                 510

Tyr Asn Pro Ile Glu Asn Ser Pro Gly Asn Val Val Arg Ser Lys Gly
        515                 520                 525

Leu Ser Val Phe Leu Asn Arg Ala Lys Ala Val Phe Phe Pro Gly Asn
    530                 535                 540

Gln Glu Lys Asp Pro Leu Leu Lys Asn Gln Glu Phe Lys Gly Val Ser
545                 550                 555                 560
```

(2) INFORMATION FOR SEQ ID NO: 91:

(i) SEQUENCE CHARACTERISTICS:
(A) LENGTH: 2669 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 91:

```
CAGATGCCAG AAGAACACTG TTGCTCTTGG TGGACGGGCC CAGAGGAATT CAGAGTTAAA     60

CCTTGAGTGC CTGCGTCCGT GAGAATTCAG CATGGAATGT CTCTACTATT TCCTGGGATT    120

TCTGCTCCTG GCTGCAAGAT TGCCACTTGA TGCCGCCAAA CGATTTCATG ATGTGCTGGG    180

CAATGAAAGA CCTTCTGCTT ACATGAGGGA GCACAATCAA TTAAATGGCT GGTCTTCTGA    240

TGAAAATGAC TGGAATGAAA AACTCTACCC AGTGTGGAAG CGGGGAGACA TGAGGTGGAA    300

AAACTCCTGG AAGGGAGGCC GTGTGCAGGC GGTCCTGACC AGTGACTCAC CAGCCCTCGT    360

GGGCTCAAAT ATAACATTTG CGGTGAACCT GATATTCCCT AGATGCCAAA AGGAAGATGC    420

CAATGGCAAC ATAGTCTATG AGAAGAACTG CAGAAATGAG GCTGGTTTAT CTGCTGATCC    480

ATATGTTTAC AACTGGACAG CATGGTCAGA GGACAGTGAC GGGGAAAATG GCACCGGCCA    540

AAGCCATCAT AACGTCTTCC CTGATGGGAA ACCTTTTCCT CACCACCCCG GATGGAGAAG    600
```

-continued

```
ATGGAATTTC ATCTACGTCT TCCACACACT TGGTCAGTAT TTCCAGAAAT TGGGACGATG    660
TTCAGTGAGA GTTTCTGTGA ACACAGCCAA TGTGACACTT GGGCCTCAAC TCATGGAAGT    720
GACTGTCTAC AGAAGACATG GACGGGCATA TGTTCCCATC GCACAAGTGA AAGATGTGTA    780
CGTGGTAACA GATCAGATTC CTGTGTTTGT GACTATGTTC CAGAAGAACG ATCGAAATTC    840
ATCCGACGAA ACCTTCCTCA AAGATCTCCC CATTATGTTT GATGTCCTGA TTCATGATCC    900
TAGCCACTTC CTCAATTATT CTACCATTAA CTACAAGTGG AGCTTCGGGG ATAATACTGG    960
CCTGTTTGTT TCCACCAATC ATACTGTGAA TCACACGTAT GTGCTCAATG GAACCTTCAG   1020
CCTTAACCTC ACTGTGAAAG CTGCAGCACC AGGACCTTGT CCGCCACCGC CACCACCACC   1080
CAGACCTTCA AAACCCACCC CTTCTTTAGG ACCTGCTGGT GACAACCCCC TGGAGCTGAG   1140
TAGGATTCCT GATGAAAACT GCCAGATTAA CAGATATGGC CACTTTCAAG CCACCATCAC   1200
AATTGTAGAG GGAATCTTAG AGGTTAACAT CATCCAGATG ACAGACGTCC TGATGCCGGT   1260
GCCATGGCCT GAAAGCTCCC TAATAGACTT TGTCGTGACC TGCCAAGGGA GCATTCCCAC   1320
GGAGGTCTGT ACCATCATTT CTGACCCCAC CTGCGAGATC ACCCAGAACA CAGTCTGCAG   1380
CCCTGTGGAT GTGGATGAGA TGTGTCTGCT GACTGTGAGA CGAACCTTCA ATGGGTCTGG   1440
GACGTACTGT GTGAACCTCA CCCTGGGGGA TGACACAAGC CTGGCTCTCA CGAGCACCCT   1500
GATTTCTGTT CCTGACAGAG ACCCAGCCTC GCCTTTAAGG ATGGCAAACA GTGCCCTGAT   1560
CTCCGTTGGC TGCTTGGCCA TATTTGTCAC TGTGATCTCC CTCTTGGTGT ACAAAAAACA   1620
CAAGGAATAC AACCCAATAG AAAATAGTCC TGGGAATGTG GTCAGAAGCA AAGGCCTGAG   1680
TGTCTTTCTC AACCGTGCAA AAGCCGTGTT CTTCCCGGGA AACCAGGAAA AGGATCCGCT   1740
ACTCAAAAAC CAAGAATTTA AAGGAGTTTC TTAAATTTCG ACCTTGTTTC TGAAGCTCAC   1800
TTTTCAGTGC CATTGATGTG AGATGTGCTG GAGTGGCTAT TAACCTTTTT TTCCTAAAGA   1860
TTATTGTTAA ATAGATATTG TGGTTTGGGG AAGTTGAATT TTTTATAGGT TAAATGTCAT   1920
TTTAGAGATG GGGAGAGGGA TTATACTGCA GGCAGCTTCA GCCATGTTGT GAAACTGATA   1980
AAAGCAACTT AGCAAGGCTT CTTTTCATTA TTTTTTATGT TTCACTTATA AAGTCTTAGG   2040
TAACTAGTAG GATAGAAACA CTGTGTCCCG AGAGTAAGGA GAGAAGCTAC TATTGATTAG   2100
AGCCTAACCC AGGTTAACTG CAAGAAGAGG CGGGATACTT TCAGCTTTCC ATGTAACTGT   2160
ATGCATAAAG CCAATGTAGT CCAGTTTCTA AGATCATGTT CCAAGCTAAC TGAATCCCAC   2220
TTCAATACAC ACTCATGAAC TCCTGATGGA ACAATAACAG GCCCAAGCCT GTGGTATGAT   2280
GTGCACACTT GCTAGACTCA GAAAAAATAC TACTCTCATA AATGGGTGGG AGTATTTTGG   2340
TGACAACCTA CTTTGCTTGG CTGAGTGAAG GAATGATATT CATATATTCA TTTATTCCAT   2400
GGACATTTAG TTAGTGCTTT TTATATACCA GGCATGATGC TGAGTGACAC TCTTGTGTAT   2460
ATTTCCAAAT TTTTGTATAG TCGCTGCACA TATTTGAAAT CATATATTAA GACTTTCCAA   2520
AGATGAGGTC CCTGGTTTTT CATGGCAACT TGATCAGTAA GGATTTCACC TCTGTTTGTA   2580
ACTAAAACCA TCTACTATAT GTTAGACATG ACATTCTTTT TCTCTCCTTC CTGAAAAATA   2640
AAGTGTGGGA AGAGACAAAA AAAAAAAAA                                     2669
```

(2) INFORMATION FOR SEQ ID NO: 92:

(i) SEQUENCE CHARACTERISTICS:
(A) LENGTH: 335 base pairs
(B) TYPE: nucleic acid
(C) STRANDEDNESS: single
(D) TOPOLOGY: linear -continued (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 92:

```
AAGGTGAAAG ATGTGTATGT GATAACAGAT CAGATCCCTG TATTCGTGAC CATGTCCCAG     60
AAGAATGACA GGAACTTGTC TGATGAGATC TTCCTCAGAG ACCTCCCCAT CGTCTTCGAT    120
GTCCTCATTC ATGATCCCAG CCACTTCCTC AACGACTCTG CCATTTCCTA CAAGTGGAAC    180
TTTGGGGACA ACACTGGCCT GTTTGTCTCC AACAATCACA CTTTGAATCA CACTTATGTG    240
CTCAATGGAA CCTTCAACCT TAACCTCACC GTGCAAACTG CAGTGCCCGG GCCATGCCCT    300
CCCCCTTCGC CTTCGACTCC GCCTCCACCT TCGTA                               335
```

(2) INFORMATION FOR SEQ ID NO: 93:

(i) SEQUENCE CHARACTERISTICS:
(A) LENGTH: 262 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 93:

```
AAGGTGAAAG ATGTGTATGT GATAACAGAT CAGATCCCTG TATTCGTGAC CATGTCCCAG     60
AAGAATGACA GGAACTTGTC TGATGAGATC TTCCTCAGAG ACCTCCCCAT CGTCTTCGAT    120
GTCCTCATTC ATGATCCCAG CCACTTCCTC AACGACTCTG CCATTTCCTA CAAGTGGAAC    180
TTTGGGGACA ACACTGGCCT GTTTGTCTCC AACAATCACA CTTTGAATCA CACTTATGTG    240
CTCAATGGAA CCTTCAACCT TA                                             262
```

(2) INFORMATION FOR SEQ ID NO: 94:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 94:

```
AAGGTGAAAG ATGTGTATGT GATAACAGAT CAGATCCCTG TATTCGTGAC CATGTCCCAG     60
AAGAATGACA GGAACTTGTC TGATGAGATC TTCCTCAGAG ACCTCCCCAT CGTCTTCGAT    120
```

-continued

GTCCTCATTC ATGATCCCAG CCACTTCCTC AACGACTCTG CCATTTCCTA CAAGTGGAAC 180

TTTGGGGACA ACACTGGCCT GTTTGTCTCC AACAATCACA CTTTGAATCA CACTTATGTG 240

CTCAATGGAA CCTTCAACCT TAACCTCACC GTGCAAACTG CAGTGCCCGG GCCATGCCCT 300

CCCCCTTCGC CTTCGACTCC GCCTCCACCT TCGTA 335

(2) INFORMATION FOR SEQ ID NO: 95:

(i) SEQUENCE CHARACTERISTICS:
(A) LENGTH: 190 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 95:

TACGAAGGTG GAGGCGGAGT CGAAGGCGAA GGGGGAGGGC ATGGCCCGGG CACTGCAGTT 60

TGCACGGTGA GGTTAAGGTT GAAGGTTCCA TTGAGCACAT AAGTGTGATT CAAAGTGTGA 120

TTGTTGGAGA CAAACAGGCC AGTGTTGTCC CCAAAGTTCC ACTTGTAGGA AATGGCAGAG 180

TCGTTGAGGA 190

(2) INFORMATION FOR SEQ ID NO: 96:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 96:

AAGGTGAAAG ATGTGTATGT GATAACAGAT CAGATCCCTG TATTCGTGAC CATGTCCCAG 60

AAGAATGACA GGAACTTGTC TGATGAGATC TTCCTCAGAG ACCTCCCCAT CGTCTTCGAT 120

GTCCTCATTC ATGATCCCAG CCACTTCCTC AACGACTCTG CCATTTCCTA CAAGTGGAAC 180

TTTGGGGACA ACACTGGCCT GTTTGTCTCC AACAATCACA CTTTGAATCA CACTTATGTG 240

CTCAATGGAA CCTTCAACCT TAACCTCACC GTGCAAACTG CAGTGCCCGG GCCATGCCCT 300

CCCCCTTCGC CTTCGACTCC GCCTCCACCT TCGTA 335

(2) INFORMATION FOR SEQ ID NO: 97:

(i) SEQUENCE CHARACTERISTICS:
(A) LENGTH: 74 amino acids
(B) TYPE: amino acid
(C) STRANDEDNESS: single
(D) TOPOLOGY: linear -continued (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 97:

```
Arg Arg Trp Arg Arg Ser Arg Arg Arg Arg Gly Arg Ala Trp Gly His
1               5                   10                  15

Cys Ser His Gly Val Lys Val Gly Ser His Ser Val Ser Val Val Gly
            20                  25                  30

Asp Lys Ala Ser Val Val Lys Val Val Gly Asn Gly Arg Val Val Val
        35                  40                  45

Ala Gly Met Asn Asp Asp Asp Gly Val Ser Asp Arg Val Val Gly His
    50                  55                  60

Gly His Tyr Arg Asp Cys Tyr His His His
65                  70
```

(2) INFORMATION FOR SEQ ID NO: 98:

(i) SEQUENCE CHARACTERISTICS:
(A) LENGTH: 71 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 98:

```
Lys Val Lys Asp Val Tyr Val Thr Asp Val Val Thr Met Ser Lys Asn
1               5                   10                  15

Asp Arg Asn Ser Asp Arg Asp Val Asp Val His Asp Ser His Asn Asp
            20                  25                  30

Ser Ala Ser Tyr Lys Trp Asn Gly Asp Asn Thr Gly Val Ser Asn Asn
        35                  40                  45

His Thr Asn His Thr Tyr Val Asn Gly Thr Asn Asn Thr Val Thr Ala
    50                  55                  60

Val Gly Cys Ser Ser Thr Ser
65                  70
```

(2) INFORMATION FOR SEQ ID NO: 99:

(i) SEQUENCE CHARACTERISTICS:
(A) LENGTH: 75 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO -continued (v) FRAGMENT TYPE: N-terminal (vi) ORIGINAL SOURCE:

(xi) SEQUENCE DESCRIPTION: SEQ ID NO: 99:

```
Tyr Gly Gly Gly Gly Val Gly Gly Gly Gly His Gly Gly Thr Ala Val
1               5                   10                  15

Cys Thr Val Arg Arg Lys Val Ser Thr Val Lys Val Thr Asn Arg Val
            20                  25                  30

Ser Lys His Met Ala Ser Arg Lys Trp Gly Ser Met Arg Thr Ser Lys
        35                  40                  45

Thr Met Gly Arg Ser Arg Lys Ser Ser Asp Lys Ser Trp Asp Met Val
    50                  55                  60

Thr Asn Thr Gly Ser Val Thr Tyr Thr Ser Thr
65                  70                  75
```

(2) INFORMATION FOR SEQ ID NO: 100:

(i) SEQUENCE CHARACTERISTICS:
(A) LENGTH: 376 amino acids
(B) TYPE: amino acid
(C) STRANDEDNESS: single
(D) TOPOLOGY: linear (ii) MOLECULE TYPE: peptide (iii) HYPOTHETICAL: NO (iv) ANTI-SENSE: NO (v) FRAGMENT TYPE: N-terminal (vi) ORIGINAL SOURCE:

(xi) SEQUENCE DESCRIPTION: SEQ ID NO: 100:

```
Met Cys Tyr Tyr Gly Ala Ala Arg Asp Ala Ala Lys Arg His Asp Val
1               5                   10                  15

Gly Asn Arg Ser Ala Tyr Met Arg His Asn Asn Gly Trp Ser Ser Asp
            20                  25                  30

Asn Asp Trp Asn Lys Tyr Val Trp Lys Arg Gly Asp Met Arg Trp Lys
        35                  40                  45

Asn Ser Trp Lys Gly Gly Arg Val Ala Val Thr Ser Asp Ser Ala Val
    50                  55                  60

Gly Ser Asn Thr Ala Val Asn Arg Cys Lys Asp Ala Asn Gly Asn Val
65                  70                  75                  80

Tyr Lys Asn Cys Arg Asn Ala Gly Ser Ala Asp Tyr Val Tyr Asn Trp
                85                  90                  95

Thr Ala Trp Ser Asp Ser Asp Gly Asn Gly Thr Gly Ser His His Asn
            100                 105                 110

Val Asp Gly Lys His His Gly Trp Arg Arg Trp Asn Tyr Val His Thr
        115                 120                 125

Gly Tyr Lys Gly Arg Cys Ser Val Arg Val Ser Val Asn Thr Ala Asn
    130                 135                 140

Val Thr Gly Met Val Thr Val Tyr Arg Arg His Gly Arg Ala Tyr Val
145                 150                 155                 160

Ala Val Lys Asp Val Tyr Val Val Thr Asp Val Val Thr Met Lys Asn
                165                 170                 175

Asp Arg Asn Ser Ser Asp Thr Lys Asp Met Asp Val His Asp Ser His
            180                 185                 190

Asn Tyr Ser Thr Asn Tyr Lys Trp Ser Gly Asp Asn Thr Gly Val Ser
```

-continued

```
        195                 200                 205

Thr Asn His Thr Val Asn His Thr Tyr Val Asn Gly Thr Ser Asn Thr
    210                 215                 220

Val Lys Ala Ala Ala Gly Cys Arg Ser Lys Thr Ser Gly Ala Gly Asp
225                 230                 235                 240

Asn Ser Arg Asp Asn Cys Asn Arg Tyr Gly His Ala Thr Thr Val Gly
                245                 250                 255

Val Asn Met Thr Asp Val Met Val Trp Ser Ser Asp Val Val Thr Cys
            260                 265                 270

Gly Ser Thr Val Cys Thr Ser Asp Thr Cys Thr Asn Thr Val Cys Ser
        275                 280                 285

Val Asp Val Asp Met Cys Thr Val Arg Arg Thr Asn Gly Ser Gly Thr
    290                 295                 300

Tyr Cys Val Asn Thr Gly Asp Asp Thr Ser Ala Thr Ser Thr Ser Val
305                 310                 315                 320

Asp Arg Asp Ala Ser Arg Met Ala Asn Ser Ala Ser Val Gly Cys Ala
                325                 330                 335

Val Thr Val Ser Val Tyr Lys Lys His Lys Tyr Asn Asn Ser Gly Asn
            340                 345                 350

Val Val Arg Ser Lys Gly Ser Val Asn Arg Ala Lys Ala Val Gly Asn
        355                 360                 365

Lys Asp Lys Asn Lys Gly Val Ser
    370                 375
```

(2) INFORMATION FOR SEQ ID NO: 101:

(i) SEQUENCE CHARACTERISTICS:
(A) LENGTH: 2669 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 101:

```
CAGATGCCAG AAGAACACTG TTGCTCTTGG TGGACGGGCC CAGAGGAATT CAGAGTTAAA     60

CCTTGAGTGC CTGCGTCCGT GAGAATTCAG CATGGAATGT CTCTACTATT TCCTGGGATT    120

TCTGCTCCTG GCTGCAAGAT TGCCACTTGA TGCCGCCAAA CGATTTCATG ATGTGCTGGG    180

CAATGAAAGA CCTTCTGCTT ACATGAGGGA GCACAATCAA TTAAATGGCT GGTCTTCTGA    240

TGAAAATGAC TGGAATGAAA AACTCTACCC AGTGTGGAAG CGGGGAGACA TGAGGTGGAA    300

AAACTCCTGG AAGGGAGGCC GTGTGCAGGC GGTCCTGACC AGTGACTCAC CAGCCCTCGT    360

GGGCTCAAAT ATAACATTTG CGGTGAACCT GATATTCCCT AGATGCCAAA AGGAAGATGC    420

CAATGGCAAC ATAGTCTATG AGAAGAACTG CAGAAATGAG GCTGGTTTAT CTGCTGATCC    480

ATATGTTTAC AACTGGACAG CATGGTCAGA GGACAGTGAC GGGGAAAATG GCACCGGCCA    540

AAGCCATCAT AACGTCTTCC CTGATGGGAA ACCTTTTCCT CACCACCCCG GATGGAGAAG    600

ATGGAATTTC ATCTACGTCT TCCACACACT TGGTCAGTAT TTCCAGAAAT TGGGACGATG    660

TTCAGTGAGA GTTTCTGTGA ACACAGCCAA TGTGACACTT GGGCCTCAAC TCATGGAAGT    720
```

-continued

```
GACTGTCTAC AGAAGACATG GACGGGCATA TGTTCCCATC GCACAAGTGA AAGATGTGTA    780
CGTGGTAACA GATCAGATTC CTGTGTTTGT GACTATGTTC CAGAAGAACG ATCGAAATTC    840
ATCCGACGAA ACCTTCCTCA AAGATCTCCC CATTATGTTT GATGTCCTGA TTCATGATCC    900
TAGCCACTTC CTCAATTATT CTACCATTAA CTACAAGTGG AGCTTCGGGG ATAATACTGG    960
CCTGTTTGTT TCCACCAATC ATACTGTGAA TCACACGTAT GTGCTCAATG GAACCTTCAG   1020
CCTTAACCTC ACTGTGAAAG CTGCAGCACC AGGACCTTGT CCGCCACCGC CACCACCACC   1080
CAGACCTTCA AAACCCACCC CTTCTTTAGG ACCTGCTGGT GACAACCCCC TGGAGCTGAG   1140
TAGGATTCCT GATGAAAACT GCCAGATTAA CAGATATGGC CACTTTCAAG CCACCATCAC   1200
AATTGTAGAG GGAATCTTAG AGGTTAACAT CATCCAGATG ACAGACGTCC TGATGCCGGT   1260
GCCATGGCCT GAAAGCTCCC TAATAGACTT TGTCGTGACC TGCCAAGGGA GCATTCCCAC   1320
GGAGGTCTGT ACCATCATTT CTGACCCCAC CTGCGAGATC ACCCAGAACA CAGTCTGCAG   1380
CCCTGTGGAT GTGGATGAGA TGTGTCTGCT GACTGTGAGA CGAACCTTCA ATGGGTCTGG   1440
GACGTACTGT GTGAACCTCA CCCTGGGGGA TGACACAAGC CTGGCTCTCA CGAGCACCCT   1500
GATTTCTGTT CCTGACAGAG ACCCAGCCTC GCCTTTAAGG ATGGCAAACA GTGCCCTGAT   1560
CTCCGTTGGC TGCTTGGCCA TATTTGTCAC TGTGATCTCC CTCTTGGTGT ACAAAAAACA   1620
CAAGGAATAC AACCCAATAG AAAATAGTCC TGGGAATGTG GTCAGAAGCA AAGGCCTGAG   1680
TGTCTTTCTC AACCGTGCAA AAGCCGTGTT CTTCCCGGGA AACCAGGAAA AGGATCCGCT   1740
ACTCAAAAAC CAAGAATTTA AAGGAGTTTC TTAAATTTCG ACCTTGTTTC TGAAGCTCAC   1800
TTTTCAGTGC CATTGATGTG AGATGTGCTG GAGTGGCTAT TAACCTTTTT TTCCTAAAGA   1860
TTATTGTTAA ATAGATATTG TGGTTTGGGG AAGTTGAATT TTTTATAGGT TAAATGTCAT   1920
TTTAGAGATG GGGAGAGGGA TTATACTGCA GGCAGCTTCA GCCATGTTGT GAAACTGATA   1980
AAAGCAACTT AGCAAGGCTT CTTTTCATTA TTTTTTATGT TTCACTTATA AAGTCTTAGG   2040
TAACTAGTAG GATAGAAACA CTGTGTCCCG AGAGTAAGGA GAGAAGCTAC TATTGATTAG   2100
AGCCTAACCC AGGTTAACTG CAAGAAGAGG CGGGATACTT TCAGCTTTCC ATGTAACTGT   2160
ATGCATAAAG CCAATGTAGT CCAGTTTCTA AGATCATGTT CCAAGCTAAC TGAATCCCAC   2220
TTCAATACAC ACTCATGAAC TCCTGATGGA ACAATAACAG GCCCAAGCCT GTGGTATGAT   2280
GTGCACACTT GCTAGACTCA GAAAAAATAC TACTCTCATA AATGGGTGGG AGTATTTTGG   2340
TGACAACCTA CTTTGCTTGG CTGAGTGAAG GAATGATATT CATATATTCA TTTATTCCAT   2400
GGACATTTAG TTAGTGCTTT TTATATACCA GGCATGATGC TGAGTGACAC TCTTGTGTAT   2460
ATTTCCAAAT TTTTGTATAG TCGCTGCACA TATTTGAAAT CATATATTAA GACTTTCCAA   2520
AGATGAGGTC CCTGGTTTTT CATGGCAACT TGATCAGTAA GGATTTCACC TCTGTTTGTA   2580
ACTAAAACCA TCTACTATAT GTTAGACATG ACATTCTTTT TCTCTCCTTC CTGAAAAATA   2640
AAGTGTGGGA AGAGACAAAA AAAAAAAAA                                     2669
```

(2) INFORMATION FOR SEQ ID NO: 102:

(i) SEQUENCE CHARACTERISTICS:
(A) LENGTH: 376 amino acids
(B) TYPE: amino acid
(C) STRANDEDNESS: single
(D) TOPOLOGY: linear (ii) MOLECULE TYPE: peptide (iii) HYPOTHETICAL: NO -continued (iv) ANTI-SENSE: NO (v) FRAGMENT TYPE: N-terminal (vi) ORIGINAL SOURCE:

(xi) SEQUENCE DESCRIPTION: SEQ ID NO: 102:

```
Met Cys Tyr Tyr Gly Ala Ala Arg Asp Ala Ala Lys Arg His Asp Val
1               5                   10                  15

Gly Asn Arg Ser Ala Tyr Met Arg His Asn Asn Gly Trp Ser Ser Asp
            20                  25                  30

Asn Asp Trp Asn Lys Tyr Val Trp Lys Arg Gly Asp Met Arg Trp Lys
        35                  40                  45

Asn Ser Trp Lys Gly Gly Arg Val Ala Val Thr Ser Asp Ser Ala Val
    50                  55                  60

Gly Ser Asn Thr Ala Val Asn Arg Cys Lys Asp Ala Asn Gly Asn Val
65                  70                  75                  80

Tyr Lys Asn Cys Arg Asn Ala Gly Ser Ala Asp Tyr Val Tyr Asn Trp
                85                  90                  95

Thr Ala Trp Ser Asp Ser Asp Gly Asn Gly Thr Gly Ser His His Asn
            100                 105                 110

Val Asp Gly Lys His His Gly Trp Arg Arg Trp Asn Tyr Val His Thr
        115                 120                 125

Gly Tyr Lys Gly Arg Cys Ser Val Arg Val Ser Val Asn Thr Ala Asn
    130                 135                 140

Val Thr Gly Met Val Thr Val Tyr Arg Arg His Gly Arg Ala Tyr Val
145                 150                 155                 160

Ala Val Lys Asp Val Tyr Val Val Thr Asp Val Val Thr Met Lys Asn
                165                 170                 175

Asp Arg Asn Ser Ser Asp Thr Lys Asp Met Asp Val His Asp Ser His
            180                 185                 190

Asn Tyr Ser Thr Asn Tyr Lys Trp Ser Gly Asp Asn Thr Gly Val Ser
        195                 200                 205

Thr Asn His Thr Val Asn His Thr Tyr Val Asn Gly Thr Ser Asn Thr
    210                 215                 220

Val Lys Ala Ala Ala Gly Cys Arg Ser Lys Thr Ser Gly Ala Gly Asp
225                 230                 235                 240

Asn Ser Arg Asp Asn Cys Asn Arg Tyr Gly His Ala Thr Thr Val Gly
                245                 250                 255

Val Asn Met Thr Asp Val Met Val Trp Ser Ser Asp Val Val Thr Cys
            260                 265                 270

Gly Ser Thr Val Cys Thr Ser Asp Thr Cys Thr Asn Thr Val Cys Ser
        275                 280                 285

Val Asp Val Asp Met Cys Thr Val Arg Arg Thr Asn Gly Ser Gly Thr
    290                 295                 300

Tyr Cys Val Asn Thr Gly Asp Asp Thr Ser Ala Thr Ser Thr Ser Val
305                 310                 315                 320

Asp Arg Asp Ala Ser Arg Met Ala Asn Ser Ala Ser Val Gly Cys Ala
                325                 330                 335

Val Thr Val Ser Val Tyr Lys Lys His Lys Tyr Asn Asn Ser Gly Asn
            340                 345                 350

Val Val Arg Ser Lys Gly Ser Val Asn Arg Ala Lys Ala Val Gly Asn
        355                 360                 365

Lys Asp Lys Asn Lys Gly Val Ser
```

-continued 370 375

(2) INFORMATION FOR SEQ ID NO: 103:

(i) SEQUENCE CHARACTERISTICS:
(A) LENGTH: 247 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 103:

CTGACCAGGA ACCCACTCTT CTGTGCATGT ATGTGAGCTG TGCAGAAGTA TGTGGCTGGG 60

AACTGTTGTT CTCTAAGGAT TATTGTAAAA TGTATATCGT GGCTTAGGGA GTGTGGTTAA 120

ATAGCATTTT AGAGAAGAAA AAAAAAAAAA AAAAAACTCG AGAGTACTTC TAGAGCGGCC 180

GCGGCGCCAT CGATTTTCCA CCCGGGTGGG GTACCAGGTA AGTGTACCCA ATTCGCCTAT 240

AGTGAGT 247

(2) INFORMATION FOR SEQ ID NO: 104:

(i) SEQUENCE CHARACTERISTICS:
(A) LENGTH: 363 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 104:

AGGACAAGCC AAGGACACTC TAAGTCTTTG GCCTTCCCTC TGACCAGGAA CCCACTCTTC 60

TGTGCATGTA TGTGAGCTGT GCAGAAGTAT GTGGCTGGGA ACTGTTGTTC TCTAAGGATT 120

ATTGTAAAAT GTATATCGTG GCTTAGGGAG TGTGGTTAAA TAGCATTTTA GAGAAGACAT 180

GGGAAGACTT AGTGTTTCTT CCCATCTGTA TTGTGGTTTT TACACTGTTC GTGGGGTGGA 240

CACGCTGTGT CTGAAGGGGA GGTGGGGGTC ACTGCTACTT AAGGTCCTAG GTTAACTGGG 300

GGAGATACCA CAGATGCTCA GCTTTCCACA TAACATGGGC ATGAACCAGC TAATCACACT 360

GAA 363

(2) INFORMATION FOR SEQ ID NO: 105:

(i) SEQUENCE CHARACTERISTICS:
(A) LENGTH: 524 base pairs
(B) TYPE: nucleic acid
(C) STRANDEDNESS: single
(D) TOPOLOGY: linear (ii) MOLECULE TYPE: cDNA -continued (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 105:

```
GGATCCTTCT CCTGGTCTCC TCGGAAGAAC GGGGCTTTCG CGTGACTGAG GAGAACACTC     60

AGGCCCTTGC CCTTGACCGT GTTCCTGGGG CAGTTTCCTA TTGGCTTGTA CGCCTTGTGT    120

TTTTTGTACA GCAAGATGGT AACCATGGTG ACAAGCACAG CCAGGCAGCC GATGGAGATC    180

AGGACACCAT TCACTGCTCT CAGAGGGAGT CTGGGTCTTT GCCAGGGATA GAGATCAGGG    240

TGCTGGTGAG GGCCAGGCTT CGATCATCTC CCAGAGTGAA ATTCACACAG TAGGTGCCAG    300

ACCCATTGAA GGCTCTTCTC ACAGACAGCA GCACAGCCCA TCCACAGCCA CAGGGCTGCA    360

GACCCGGTTC TGGGCGATCT GGCAGGTGGG GTCGGAGATG ATCGTACAGG CTTCCATGGG    420

GGTGGCCCCT TTGCAGGTCA CAGTGAAGTC CATCAGGGAG TTGGCAGGCT GCGGTGTGGG    480

CATGGGGACA TCTGCTATCT GCATGATGCT GACTTCCAGG ATCC                     524
```

(2) INFORMATION FOR SEQ ID NO: 106:

(i) SEQUENCE CHARACTERISTICS:
(A) LENGTH: 309 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 106:

```
TAGCAGATGT CCCCATGCCC ACACCGCAGC CTGCCAACTC CCTGATGGAC TTCACTGTGA     60

CCTGCAAAGG GGCCACCCCC ATGGAAGCCT GTACGATCAT CTCCGACCCC ACCTGCCAGA    120

TCGCCCAGAA CCGGGTCTGC AGCCCTGTGG CTGTGGATGG GCTGTGCTGC TGTCTGTGAG    180

AAGAGCCTTC AATGGGTCTG GCACCTACTG TGTGAATTTC ACTCTGGGAG ATGATCGAAG    240

CCTGGCCCTC ACCAGCACCC TGATCTCTAT CCCTGGCAAA GACCCAGACT CCCTCTGAGA    300

GCAGTGAAT                                                            309
```

(2) INFORMATION FOR SEQ ID NO: 107:

(i) SEQUENCE CHARACTERISTICS:
(A) LENGTH: 292 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

-continued (xi) SEQUENCE DESCRIPTION: SEQ ID NO: 107:

GGATCCTTCT CCTGGTCTCC TCGGAAGAAC GGGGCTTTCG CGTGACTGAG GAGAACACTC 60

AGGCCCTTGC CCTTGACCGT GTTCCTGGGG CAGTTTCCTA TTGGCTTGTA CGCCTTGTGT 120

TTTTTGTACA GCAAGATGGT AACCATGGTG ACAAGCACAG CCAGGCAGCC GATGGAGATC 180

AGGACACCAT TCACTGCTCT CAGAGGGAGT CTGGGTCTTT GCCAGGGATA GAGATCAGGG 240

TGCTGGTGAG GGCCAGGCTT CGATCATCTC CCAGAGTGAA ATTCACACAG TA 292

(2) INFORMATION FOR SEQ ID NO: 108:

(i) SEQUENCE CHARACTERISTICS:
(A) LENGTH: 263 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 108:

TTTTTTTTTT TTTTTTTTAG ACTGCCTTTT TAATGAGTAG AATATGTACA CACACGCACC 60

ATACACAAAG CCCGGGCCCA TTATAATTTT GTCAGGAGCT CAGGCATGCT CAGTGAGTTG 120

GAAGGCAGAT GAAGCATGCC TTCAGGTGGT GATTAGCTGG GTTCATGCCC ATGTTATCGT 180

GGAAAGCTGA GGCATCTGTG GTATCTCCCC CAGTTAACCT AGGACCTTAA GTAGCAGTGA 240

CCCACCTCCC TTCAGACACA GCG 263

(2) INFORMATION FOR SEQ ID NO: 109:

(i) SEQUENCE CHARACTERISTICS:
(A) LENGTH: 270 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 109:

GGATCCTGGA AGTCAGCATC ATGCAGATAG CAGATGTCCC CATGCCCACA CCGCAGCCTG 60

CCAACTCCCT GATGGACTTC ACTGTGACCT GCAAAGGGGC CACCCCCATG GAAGCCTGTA 120

CGATCATCTC CGACCCCACC TGCCAGATCG CCCAGAACCG GGTCTGCAGC CCTGTGGCTG 180

TGGATGGGCT GTGCTGCTGT CTGTGAGAAG AGCCTTCAAT GGGTCTGGCA CCTACTGTGT 240

GAATTTCACT CTGGGAGATG ATCGAAGCCT 270

(2) INFORMATION FOR SEQ ID NO: 110:

(i) SEQUENCE CHARACTERISTICS:

-continued (A) LENGTH: 239 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 110:

```
TTTTTTTTTT TTTTTTTTTC TTCTCTAAAA TGCTATTTAA CCACACTCCC TAAGCCACGA     60

TATACATTTT ACAATAATCC TTAGAGAACA ACAGTTCCCA GCCACATACT TCTGCACAGC    120

TCACATACAT GCACAGAAGA GTGGGTTCCT GGTCAGAGGG AAGGCCAAAG ACTTAGAGTG    180

TCCTTGGCTT GTCTGGAGCA ATGGATCCTT CTCCTGGTCT CCTCGGAAGA ACGGGCTTT     239
```

(2) INFORMATION FOR SEQ ID NO: 111:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 111:

```
AAACTGCAGT GCCCGGGCCA TGCCCTCCCC CTTCGCCTTC GACTCCGCCT CCACCTTCAA     60

CTCCGCCCTC ACCTCCGCCC TCACCTCTGC CCACATTATC AACACCTAGC CCCTCTTTAA    120

TGCCTACTGG TTACAAATCC ATGGAGCTGA GTGACATTTC CAATGAAAAC TGCCGAATAA    180

ACAGATATGG CTACTTCAGA GCCACCATCA CAATTGTAGA GGGGATCCTG GACGCAGCAT    240

CATGCAGATA GCAGATGTCC CATGCCCACA CCGCAGCCGT CCAACTCCTG ATGGACTTCA    300

CTGTGACCTC AAGGGCACCC ATGGAAGCTG TCAGA                               335
```

(2) INFORMATION FOR SEQ ID NO: 112:

(i) SEQUENCE CHARACTERISTICS:
(A) LENGTH: 217 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 112:

-continued

```
CCTCAACGAC TCTGCCATTT CCTACAAGTG GAACTTTGGG GACAACACTG GCCTGTTTGT     60

CTCCAACAAT CACACTTTGA ATCACACTTA TGTGCTCAAT GGAACCTTCA ACCTTAACCT    120

CACCGTGCAA ACTGCAGTGC CCGGGCCATG CCCTCCCCCT TCGCCTTCGA CTCCGCCTCC    180

ACCTTCAACT CCGCCCTCAC CTCCGCCCTC ACCTCTG                             217
```

(2) INFORMATION FOR SEQ ID NO: 113:

(i) SEQUENCE CHARACTERISTICS:
(A) LENGTH: 620 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 113:

```
CCTCAACGAC TCTGCCATTT CCTACAAGTG GAACTTTGGG GACAACACTG GCCTGTTTGT     60

CTCCAACAAT CACACTTTGA ATCACACTTA TGTGCTCAAT GGAACCTTCA ACCTTAACCT    120

CACCGTGCAA ACTGCAGTGC CCGGGCCATG CCCTCCCCCT TCGCCTTCGA CTCCGCCTCC    180

ACCTTCAACT CCGCCCTCAC CTCCGCCCTC ACCTCTGCCC ACATTATCAA CACCTAGCCC    240

CTCTTTAATG CCTACTGGTT ACAAATCCAT GGAGCTGAGT GACATTTCCA ATGAAAACTG    300

CCGAATAAAC AGATATGGCT ACTTCAGAGC CACCATCACA ATTGTAGAGG GGATCCTGGA    360

AGTCAGCATC ATGCAGATAG CAGATGTCCC CATGCCCACA CCGCAGCCTG CCAACTCCCT    420

GATGGACTTC ACTGTGACCT GCAAAGGGGC CACCCCCATG GAAGCCTGTA CGATCATCTC    480

CGACCCCACC TGCCAGATCG CCCAGAACCG GGTCTGCAGC CCTGTGGCTG TGGATGGGCT    540

GTGCTGCTGT CTGTGAGAAG AGCCTTCAAT GGGTCTGGCA CCTACTGTGT GAATTTCACT    600

CTGGGAGATG ATGCAAGCCT                                                620
```

(2) INFORMATION FOR SEQ ID NO: 114:

(i) SEQUENCE CHARACTERISTICS:
(A) LENGTH: 354 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 114:

```
GGATCCCCTC TACAATTGTG ATGGTGGCTC TGAAGTAGCC ATATCTGTTT ATTCGGCAGT     60

TTTCATTGGA AATGTCACTC AGCTCCATGG ATTTGTAACC AGTAGGCATT AAAGAGGGGC    120

TAGGTGTTGA TAATGTGGGC AGAGGTGAGG GCGGAGGTGA GGGCGGAGTT GAAGGTGGAG    180

GCGGAGTCGA AGGCGAAGGG GGAGGGCATG GCCCGGGCAC TGCAGTTTGC ACGGTGAGGT    240
```

-continued

TAAGGTTGAA GGTTCCATTG AGCACATAAG TGTGATTCAA AGTGTGATTG TTGGAGACAA 300

ACAGGCCAGT GTTGTCCCAA AGTTCCACTT GTAGGAATGG CAGAGTCGTT GAGG 354

(2) INFORMATION FOR SEQ ID NO: 115:

(i) SEQUENCE CHARACTERISTICS:
(A) LENGTH: 473 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 115:

CCTCAACGAC TCTGCCATTT CCTACAAGTG GAACTTTGGG GACAACACTG GCCTGTTTGT 60

CTCCAACAAT CACACTTTGA ATCACACTTA TGTGCTCAAT GGAACCTTCA ACCTTAACCT 120

CACCGTGCAA ACTGCAGTGC CCGGGCCATG CCCTCCCCCT TCGCCTTCGA CTCCGCCTCC 180

ACCTTCAACT CCGCCCTCAC CTCCGCCCTC ACCTCTGCCC ACATTATCAA CACCTAGCCC 240

CTCTTTAATG CCTACTGGTT ACAAATCCAT GGAGCTGAGT GACATTTCCA ATGAAAACTG 300

CCGAATAAAC AGATATGGCT ACTTCAGAGC CACCATCACA ATTGTAGAGG GGATCCTGGA 360

AGTCAGCATC ATGCAGATAG CAGATGTCCC CATGCCCACA CCGCAGCCTG CCAACTCCCT 420

GATGGACTTC ACTGTGACCT GCAAAGGGGC CACCCCCATG GAAGCCTGTA CGA 473

(2) INFORMATION FOR SEQ ID NO: 116:

(i) SEQUENCE CHARACTERISTICS:
(A) LENGTH: 223 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 116:

GAAGGTGGAG GCGGAGTCGA AGGCGAAGGG GGAGGGCATG GCCCGGGCAC TGCAGTTTGC 60

ACGGTGAGGT TAAGGTTGAA GGTTCCATTG AGCACATAAG TGTGATTCAA AGTGTGATTG 120

TTGGAGACAA ACAGGCCAGT GTTGTCCCCA AAGTTCCACT TGTAGGAAAT GGCAGAGTCG 180

TTGAGGAAGT GGCTGGGATC ATGAATGAGG ACATCGAAGA CGA 223

(2) INFORMATION FOR SEQ ID NO: 117:

(i) SEQUENCE CHARACTERISTICS:
(A) LENGTH: 247 base pairs
(B) TYPE: nucleic acid
(C) STRANDEDNESS: single
(D) TOPOLOGY: linear -continued (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 117:

GAATTCGCAC GAGGGGAGTC AGAGTCAAGC CCTGACTGGT TGCAGGCGCT CGGAGTCAGC 60

ATGGAAAGTC TCTGCGGGGT CCTGGGATTT CTGCTGCTGG CTGCAGGACT GCCTCTCCAG 120

GCTGCCAAGC GATTTCGTGA TGTGCTGGGC CATGAACAGT ATCCCGATCA CATGAGAGAG 180

CACAACCAAT TACGTGGCTG GTCTTCGGAT GAAAATGAAT GGGTTCCAAT ATCACTTTTG 240

TGGTGAA 247

(2) INFORMATION FOR SEQ ID NO: 118:

(i) SEQUENCE CHARACTERISTICS:
(A) LENGTH: 240 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 118:

GAATTCGGCA CGAGGAAGGA GGCCGTGTGC AGGCAGTCCT GACCAGTGAC TCACCGGCTC 60

TGGTGGGTTC CAATATCACT TTTGTGGTGA ACCTGGTGTT CCCCAGATGC CAGAAGGAAG 120

ATGCTAATGG CAATATCGTC TATGAGAAGA ACTGCAGGAA TGATTTGGGA CTGACATCTG 180

ACCTGCATGT CTACAACTGG ACTGCAGGGG CAGATGATGG TGACTGGGAA GATGGCACCT 240

(2) INFORMATION FOR SEQ ID NO: 119:

(i) SEQUENCE CHARACTERISTICS:
(A) LENGTH: 260 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 119:

GAAGGTGGAG GCGGAGTCGA AGGCGAAGGG GGAGGGCATG GCCCGGGCAC TGCAGTTTGC 60

ACGGTGAGGT TAAGGTTGAA GGTTCCATTG AGCACATAAG TGTGATTCAA AGTGTGATTG 120

TTGGAGACAA ACAGGCCAGT GTTGTCCCCA AAGTTCCACT TGTAGGAAAT GGCAGAGTCG 180

-continued

TTGAGGAAGT GGCTGGGATC ATGAATGAGG ACATCGAAGA CGATGGGGAG GTCTCTGAGG 240

AAGATCTCAT CAGACAAGTT 260

(2) INFORMATION FOR SEQ ID NO: 120:

(i) SEQUENCE CHARACTERISTICS:
(A) LENGTH: 231 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 120:

GAATTCGGCA CGAGGTCAAG CCCTGACTGG TTGCAGGCGC TCGGAGTCAG CATGGAAAGT 60

CTCTGCGGGG TCCTGGGATT TCTGCTGCTG GCTGCAGGAC TGCCTCTCCA GGCTGCCAAG 120

CGATTTCGTG ATGTGCTGGG CCATGAACAG TATCCCGATC ACATGAGAGA GCACAACCAA 180

TTACGTGGCT GGTCTTCGGA TGAAAATGAA TGGATGAACA CCTTGTATCC A 231

(2) INFORMATION FOR SEQ ID NO: 121:

(i) SEQUENCE CHARACTERISTICS:
(A) LENGTH: 286 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 121:

AAGGGGGAGG GCATGGCCCG GGCACTGCAG TTTGCACGGT GAGGTTAAGG TTGAAGGTTC 60

CATTGAGCAC ATAAGTGTGA TTCAAAGTGT GATTGTTGGA GACAAACAGG CCAGTGTTGT 120

CCCCAAAGTT CCACTTGTAG GAAATGGCAG AGTCGTTGAG GAAGTGGCTG GGATCATGAA 180

TGAGGACATC GAAGACGATG GGGAGGTCTC TGAGGAAGAT CTCATCAGAC AAGTTCCTGT 240

CATTCTTCTG GGACATGGTC ACGAATACAG GGATCTGATC TGTTAT 286

(2) INFORMATION FOR SEQ ID NO: 122:

(i) SEQUENCE CHARACTERISTICS:
(A) LENGTH: 224 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO -continued (v) FRAGMENT TYPE: <Unknown>

(vi) ORIGINAL SOURCE:

(xi) SEQUENCE DESCRIPTION: SEQ ID NO: 122:

GAATTCGGCA CGAGCCGACA CTGTGACTCC TGGTGGATGG GACTGGGGAG TCAGAGTCAA 60

GCCCTGACTG GTTGCAGGCG CTCGGAGTCA GCATGGAAAG TCTCTGCGGG GTCCTGGGAT 120

TTCTGCTGCT GGCTGCAGGA CTGCCTCTCC AGGCTGCCAA GCGATTTCGT GATGTGCTGG 180

GCCATGAACA GTATCCCGAT CACATGAGAG AGCACAACCA ATTA 224

(2) INFORMATION FOR SEQ ID NO: 123:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 123:

AAGGTGAAAG ATGTGTATGT GATAACAGAT CAGATCCCTG TATTCGTGAC CATGTCCCAG 60

AAGAATGACA GGAACTTGTC TGATGAGATC TTCCTCAGAG ACCTCCCCAT CGTCTTCGAT 120

GTCCTCATTC ATGATCCCAG CCACTTCCTC AACGACTCTG CCATTTCCTA CAAGTGGAAC 180

TTTGGGGACA ACACTGGCCT GTTTGTCTCC AACAATCACA CTTTGAATCA CACTTATGTG 240

CTCAATGGAA CCTTCAACCT TAACCTCACC GTGCAAACTG CAGTGCCCGG GCCATGCCCT 300

CCCCCTTCGC CTTCGACTCC GCCTCCACCT TCGTA 335

(2) INFORMATION FOR SEQ ID NO: 124:

(i) SEQUENCE CHARACTERISTICS:
(A) LENGTH: 266 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 124:

TACCATCGGA GAAAGAAGAC CAAGCAAGGC TCAGGCAGCC ACCGCCTGCT TCGCACTGAG 60

CCTCCTGACT CAGACTCAGA GTCCAGCACA GACGAAGAGG AATTTGGAGA ATTGGAAATC 120

GCTCTCGTTT TGTCAAGGGA GACTATCCCG ATGCTGCAAG ATCTGCTGTC CCTCTGGCCT 180

TTGTCATCCT CGCGCCTGCG TTGTGGCCTC TGTGGGCTTG GTGTGGAGCA AATGGCTCTC 240

AAGGAGGACT GAGTCTCAAG GAAATT 266

-continued (2) INFORMATION FOR SEQ ID NO: 125:

(i) SEQUENCE CHARACTERISTICS:
(A) LENGTH: 300 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 125:

AGCTAAGGTC AGGAGGTGTC TGAAGAATTG GCTGATGCAT GGCAGGGATG TTGTTGACCT 60

GCTTTTAGAA CAATACTTCC ATTTAATTAT AGCATATCTT ATGTGTGTAT TAAAGCAGAG 120

CCGATCTGGT GGGGCTCATT AAGTAAATGT ACTTACTGCA AAAGGTTCAA CTGGTGACCC 180

CAGTTTTCCC CAGAAGCAAT ATGATAGGAC AGAGGCGACT CCTGCAAGTT GTCTCAGACT 240

TCACACATAC ATTGTGACAT TCTCTGAGCA TGTGCACTGT ACATGATATG ACACTATCAA 300

(2) INFORMATION FOR SEQ ID NO: 126:

(i) SEQUENCE CHARACTERISTICS:
(A) LENGTH: 312 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 126:

AGCTAAGGTC CACTACCTTG TGAAGATGTA TAAACACCTG AAATGTAGAA GCGATCCGTA 60

TGTCAAGATC GAGGGGAAGG ACGCTGACGA CTGGCTGTGT GTGGACTTTG GGAGTATGGT 120

GATCCATTTG ATGCTTCCAG AAACCAGAGA AACCTATGAA TTAGAGAAAC TATGGACTCT 180

ACGTTCTTTT GATGACCTTA GCTAAGCCGA ATCAGCACAC TGGCGGCGTT ACTAGTGGAT 240

CGAGCTCGTA CAGCTGATGC ATAGCTTGAG TATCTATAGG TTACTAATAG CTGGCTATCA 300

TGTCAAGCGT TC 312

(2) INFORMATION FOR SEQ ID NO: 127:

(i) SEQUENCE CHARACTERISTICS:
(A) LENGTH: 281 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

-continued (vi) ORIGINAL SOURCE:

(xi) SEQUENCE DESCRIPTION: SEQ ID NO: 127:

GCTGAGCTGC AGAGAGTAGC ACATCCTTGC TAATTCAATA ACTACCAGTT TTTATTGGTG 60

AAACATGAAT CCAGATGGTA TGGTTGCTCT CCTGGACTAC CGTGAAGATG GTGTGACTCC 120

ATTCATGATT TTCTTTAAGG ATGGCTTAGA GATGGAGAAA TGTTAACAAA TTGGATCTAT 180

CACCTGTCAC CATAATTGGC TGCTGCTTAC CATCCATACA ACACCAGGAC TTAGGACAAA 240

TGGGACTGAT GTCATCTTGA GCTTTTATTT TGACCTTAGC T 281

(2) INFORMATION FOR SEQ ID NO: 128:

(i) SEQUENCE CHARACTERISTICS:
(A) LENGTH: 295 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 128:

AGCTAAGGTC AGAGCCAATA GTATCATGAG AACTGAAGAA GTAATAAAGC AACTTCTCCA 60

GAAATTTAAG ATTGAGAATA GCCCTCGGGA TTTCGCTCTT TACATTATTT TTGGGACAGG 120

AGAGCAGAGA AAGCTAAAGA AGACCGATGT CCACTGCTGC AGAGGTTACT ACAAGGACCA 180

TCCAAAAGCA ATGCTCGGAT CTCTCATGGA TAAAGATGCA GAAGAATCAC GAGAGATGTG 240

GCTCGTACAT TATTTCACTT TCTTCTGATC ATACTCAAGA TAGATGAGAG AGAAT 295

(2) INFORMATION FOR SEQ ID NO: 129:

(i) SEQUENCE CHARACTERISTICS:
(A) LENGTH: 240 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 129:

TTGACTTCTG AGTCTAACAC AGACACTGCA AGGGTTAATT TTCCAAGAGG TGGTTGTTGT 60

TGACGATAAA TTCATTAAGA ATTTTTAAAA ATTTAGTTAG ATTTACCAAA GTCACTGGAG 120

ACAAATTCAG AAGGCATATA TACCTGCCAG TTTTGTGGAC TACATTAATA GGGAGGCTTT 180

TATGTTTGAT GTAATTCTTA CAGTTCTAAG AATTAAGTTC CATTGCATGA GACCTTAGCT 240

(2) INFORMATION FOR SEQ ID NO: 130:

(i) SEQUENCE CHARACTERISTICS:

-continued (A) LENGTH: 196 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 130:

AAGGTGAATC CCCGACGGCT CTGGGCCCGA GGAGAAGCGT CGCCGTGGCA AATTGGCACT 60

GCAGGAGAAG CCCTCCACAG GTACTTGGAA AAACTGGTCT CTGAGGCCAA GGCCAGCTCC 120

GAGACATTCA GGACTTCTGG ATCAGCCTCC AGGGACACTG TGCAGTGAGA AGATGGCCAT 180

GAGTCCTGCC AGTGAG 196

(2) INFORMATION FOR SEQ ID NO: 131:

(i) SEQUENCE CHARACTERISTICS:
(A) LENGTH: 187 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 131:

AATTTTTTTT TTCGACGGCC CAACGGGGGC TTGGTGGATG GAAATATGGT TTTGTGAGTT 60

ATTGCACTAC CTGGAATATC TATGCCTCTT ATTTGCGTGT ACTGTTGCTG CTGATCGTTT 120

GGTGCTGTGT GAGTGAACCT ATGGCTTAGA AAAACGACTT TGTCTTAAAC TGAGTGGGTG 180

TTCAGGG 187

(2) INFORMATION FOR SEQ ID NO: 132:

(i) SEQUENCE CHARACTERISTICS:
(A) LENGTH: 197 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 132:

CACCTGATTT AAAGGAAAAG CATTCTGACG TAAGAAGCTG AAAGGCGGCC CTTGCGTGCT 60

TTGAACTTTC TTATACAGCA CAGTCATCTG AAGCTTCCTG TGTGACCAAG ACAAGAACGC 120

-continued

GTGCACAAGA CTGAGAAACA GCAAGAAACA ACCCGGCATT CTACTTTCTC AACACTATCA 180

TACTTTAAAC CTTTCAC 197

(2) INFORMATION FOR SEQ ID NO: 133:

(i) SEQUENCE CHARACTERISTICS:
(A) LENGTH: 200 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 133:

CTAGCTTACG CTAGTCCCCC ATGCATAAAG ACTGATCGCT TTTCCTTAGA AAGGTGAGAG 60

GGTTAGGACA AGGCCGTGTG GTAACAACAC CCGCAGCTCG AAAAACCAAT GGCTTGTTAA 120

CGTGTCAGTG AGGCACTGTA CGGACGTCCA TAGTCCACAT CTTCAAATTC CCGCAGAAGG 180

CTTCCTATTC TTAAACTCTA 200

(2) INFORMATION FOR SEQ ID NO: 134:

(i) SEQUENCE CHARACTERISTICS:
(A) LENGTH: 300 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 134:

CTACATTTCT GTATCCATTC CTCTGTTGAA GGCTCTGGTT CTTTCCAGCT TCTGGCTATT 60

ATAAATAAGG CTGCTATAAA CACAGTGGAG GCATGTGTCC TTGTTATATT TTGGAGCATC 120

TTTTGGGTAT ATGCCCAGAA GTGCTATAGC TGGTTCCTCA GGTAGTACTA TGTCGAATTT 180

TCTGAGGAAC TGCCAGACTG ATTTCCAGAG TGGTTGTACC AGCTTGCAAT CCCACCAGCA 240

ATAGAGGAGT GTTCCTCTTT CTCTATATTC TTGCCAACAT CTGCTGTCAC CTGAGTGTTT 300

(2) INFORMATION FOR SEQ ID NO: 135:

(i) SEQUENCE CHARACTERISTICS:
(A) LENGTH: 243 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO -continued (v) FRAGMENT TYPE: <Unknown>

(vi) ORIGINAL SOURCE:

(xi) SEQUENCE DESCRIPTION: SEQ ID NO: 135:

TGGTAAAGGG GGAATGATGT CGAGGCCATC CTGGGCTGTA GAGCCAGGCC CTGGCTTGGG 60

GAGTGGGCAT TGTTAACTTG TTGCTGACTT TGTGTTGACC CCTGCATCAG CAACTATTTC 120

CTTAAATCCA GGATACAACT TGTTAAGTGT GACAGCTTTC CTTTACACAC CATTTTTGTG 180

GGTGTATATA TATATTTGAC TTGGGGAGAA TTATTTTTTA CAAAAATACA AAATAGCTTT 240

TAA 243

(2) INFORMATION FOR SEQ ID NO: 136:

(i) SEQUENCE CHARACTERISTICS:
(A) LENGTH: 270 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 136:

AGCTAAGGTC CGGACTCTAT GGCATGACCC CAAAAACATT GGCTGGAAAG ATTACACTGC 60

CTACAGGTGG CACCTGATTC ACAGGCCTAA GACAGGCTAC ATGAGAGTCT TAGTGCATGA 120

AGGAAAGCAA GTCATGGCTG ACTCAGGACC AATTTATGAC CAAACCTACG CTGGTGGACG 180

GCTGGGCTGT TTGTCTTCTC CAAGAGATGG TCTATTCTCG GACCTCAAGT ATGAGTGCAG 240

AGATGCTAGA GAGCAGGCTC AGTCTCAGCA 270

(2) INFORMATION FOR SEQ ID NO: 137:

(i) SEQUENCE CHARACTERISTICS:
(A) LENGTH: 260 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 137:

TGACCTACGT GTAGTTGGTG TGCTTGTTGT CGAAGATGAG GGCCTCCTGG ATGAGCTGGT 60

GCTGCTGCTC CAGCAGGTCC AGGCTGGGCT TGTAGTCCAC GAGTCTGCGC TCGTACTGCT 120

TCAGGTGGCT CAGCTGGTCT TCCAGAGTCC CGTTCATCTC AATGGAGATG CGCCCGATCT 180

CCTCCATCTT AGTCTGGATC CACGGCCCCA CCATATTGGC TTGGCTGGCG AACTGTCGGC 240

GAAGGCTGCA TTGGATTGCT 260

-continued (2) INFORMATION FOR SEQ ID NO: 138:

(i) SEQUENCE CHARACTERISTICS:
(A) LENGTH: 187 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 138:

AATTTTTTTT TTCGACGGCC CAACGGGGGC TTGGTGGATG GAAATATGGT TTTGTGAGTT 60

ATTGCACTAC CTGGAATATC TATGCCTCTT ATTTGCGTGT ACTGTTGCTG CTGATCGTTT 120

GGTGCTGTGT GAGTGAACCT ATGGCTTAGA AAAACGACTT TGTCTTAAAC TGAGTGGGTG 180

TTCAGGG 187

(2) INFORMATION FOR SEQ ID NO: 139:

(i) SEQUENCE CHARACTERISTICS:
(A) LENGTH: 197 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 139:

CACCTGATTT AAAGGAAAAG CATTCTGACG TAAGAAGCTG AAAGGCGGCC CTTGCGTGCT 60

TTGAACTTTC TTATACAGCA CAGTCATCTG AAGCTTCCTG TGTGACCAAG ACAAGAACGC 120

GTGCACAAGA CTGAGAAACA GCAAGAAACA ACCCGGCATT CTACTTTCTC AACACTATCA 180

TACTTTAAAC CTTTCAC 197

(2) INFORMATION FOR SEQ ID NO: 140:

(i) SEQUENCE CHARACTERISTICS:
(A) LENGTH: 200 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 140:

CTAGCTTACG CTAGTCCCCC ATGCATAAAG ACTGATCGCT TTTCCTTAGA AAGGTGAGAG 60

-continued

GGTTAGGACA AGGCCGTGTG GTAACAACAC CCGCAGCTCG AAAAACCAAT GGCTTGTTAA 120

CGTGTCAGTG AGGCACTGTA CGGACGTCCA TAGTCCACAT CTTCAAATTC CCGCAGAAGG 180

CTTCCTATTC TTAAACTCTA 200

(2) INFORMATION FOR SEQ ID NO: 141:

(i) SEQUENCE CHARACTERISTICS:
(A) LENGTH: 300 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 141:

CTACATTTCT GTATCCATTC CTCTGTTGAA GGCTCTGGTT CTTTCCAGCT TCTGGCTATT 60

ATAAATAAGG CTGCTATAAA CACAGTGGAG GCATGTGTCC TTGTTATATT TTGGAGCATC 120

TTTTGGGTAT ATGCCCAGAA GTGCTATAGC TGGTTCCTCA GGTAGTACTA TGTCGAATTT 180

TCTGAGGAAC TGCCAGACTG ATTTCCAGAG TGGTTGTACC AGCTTGCAAT CCCACCAGCA 240

ATAGAGGAGT GTTCCTCTTT CTCTATATTC TTGCCAACAT CTGCTGTCAC CTGAGTGTTT 300

(2) INFORMATION FOR SEQ ID NO: 142:

(i) SEQUENCE CHARACTERISTICS:
(A) LENGTH: 243 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 142:

TGGTAAAGGG GGAATGATGT CGAGGCCATC CTGGGCTGTA GAGCCAGGCC CTGGCTTGGG 60

GAGTGGGCAT TGTTAACTTG TTGCTGACTT TGTGTTGACC CCTGCATCAG CAACTATTTC 120

CTTAAATCCA GGATACAACT TGTTAAGTGT GACAGCTTTC CTTTACACAC CATTTTTGTG 180

GGTGTATATA TATATTTGAC TTGGGGAGAA TTATTTTTTA CAAAAATACA AAATAGCTTT 240

TAA 243

(2) INFORMATION FOR SEQ ID NO: 143:

(i) SEQUENCE CHARACTERISTICS:
(A) LENGTH: 270 base pairs
(B) TYPE: nucleic acid
(C) STRANDEDNESS: single
(D) TOPOLOGY: linear (ii) MOLECULE TYPE: cDNA -continued (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 143:

AGCTAAGGTC CGGACTCTAT GGCATGACCC CAAAAACATT GGCTGGAAAG ATTACACTGC 60

CTACAGGTGG CACCTGATTC ACAGGCCTAA GACAGGCTAC ATGAGAGTCT TAGTGCATGA 120

AGGAAAGCAA GTCATGGCTG ACTCAGGACC AATTTATGAC CAAACCTACG CTGGTGGACG 180

GCTGGGCTGT TTGTCTTCTC CAAGAGATGG TCTATTCTCG GACCTCAAGT ATGAGTGCAG 240

AGATGCTAGA GAGCAGGCTC AGTCTCAGCA 270

(2) INFORMATION FOR SEQ ID NO: 144:

(i) SEQUENCE CHARACTERISTICS:
(A) LENGTH: 260 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 144:

TGACCTACGT GTAGTTGGTG TGCTTGTTGT CGAAGATGAG GGCCTCCTGG ATGAGCTGGT 60

GCTGCTGCTC CAGCAGGTCC AGGCTGGGCT TGTAGTCCAC GAGTCTGCGC TCGTACTGCT 120

TCAGGTGGCT CAGCTGGTCT TCCAGAGTCC CGTTCATCTC AATGGAGATG CGCCCGATCT 180

CCTCCATCTT AGTCTGGATC CACGGCCCCA CCATATTGGC TTGGCTGGCG AACTGTCGGC 240

GAAGGCTGCA TTGGATTGCT 260

(2) INFORMATION FOR SEQ ID NO: 145:

(i) SEQUENCE CHARACTERISTICS:
(A) LENGTH: 255 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 145:

TGACCATCGA TAAGTTTAAT AACTACAGAC TTTTCCCAAG ACTACAAAAG CTTCTTGAAA 60

GTGACTACTT TAGATATTAC AAGGTGAACT TGAAGAAGCC TTGTCCTTTC TGGAATGACA 120

TCAACCAGTG TGGAAGAAGA GACTGTGCCG TCAAACCCTG CCATTCTGAT GAAGTTCCTG 180

-continued

ATGGAATTAA GTCTGCCGAG CTACAAGTAT TCTGAGGAAG CCCAACCGCA TTGAAGAATG 240

TGAGCAAGCT GAGCG 255

(2) INFORMATION FOR SEQ ID NO: 146:

(i) SEQUENCE CHARACTERISTICS:
(A) LENGTH: 236 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 146:

AACTCTGTGA ACCGTGCCTT TCTCTGTGGA GGTGGAGGTG TCGGTTGAAG ACAAGCGAGG 60

TCCTCCAAGG GGCTGTGTCT TATGTTGCCA TCTCCCCTTG TAGCTTGGCT GCCCACCCTC 120

CAGACTGTGC GCCATGGCTC CAAGGCTGTG ACCCGCCACT GGAGTCATGC ACTTCCAGCG 180

GCAGAAGCTG ATGCTATAAC TGAGTATATT CCTCCAAACC TGCCATCAAC CCGAGA 236

(2) INFORMATION FOR SEQ ID NO: 147:

(i) SEQUENCE CHARACTERISTICS:
(A) LENGTH: 291 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 147:

ACTTCTCCAG AGAATTTAAG ATTGAGAATA GCCCTCGGGA TTTCGCTCTT TACATTATTT 60

TTGGGACAGG AGAGCAGAGA AAGCTAAAGA AGACCGATGT CCCACTGCTG CAGAGGTTAC 120

TACAAGGACC ATCCAAAAGC AATGCTCGGA TCTTCCTCAT GGATAAAGAT GCAGAAGAAA 180

TCAGCAGAGA TGTGGCTCCG TACATTAATT TCACTTTTCT TTCTTGGATC CATCCTTCAA 240

GATTAGATGA AGAAGAGAAA TGGAGATTGA GAGAATATGC AATCATACCG A 291

(2) INFORMATION FOR SEQ ID NO: 148:

(i) SEQUENCE CHARACTERISTICS:
(A) LENGTH: 255 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO -continued (v) FRAGMENT TYPE: <Unknown>

(vi) ORIGINAL SOURCE:

(xi) SEQUENCE DESCRIPTION: SEQ ID NO: 148:

AGGGTTACTT CAGGCTAAGG CAATAGAAAT CCATTTTAAG ATGGTGTGCT AAAGGCTTGA 60

TGGATGTTCA TCGTCTGTCT AAAGGAGAAT GAAGTCATCA ACAGGATGTC AGGGGAAAGT 120

GAGATCATCG CAGAAAGTAT CAACTTAGCA CAAACACACA GGCATAGCTC CTGCAAGAGG 180

TGAATGCTGT CCCCAAATAC CTGAGGAACT ATCCCTTTGG GCAAGAAAAT AGACAAGTCC 240

ATGAAGTCTG GGTGA 255

(2) INFORMATION FOR SEQ ID NO: 149:

(i) SEQUENCE CHARACTERISTICS:
(A) LENGTH: 284 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 149:

GACCAGGTAC ACTTGAGCAA AGCACCCAGT ATTTAATTCC TTACAGAAAG GAGAGGAAAG 60

GTCTGCAGTT GGACTGATGG TATGCTAACA CCGCAAATGA CTGTCATTTG ATCTCAGAAG 120

TTCAGGATTG ATTGCTATGT TTTAGCTCTA ATTGTGAGAA ACAGTAGTCA TTTTAGTCTT 180

AAATTTTGCC CTCAGGAAAT TCAGGGAGAC TGAGCCTTCC TTCCCCCACC TTCGTAAAGC 240

CGAATTCCAG CACACGGCGG CCGTTACTAG TGGATCCGAG CTCG 284

(2) INFORMATION FOR SEQ ID NO: 150:

(i) SEQUENCE CHARACTERISTICS:
(A) LENGTH: 335 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 150:

TACAAGGTGG GATGGCAGGA ACTGAAGGCT TCTGTAAATC CAGTTTTGGC TCTCTCTCTG 60

GTCTTTCTTT CTCTTCTGTT CTGTTTGGAA GGGTTTCTGG TCTTTCAGGA GGTATTTTTT 120

TAATTTCATG TTTTCTCTCT GTGGTACCTG CCCCTTGTTT GACGACAGGA GCTGATGGAG 180

GTGGCGGTTT CTTGGGTCTA TTCCCTTCCT TGTCAAAGTC CGATGGAAGT AACTTCACGA 240

AGTTGTCAGG AAACACGCCT CGTCTGCCAT TGAGTTCTCC TTCCCACCAG CCTACGCGAT 300

GCAGTCTTAT TGATGAGAGT CACTATATCT CCTTA 335

-continued (2) INFORMATION FOR SEQ ID NO: 151:

(i) SEQUENCE CHARACTERISTICS:
(A) LENGTH: 254 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 151:

TCACCCATGA CTTCTATGGA CTTGTCTATT TTCTTGCCCA AAGGGATAGT TCCTCAGGTA 60

TTTGGGGACA GCATTCACCT CTTGCAGGAG CTATGCCTGT GTGTTTGTGC TAAGTTGATA 120

CTTTCTGCGA TGATCTCACT TTCCCCTGAC ATCCTGTTGA TGACTTCATT CTCCTTTAGA 180

CAGACGATGA ACATCCATCA GGCCTTTATG CACACCATCT TAAAATGGAT TTCTATTGCC 240

TTAGCCTGAA GTCC 254

(2) INFORMATION FOR SEQ ID NO: 152:

(i) SEQUENCE CHARACTERISTICS:
(A) LENGTH: 241 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 152:

CCCATAGAGA TAGGTTTGCT CCAGAACCTG CAGCATTTGC ACATCACAGG GAACAAGGTG 60

GACATTCTGC CAAAACAGTT GTTTAAGTGC GTGAAGTTGA GGACTTTGAA CCTGGGGCAG 120

AACTGTATCG CCTCCCTGCC TGAGAAAATC AGTCAGCTCA CCCAGCTCAC TCAGCTGGAG 180

CTGAAGGGCA ACTGCCTAGA CCGCCTGCCA GCCCAGCTGG CAGTGTCGAT GCTCAAGAAG 240

A 241

(2) INFORMATION FOR SEQ ID NO: 153:

(i) SEQUENCE CHARACTERISTICS:
(A) LENGTH: 256 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

-continued (vi) ORIGINAL SOURCE:

(xi) SEQUENCE DESCRIPTION: SEQ ID NO: 153:

CAATAATCCA GGTAAAATAG AGTAAAATAG TCTGCTAGCA GCAAGTTCCT ACCATACTTT 60

CAACAACACT CACGAGATAC GGAATGATTA CAGCATTAAG AATATTTCAG AAATGACAGG 120

TAGGTGTGGT GGACAGGTGG CTCACATTCA AGACTCAAGT CTACTTAAAA AAGAAAATCT 180

CACTAGCACT AGATTCTAGC TCCTTTGTTT CCCCCTTTCT TTTGGTTTCA AAGGCGTTTC 240

TACAACCCAT AAGAGG 256

(2) INFORMATION FOR SEQ ID NO: 154:

(i) SEQUENCE CHARACTERISTICS:
(A) LENGTH: 404 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 154:

GCCAAGCTAT TATGACACTA TAGATACTCA ACGTATCGAT CAACGTTGGT ACCGAGCTCG 60

GATCCACTAG TAACGGCCGC CAGTGTGCTG GAATTCGGCT TGGATTGGTC AGAGCAGTGT 120

GCAATATGAT CCAACTAAGT CTCCTCCCTT GGCCCCTCCC CAAAATGTTT GCAGTGTTAT 180

TTTTGTGGGT TTTTTTTTAA CACCCTGACA CCTGTTGTGG ACATTGTCAA CCTTTGTAAG 240

AAAACCCAAA TAAAAATTGA AAAATAAAAT AAAAAGAAAC CCATGAACAT TCGCACCACT 300

TGTGGCTTCT GACTATCTTC CACAGAGGGA AGTTTAAAAC CCAAACTTCC AAAGGTTTGA 360

ACTACCTCAA GACACTTTCG CAGTGGAGTC GTAGACCAAT CCCA 404

(2) INFORMATION FOR SEQ ID NO: 155:

(i) SEQUENCE CHARACTERISTICS:
(A) LENGTH: 167 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 155:

TAAATAAATT AAAAAACTAT TAAACCTAAA AACGTCCACC AAACCCTAAA ACCATTAAAC 60

AACCAACAAA CCCACTAACA ATTAAACCTA AACCTCCATA AATAGGTGAA GGCTTTAATG 120

CTAACCCAAG ACAACCAACC AAAAATAATG AACTTAAAAC AAAAATA 167

(2) INFORMATION FOR SEQ ID NO: 156:

-continued (i) SEQUENCE CHARACTERISTICS:
(A) LENGTH: 212 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 156:

GGTAAAGGGG ACCTGGAGAA CGCCTTCCTG AACCTGGTCC AGTGCATCCA GAACAAGCCC 60

CTGTACTTCG CTGACCGGCT GTACGACTCC ATGAAGGGCA AGGGGACTCG AGACAAGGTC 120

TGATTAGAAT CATGGTCTCT CGCAGTGAAG TGGACATGCT GAAAATCAGA TCTGAATTCA 180

AGAGGAATAT GGCAAGTCCT GTACTACTAC AT 212

(2) INFORMATION FOR SEQ ID NO: 157:

(i) SEQUENCE CHARACTERISTICS:
(A) LENGTH: 214 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 157:

AGAGCAGCAG GCCAGCTGTA CTTGGTTTGG CAAGAAAAAG AAGCAGTACA AAGATAAATA 60

TTTGGCAAAG CACAACGCAG TGTTTGATCA ATTAGATCTT GTCACATATG AAGAAGTAGT 120

CAAACTGCCA GCATTCAAAA GGAAAACATT AGTCTTATTA GGTGCACATG GTGTTGGAAG 180

AAGACACATA AAAAATACCC TCATCACAAA GCAC 214

(2) INFORMATION FOR SEQ ID NO: 158:

(i) SEQUENCE CHARACTERISTICS:
(A) LENGTH: 342 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 158:

TCGGTCATAG TAGTAAGGGA AATCTCCCAG GTAAGATGAA TACTGCGGTA GGACGAACAA 60

-continued

```
TCCTCCAGGA TGTTTGTTCC ATATTAAACT GTTACGTGAT ATGTGCTTGA ATATTCTGTC    120

CTGAATAATC TCTAGTGTAG TTAATACAAT CTTCTCAACT GAAGAAAAAT AAGCCTCCCA    180

CAAGAACTGT GTCTGCTGTC TAAGTGCTAG GATTTTATCC TGATGAATAG ACCTGATTGT    240

AGAAGGAATC TGTAATAGCA ATCTCTCATC GCCTATGACC GAAAGCCGAA TTCTGCAGAT    300

ATCCATCACA CTGGCCGGCC GCTCGAGCAT CGATCTAGAG GG                       342
```

(2) INFORMATION FOR SEQ ID NO: 159:

(i) SEQUENCE CHARACTERISTICS:
(A) LENGTH: 303 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 159:

```
CTGCTTGATG ACAAAGGGTG TAGTCTTCAT CTTTTCCTGG ATTATTTTGG AAGTGACAGG     60

TGGAAATTCC ATCGTCACGT TTATGTGGTC TGTAAAGCCA ACGATCTCAA ATTCTGGCGG    120

CTCAAGAGGA GCGTTTGCAG GCACGATGTA GTCTGAGCAG CGGCACACGG TCAAGTCCCC    180

TCTGTGCACT ATGACGATGG CGACGACGTA GCTCTCCATG CCCTCCAACC ACTTATCTGT    240

CACGTCACAT GATGACTTCG TGGTATCTGA ACAGTTCTTA ACCTTCGTCA GATTTTCGTC    300

TTT                                                                  303
```

(2) INFORMATION FOR SEQ ID NO: 160:

(i) SEQUENCE CHARACTERISTICS:
(A) LENGTH: 345 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 160:

```
AAATCGTTGC TTCAGAAAGA CTCAATAACA CTTACTTGTG CCTGGCTGTG CTGACAGTAC     60

ATTCTGTGTC ATTTTCCTTC ATGGGCGGAA CAGTCCACAG AGCTCACCAA CAAGTACTCC    120

AAAACTGAGC AAGAGTTTAA GCTTCGAGAT GCAACCAGAT GAGCTTCTAG AAAAGCCCAT    180

GTCTCCCATG CAGTACGCAC GGTCTGGACT AGGGACAGCA GAGATGAATG GCAAACTCAT    240

AGCTGCAGGT GGTTATAACA GAGAGGAATG TCTTCGAACA GTTGAATGCT ATGATCCACA    300

TACAGATCAC TGGTCCTTCC TTGCTCCCAT GAGAACATCA AGCAG                    345
```

(2) INFORMATION FOR SEQ ID NO: 161:

-continued (i) SEQUENCE CHARACTERISTICS:
(A) LENGTH: 315 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 161:

```
CTTTCCGAAG AGCACACCCT CCTCTCAATG AGCTTGTGAG GTCTCTTTCT TCTCTTCCTT     60

CCAACGTGGT GCTAGCTCCA GGCGAGCGAC GTGAGAGTGC CACCTGAGAC AGACACCTTG    120

GTCTCAGTTA GAAGGAAGAT GCAGGTCTAA GAGGAATCCC CGCAGGTCTG TCTGAGCTGT    180

GATCAAGAAT ATTCCGCAAT GTGCCTTTTC TGAGATCGTG TTAGCTCCAA AGCTTTTTCC    240

TATCGCAGAG TGTTCAGTTT GTGTTTGTTT GTTTTTGTTT TGTTTTGTTT TTCCCTTGGC    300

GGATTTCCCG TGTGT                                                     315
```

(2) INFORMATION FOR SEQ ID NO: 162:

(i) SEQUENCE CHARACTERISTICS:
(A) LENGTH: 243 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 162:

```
CCTATTGAAC GGTCTTGCAA TGACGAGCAT TCAGATGCTT AAGGAAAGCA TTGCTGCTAC     60

AAATATTTCT ATTTTTAGAA AGGGTTTTTA TGGACCAATG CCCCAGTTGT CAGTCAAAGC    120

CGTTGGTGTT TTCATTGTTT AAAATGTCAC CTATAAAACG GGCATTATTT ATGTTTTTTT    180

TCCCTTTGTT CATATTCTTT TGCATTCCTG ATTATTGTAT GTATCGTGTA AAGGAAGTCT    240

GTA                                                                  243
```

(2) INFORMATION FOR SEQ ID NO: 163:

(i) SEQUENCE CHARACTERISTICS:
(A) LENGTH: 243 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

-continued (xi) SEQUENCE DESCRIPTION: SEQ ID NO: 163:

CCTATTGAAC GGTCTTGCAA TGACGAGCAT TCAGATGCTT AAGGAAAGCA TTGCTGCTAC 60

AAATATTTCT ATTTTTAGAA AGGGTTTTTA TGGACCAATG CCCCAGTTGT CAGTCAAAGC 120

CGTTGGTGTT TTCATTGTTT AAAATGTCAC CTATAAAACG GGCATTATTT ATGTTTTTTT 180

TCCCTTTGTT CATATTCTTT TGCATTCCTG ATTATTGTAT GTATCGTGTA AAGGAAGTCT 240

GTA 243

(2) INFORMATION FOR SEQ ID NO: 164:

(i) SEQUENCE CHARACTERISTICS:
(A) LENGTH: 266 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 164:

CCTGGGTCCG TCCTCCAACC CCTCACGCCC AAACCCTCCG ACTTTCACTT CTTGAAGTGA 60

TCGGAAAGGG CAGTTTTGGA AAGGTTCTTC TGGCTAGGCA CAAGGCAGAA GAAGTATTCT 120

ATGCAGTCAA AGTTTTACAG AAGAAGCCAT CCTGAAGAAG AAAGGAAGGA AGCATATTAT 180

GTCAGAGCGG AATGTTCTGT TGAAGAATGT GAAGCACCCT TTCCTGGTGG GCCTTCACTT 240

CTCATTCCAG ACCGCTGACA AGCTCT 266

(2) INFORMATION FOR SEQ ID NO: 165:

(i) SEQUENCE CHARACTERISTICS:
(A) LENGTH: 204 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 165:

GATGCTGAAC ACAAAAAGAA AGAAGAAAAG GAAGAGGAGG AGCAAGAGAA GCTGAAGGGA 60

GGGAGCCTTG GCGAAAATCA GATCAAAGAT GAGAAGATTA AAAAGGACAA AGAGCCCAAA 120

GAAGAGTCAA GAGCTTCTTG GATAGAAAGA AAGGATTTAC AGAGTGAGGC GCAGAATGGA 180

GATTCATGAC CCACAAACTT AAAC 204

(2) INFORMATION FOR SEQ ID NO: 166:

(i) SEQUENCE CHARACTERISTICS:
(A) LENGTH: 200 base pairs
(B) TYPE: nucleic acid

-continued (C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 166:

AAAGCCAATT GGTAGAGAAA TTGAAGACAC AAATGCTGGA TCAGGAAGAG CTTCTGGCAT 60

CAACCAGAAG GGATCAAGAT AATATGCAAG CTGAACTGAA TCGCCTCCAA GCAGAAAATG 120

ATGCTTCTAA AGAAGAGTAA AGAGTTTTAC AGGCCTTAGA GGACTGCTGT TAATTATGAT 180

CAGAGTTCAG GAGTTAAGAC 200

(2) INFORMATION FOR SEQ ID NO: 167:

(i) SEQUENCE CHARACTERISTICS:
(A) LENGTH: 337 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 167:

CTGCTTGATG TCCTGTGTAG CGAATGTCAC AGCGTACAAC ATTGTTAGTG TAGTCTGATT 60

CAGGCACCAG GTAGCTGGGG TTTACACTGA CCTTTAGAAT GTAGTTTCCA GGTTGTACAT 120

CTGTAATATC AATCCACTGG CAGTCTATGT CTGCCGCATA GGTGTCATAA CATCCAGGAC 180

TCAATCCCTG TGTGTGTGCA GTGCACGCAA AGGCCCTGTG GTACCCATAG TCACAGGACG 240

TGTCCTCCAG ACAGAAGCTT GCTTTGTGGC CTTCAGCCAC TCTCCTCTGT GTGTTGGCAT 300

CAACGAGAAG CCGAATTCTC GAGATATCCA TCACACT 337

(2) INFORMATION FOR SEQ ID NO: 168:

(i) SEQUENCE CHARACTERISTICS:
(A) LENGTH: 337 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 168:

CTGCTTGATG TCCTGTGTAG CGAATGTCAC AGCGTACAAC ATTGTTAGTG TAGTCTGATT 60

-continued

```
CAGGCACCAG GTAGCTGGGG TTTACACTGA CCTTTAGAAT GTAGTTTCCA GGTTGTACAT    120

CTGTAATATC AATCCACTGG CAGTCTATGT CTGCCGCATA GGTGTCATAA CATCCAGGAC    180

TCAATCCCTG TGTGTGTGCA GTGCACGCAA AGGCCCTGTG GTACCCATAG TCACAGGACG    240

TGTCCTCCAG ACAGAAGCTT GCTTTGTGGC CTTCAGCCAC TCTCCTCTGT GTGTTGGCAT    300

CAACGAGAAG CCGAATTCTC GAGATATCCA TCACACT                             337
```

(2) INFORMATION FOR SEQ ID NO: 169:

(i) SEQUENCE CHARACTERISTICS:
(A) LENGTH: 374 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 169:

```
GATCTGACAC TACAGCATGA GCGTTAGATT TCATAAAATT ATTTTTCTTC TAAATGCTGG     60

AAACTCTAAG GGTTTATTCA GAAAAAAAAC TGGCCAATTT TCAAATGGCT TAGAAGCAGG    120

GTTAATTAAG TATTGAATGA GCCACTGTGA TATCCTGATG ACACCCAGTC ACAATGACAG    180

TTTTGAAGCA TACAACCAAA ACAATTGAGA TCTCAAAACT ATTTTACATC ACTTATGGTA    240

ATGTTATGTA AAAATGAAAA TGCTTTCTGT GGAAGTTACA TTCTTTACCA GGTCTTTAAC    300

ATAAATTAAC ACGACGTCGA GTAAGCCTTT GTTCGGAAGA CAAACTAGTT TGTGAGTTCA    360

GTCAGATCCC AGCT                                                      374
```

(2) INFORMATION FOR SEQ ID NO: 170:

(i) SEQUENCE CHARACTERISTICS:
(A) LENGTH: 334 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 170:

```
AGTTGCCAGG ACCACCACCA TAGTTGCCAG GTTCATCATA AACAAATCCA ACATCAATCT     60

TAAATTCCCC CATCAGACAA TCTGCCCTCA AAGAATGGGA ATTATAAACC CGGATACTGA    120

TGATCTCATC CATGAGCTCA GAGGGTGTGA TGTGCACATT GTAGAAAAAT AACTCGTCAA    180

AAAACGGATT GTTCCCTCTC TTGATTCTCG TGCGATGCGT CTGACCACAG ATGTGAACTT    240

TCACCACGGG CCTTATGTTG TTGCCGCATA ACTGACGGCC CTCGATCACT CTGACACGGA    300

TCTGGAAATC TGTGGCTTGT TGGACAGCAT CCTT                                334
```

-continued (2) INFORMATION FOR SEQ ID NO: 171:

(i) SEQUENCE CHARACTERISTICS:
(A) LENGTH: 380 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 171:

AAGCCGTGTC CCAAAGAATG GATAGAGACG CGATCAGATG CGACAGTGCT GTGGAGAAAG 60

CCCAGGAACC TGCACAATTG CCCTGGTCCA ATGGCTCGTG GATCAGGTTG GGCCACTTCT 120

CTGAAGCTTC AAAGGCAGTG GGTAGCACTT CCCCTTGGCC CAGCACCGTA TAAATCTCAT 180

TCATATTCAT GACAGTGGAG GATGGGCGGA TTGTGCCCAG GCGGTACGGA ATGCCCTCAT 240

CCAGGGTCAT GCCCCAGAAG GCACTGTGGT TCCCAGCCTG CCACCCGTAG TTGCCTCGGT 300

TGATGGCTTT AATCATGTCT GGTCACTAGA CACGGCTTAA GCGAATCTCG AGATATCCAT 360

CACACTGGCG GCGTCGAGAT 380

(2) INFORMATION FOR SEQ ID NO: 172:

(i) SEQUENCE CHARACTERISTICS:
(A) LENGTH: 353 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 172:

AAGCCGTGTC TGATGATGGA GGTAGTGGTG GGGGAGGAGG GACTGAGGGT CCTGAGGTGG 60

TGGCCCCTGG AACTGATCCC ACATAGTTAC CCACTGCTAG TTCTGACCCC GTGGACAACG 120

TGCCAGAGGC CATGACTGGC AGTATGGCAA TGTCCCCATC CCCTTTCTTC TTAATTTTAA 180

TGGTCCCTTG TTTCTCCAGT TCGTGAATCT TTTTTTCCAG GGTAGACTGT CTTTGAATGG 240

CTTCTTCCTT TTCTTTGACC ATTTTTCTTA ACGTGTGAAC TTGGGTATTT GCATCTTTGT 300

AGATTTCCGG ACAACATCAG TTCCTTATTC CTCTGCATAA GTTGCTTTCA GTT 353

(2) INFORMATION FOR SEQ ID NO: 173:

(i) SEQUENCE CHARACTERISTICS:
(A) LENGTH: 350 base pairs
(B) TYPE: nucleic acid
(C) STRANDEDNESS: single
(D) TOPOLOGY: linear (ii) MOLECULE TYPE: cDNA (iii) HYPOTHETICAL: NO -continued (iv) ANTI-SENSE: NO (v) FRAGMENT TYPE: <Unknown>

(vi) ORIGINAL SOURCE:

(xi) SEQUENCE DESCRIPTION: SEQ ID NO: 173:

CGAGTCAGAC ACATGAAAGC AAAACGCGGG CAGATAAAAC GATCGCCTTA CCTTCTAGCA 60

AAAATCTGAA GCTTGTGTCA GAAACAAAGA CTCAGAAAGG TTTGTTTTCA GATGAAGAAG 120

ACTCTGAGGA TTTGTTTTCT TCTCAAAGTT CAAGTAAGCC AAAAAGTGCA TCACTTTCAT 180

CCAGCCAGCC CCCAACATCA GTCTCCCTTT TTGGTGATGA AGATGAAGAG GACAGTCTTT 240

TTGGGAGTGC AGCAGCTAAG AAGCAGACTT CATCTCTACA ACCTCAGAGT CAAGAGAAAG 300

CAAAGCCTTC CGAGCAGCCC TCAAAGAAGA CATCTGCCTT GTTGTTCAGA 350

(2) INFORMATION FOR SEQ ID NO: 174:

(i) SEQUENCE CHARACTERISTICS:
(A) LENGTH: 377 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 174:

CGAGTCAGAC TTAATTTAAA AACGAAACAA AACAAAAATA ACATAGTTTA GAAATCAAGG 60

AGAAAGGACA GATAGTCTAA GAAAAAAGAC AACACAAAAG AGGGGCAGGG CGGCCAGCTT 120

GCATCAGGGA TCTTGGCTGG AGACCTGCTT TGAATAGGTT TCTTGCAGGT ATTTCTTAAA 180

TGCTGTGGGG TTTTTCCAGA GTTCCGCAGC GTGTGTGTTC AAAGGGCTAT CGATGTTGGG 240

TTCTCCTAGC AGGCTCTGGA TAGAGAGCAA GATAGTCCTG ACATCATATA GTGCAGACCA 300

CTTATCCTTG AGGATGTCCG GCAGATGTTG CCTGGGTGTC ACGTTGGGGT GGTAGCAGGG 360

TGTGAGGAAC TTCACTG 377

(2) INFORMATION FOR SEQ ID NO: 175:

(i) SEQUENCE CHARACTERISTICS:
(A) LENGTH: 326 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (v) FRAGMENT TYPE: <Unknown>

(vi) ORIGINAL SOURCE:

(xi) SEQUENCE DESCRIPTION: SEQ ID NO: 175:

CGAGTCAGAC ACTCCTGGCT CCTGGATTCT TTAGATGCCT CCATCAGACT GGGTACTTTA 60

-continued

```
GATGCCTCCA TCAGACTACT TCGTCATTGT ATTTCTCAGT TCGCTCAGGG CAAGCGGCAG    120

TCTCTGGGCT GCTGTGGCAG GTGCCACCAC TGCATTTAAA AGTTAAAATT TCTTCAAATA    180

TTCCCATCAA GGCCTTGTAG CCTCTGAGAT TGGTTTACTA TTTGCCCAGT TATTTAAAGC    240

TCTCTGCATT CCTTCCTGAT TTAATATTGC TATGGCCAGG ACAATGTGTA GAAGTAAAAA    300

GGATATCATA TTTACAGGTG TAACGC                                         326
```

I claim:

[1. A method for identifying a sequence expressed in a metastasis comprising the steps of:

a) transfecting an oncogenic sequence into a mammalian cell to form a population of transfected cells;

b) administering tranfected cells to a primary site of a host mammal to form a primary tumor;

c) maintaining said mammal for a period of time sufficient to develop a metastasis at a secondary site;

d) amplifying expressed RNA sequences of the transfected cells and expressed RNA sequences of the metastasis by differential-display PCR; and e) comparing the amplified expressed RNA sequences of the transfected cells with the amplified expressed RNA sequences of the metastasis and identifying the sequence expressed at a higher level in the metastasis as compared to the expressed RNA sequences of the transfected cells.]

[2. The method of claim 1 wherein the mammalian cell is transfected by calcium phosphate transfection, viral transduction, lipofection, dextran sulfate transfection or electroporation.]

[3. The method of claim 1 wherein the oncogenic sequence is a sequence of the gene that erodes the oncoproteins p21, p34, p53, myc, ras or src.]

[4. The method of claim 1 wherein the oncogenic sequence is a sequence that enhances metastatic potential.]

[5. The method of claim 4 wherein the oncogenic sequence is a sequence of the gene that encodes cyclin D1, caveolin or TGF-β1.]

[6. The method of claim 1 wherein the mammalian cell is treated with an agent that alters gene expression prior to the administration of said cell to said host mammal.]

[7. The method of claim 6 wherein the agent is benzanthracene (BA), dimethyl benzanthracene (DMBA) or 5-azacytidine.]

[8. The method of claim 1 wherein the mammalian cell is a primary cell or an established cell line.]

[9. The method of claim 1 wherein the mammalian cell is isolate from urogenital sinus tissue.]

[10. The method of claim 1 wherein the mammalian cell is a fetal cell.]

[11. The method of claim 1 wherein the mammalian cell contains a gene selected from the group consisting of TGF-β1, cyclin D1, p21, p34, p53, ras, and myc.]

[12. The method of claim 1 wherein the mammalian cell is isolated from the same species as the host mammal.]

[13. The method of claim 1 wherein the mammalian cell and the host mammal are histocompatible.]

[14. The method of claim 1 wherein the mammalian cell and the host mammal are syngeneic.]

[15. The method of claim 1 wherein the transfected cell is isolated and maintained in vivo or in vitro for a period of time prior to introduction of said cell to the host mammal.]

[16. The method of claim 1 wherein the expressed sequences of the transfected cells are obtained from a cell line of immortalized transfected cells.]

[17. The method of claim 1 wherein the transfected cells are administered to the primary site by subcutaneous implantation.]

[18. The method of claim 1 wherein the host mammal is a mouse, a rabbit or a primate.]

[19. The method of claim 1 wherein the host mammal is a syngeneic, xenogeneic, immunocompromised or transgenic host mammal.]

[20. The method of claim 1 further comprising suppressing expression of TGF-α in the host mammal prior to the introduction of transfected cells into said host mammal.]

[21. The method of claim 1 wherein the primary site is the renal capsule, the prostate or the testis.]

[22. The method of claim 1 wherein the secondary site is selected from the group of sites consisting of lung, kidney, liver, lymph nodes, brain, bone, testis, spleen, ovaries and mammary.]

[23. The method of claim 1 wherein differential display PCR is performed with an anchor primer and a variable primer.]

[24. The method of claim 22 wherein the anchor primer comprises a polythymidine sequence and a dinucleotide sequence connected to a 3'-terminus.]

[25. The method of claim 24 wherein the polythymidine sequence comprises between about 5 to about 30 thymidines.]

[26. The method of claim 24 wherein the dinucleotide sequence is selected from the group of sequences consisting of AA, AG, AC, AT, GA, GG, GC, GT, CA, CG, CC and CT.]

[27. The method of claim 23 wherein the anchor primer or the variable primer comprise a detectable moiety selected from the group consisting of radioactive moieties, phosphorescent moieties, magnetic moieties, luminescent moieties and conjugatable moieties.]

[28. The method of claim 23 wherein the anchor primer and the variable primer have a common sequence.]

[29. The method of claim 7 wherein the agent is a retinoid.]

[30. A method for identifying a sequence expressed in metastasis comprising the steps of:

a) pretreating a mammalian cell with an agent that enhances metastatic potential to form a population of cells predisposed to metastasis;

b) introducing the pretreated cells to a primary site of a host mammal;

c) maintaining said mammal for a period of time sufficient to develop a metastasis at a secondary site;

d) amplifying expressed RNA sequences of pretreated cells and expressed RNA sequences of the metastasis by differential-display PCR; and e) identifyg the sequence expressed at a higher level in the metastasis as compared to expressed RNA sequences of the pretreated cells.]

[31. The method of claim 30 further comprising the step of treating cells of the primary or secondary sites with a genotoxic agent prior to amplification.]

[32. The method of claim 31 wherein the genotoxic agent is benzanthracene (BA), dimethyl benzanthracene (DMBA) or 5-azacytidine.]

[33. The method of claim 30 further comprising the step of comparing the expressed sequences amplified from the metastasis with expressed sequences amplified from mammalian cells before pretreatment to identify the sequence selectively expressed in the metastasis.]

[34. The method of claim 30 wherein the chemical compound is a benzanthracene, dimethyl benzanthracene, or 5-azacytidine.]

[35. The method of claim 30 wherein the mammalian cell is transfected, prior to the administration of said cell to the host mammal, with an oncogenic sequence before or after treatment of said cell with the agent that enhances metastatic potential.]

[36. The method of claim 30 wherein the mammalian cell is a cell line.]

[37. The method of claim 30 wherein the mammalian cell is isolated from lymphatic tissue, hematopoietic cells, reproductive tissues or urogenital sinus tissue.]

[38. The method of claim 30 wherein the mammalian cell is a fetal cell.]

[39. The method of claim 30 wherein the mammalian cell is isolated from a transgenic animal.]

[40. The method of claim 30 wherein the primary site is the renal capsule, the prostate or the testis.]

[41. The method of claim 30 wherein the secondary site is selected from the group of sites consisting of lung, kidney, liver, lymph nodes, brain, bone, testis, spleen, ovaries and mammary.]

[42. The method of claim 30 wherein differential display PCR is performed using an anchor primer and a variable primer.]

*43. A method of screening a biological tissue for the presence of a metastasis comprising contacting the tissue with a nucleic acid probe, wherein the probe detects the presence of a nucleic acid molecule comprising SEQ ID NO:89 or its complement, and wherein an increased level of a nucleic acid molecule comprising SEQ ID NO:89 or its complement in the biological tissue relative to the level of a nucleic acid molecule comprising SEQ ID NO:89 or its complement in a primary tumor is indicative of a metastasis.*

*44. The method of claim 1, wherein the tissue is lung, kidney, liver, lymph node, brain, testis, bone, spleen, ovary, or mammary tissue.*

*45. The method of claim 1, wherein the tissue is renal capsule, testis, prostate, or ovary tissue.*

*46. The method of claim 1, wherein the method comprises in situ hybridization of the probe with the tissue.*

*47. The method of claim 1, wherein nucleic acids are extracted from the tissue prior to contact with the probe.*

*48. The method of claim 5, wherein the nucleic acids are amplified prior to contact with the probe.*

*49. The method of claim 6, wherein the method comprises different display polymerase chain reaction.*

*50. The method of claim 1, wherein the primary tumor in a prostate tumor.*

* * * * *